(12) United States Patent
Tanaka et al.

(10) Patent No.: US 7,544,502 B2
(45) Date of Patent: Jun. 9, 2009

(54) POLYNUCLEOTIDE ENCODING POLYPEPTIDE HAVING LARVAE GROWTH INHIBITING OR INSECTICIDAL EFFECT ON SCARABAEIDAE INSECTS

(75) Inventors: Masao Tanaka, Chiba (JP); Tomoko Yokoyama, Chiba (JP); Moriichi Aoyagi, Katori-gun (JP); Makoto Hasegawa, Chiba (JP); Gaku Ehara, Sakura (JP); Masaharu Kimura, Ichihara (JP); Hideji Nishihashi, Sakura (JP)

(73) Assignee: DIC Corporation, Tokyo (JP)

( * ) Notice: Subject to any disclaimer, the term of this patent is extended or adjusted under 35 U.S.C. 154(b) by 300 days.

(21) Appl. No.: 11/091,654

(22) Filed: Mar. 29, 2005

(65) Prior Publication Data

US 2005/0172355 A1     Aug. 4, 2005

Related U.S. Application Data

(62) Division of application No. 10/120,544, filed on Apr. 12, 2002, now Pat. No. 7,033,993.

(30) Foreign Application Priority Data

| Apr. 13, 2001 | (JP) | ............................. 2001-115754 |
| Jul. 4, 2001 | (JP) | ............................. 2001-203463 |

(51) Int. Cl.
| *C12N 1/20* | (2006.01) |
| *C07H 21/02* | (2006.01) |
| *C07H 21/04* | (2006.01) |
| *C07K 17/00* | (2006.01) |

(52) U.S. Cl. ................. 435/252.3; 435/320.1; 536/23.1; 536/23.7; 530/350

(58) Field of Classification Search ....................... None
See application file for complete search history.

(56) References Cited

U.S. PATENT DOCUMENTS

| 3,876,666 | A |  | 4/1975 | Oswald et al. ........... 260/343.2 |
| 4,824,671 | A |  | 4/1989 | Ellis et al. ................. 424/195.1 |
| 5,262,158 | A |  | 11/1993 | Payne et al. |
| 5,554,534 | A |  | 9/1996 | Michaels et al. ......... 435/252.3 |
| 6,056,953 | A | * | 5/2000 | Hickle et al. ........... 424/93.461 |
| 6,103,496 | A | * | 8/2000 | Brash et al. ................ 435/69.1 |
| 6,204,057 | B1 |  | 3/2001 | Schnetter et al. ............ 435/418 |
| 2005/0271642 | A1 |  | 12/2005 | Asano et al. |

FOREIGN PATENT DOCUMENTS

| JP | 11-332556 | 12/1999 |
| JP | 2001-151617 | 6/2001 |
| WO | WO 97-14798 | 4/1997 |

OTHER PUBLICATIONS

Witkowski et al., Biochemistry 38:11643-11650, 1999.*
Yokoyama et al., J Invert Path 85:25-32, Jan. 2004.*
Jianbing Zhang et al.; ":Cloning and Analysis of the First *cry* Gene from *Bacillus popilliae*"; Journal of Bacteriology; Jul. 1997; vol. 179, No. 13, pp. 4336-4341.
EMBL Database listing: Foncerrada et al.; Jan. 28, 1997: "Antiscarab pest toxin 50C(a)"; Database accession No. AAWO6418.
EMBL Database listing: Foncerrada et al.; Jan. 28, 1997: "Antiscarab pest toxin 50C(a)"; Database accession No. AAT43222.
EMBL Database listing: Foncerrada et al.; Jan. 28, 1997: "Antiscarab pest toxin 50C(a)"; Database accession No. AAWO6417.
EMBL Database listing: Foncerrada et al.; Jan. 28, 1997: "Antiscarab pest toxin 50C(a)"; Database accession No. AAT43221.
Canadian Journal Microbiology (1967) 13:279-285.
Branden et al. "Introduction to Protein Structure", Garland Publishing Inc., New York, 1991.
"Encyclopedia of Molecular Biology," Creigton T.E., John Wiley and Sons, Inc., New York, 1999, p. 1250-1252.
"Biochemistry," 2$^{nd}$ Ed., Voet, D., and Voet, J.G., John Wiley and Sons, Inc., New York, 1995, p. 905.
Grove, M. et al. *Biocontrol*, 46(3), 321-335 (2001) abstract entitled "Effects of individual *Bacillus thuringiensis* insecticidal crystal proteins on adult Heliothis virescens (F.) And Spodoptera exigua (Hubner) (Lepidoptera: Noctuidae)."
Yamagiwa, M. et al. *Applied and Environmental Microbiology*, 65(8), 3464-3469 (1999); entitled "Activation Process of Dipteran Specific Insecticial Protein Prouced by *Bacillus thuringiensis* subsp. *Israelensis*."
T. Yokoyama et al., "A new strain of *Paenibacillus lentimorbus* isolated from larvae of the oriental beetle, *Blitopertha orientalis* (Coleoptera: Scarabaeidae), in Chiba Prefecture, Japan," Appl. Entomol. Zool. 38(4), 2003, pp. 523-528.
Machine Translation of JP11-332556 at www19.jpdl.inpit.go.jp/PA1/cgi-bin/PA1INDEX, last viewed on Nov. 8, 2007.
B. A. Weiner, "Isolation and partial characterization of the parasporal body of *Bacillus popillae*," Can J. Microbiol 24: 1557-1561, 1978.

* cited by examiner

*Primary Examiner*—David J Steadman
(74) *Attorney, Agent, or Firm*—Edwards Angell Palmer & Dodge LLP

(57) ABSTRACT

Through screening using an antibody to a polypeptide that constitutes a parasporal body in sporangia of *Bacillus popilliae* and has a larvae growth inhibiting or insecticidal effect on a Scarabaeidae insect and through polymerase chain reaction, polynucleotides encoding the polypeptide and polypeptides similar thereto are isolated.

3 Claims, 7 Drawing Sheets

Fig. 5

SEQ ID NO:

```
18    1:------------------------------------MQIIQPSSNALLYSPNKYPYATD  23
20    1:--------------------MNQYHNQNDNKSYNQSGNEMQIIQPSSNSLLYSPNKYPYATD  42
 4    1:MLWLNTHCSLIGITGRQTMNQYHNQNDNKSYNQSGNEMQIIQPSSNALLYSPNKYPYATD  60
 6    1:MLWLNTHCSLIEITGRQTMNQYHNQNDNKSYNQSGNEVQIIQPSSNALLYSPNKYPYATD  60

18   24:PNVIAEGRSYNNWLDTCVGVGDGTRSPEAYAIAEE-AVGLSIDILAEIIYYLGFPIAS-P   81
20   43:PNVIAEGRSYKNWLDMCVGEGDGTRSLEAIAVAVG-VR-----ISHTIFRLLGVPYSAQ-  95
 4   61:PNVIAEGGSYKNWLDMCTGTCD-TRSPETAAISKCAVSAAIT-ISTGLLGLLGVPFASQI 118
 6   61:PNVIAEGRSYKNWLDMCVGVGDDTRSPEAR-VTAQSSISTSLGITSTIIGALGIPVVGEA 119

18   82:LTRA-LSAIAGQLFSSG-DTL---MQHIEQLINQKIAEYARNKALAEFQGLGRQYGLYLE 136
20   96:GEQLFSFLLDT-LMLEGNTQWEELMRHAEELINEQVPDYVRTKALAELTDLGNNLNLYIA 154
 4  119:G-AFYTFLLNT-LWPASNTQWEQFIAHVEELINAKLTDHVRNSALTKLNGLRNNIEIYNE 176
 6  120:I--GIFGALLDWLWPAGADPWVIFMNHVEELINSKITETVKNEAITRLDGLGNVLALYQK 177

18  137:ALEDWEQNR-LSQPHKERVRQTFRILDNS-FTSSIPSFAVRNYEVPLLSVYADAANLHLL 194
20  155:AFEDWKRNPSSQEVRTR-VIDRF-NILDGLFEAYLPSFAVPGYEVPLLSVYANVVNIHLL 212
 4  177:ALIVWKQDPNNSKLKDD-VRSKFVG-LNSQFEEYIPQFKEEGFEVQLLTIYAQSANLHLL 234
 6  178:AFEEWQQHPTLESA-RLRVTDDFSNVNKF-FEAFMPSFRVPGYEVPLLSVYVSAANLHLL 235

18  195:ILRDSYIYG-AFWGFDEDEYYRNYARQIRLSAEYANHCT-TWYQTGLRRLQGTRATDWIN 252
20  213:VLRDSSIYGLD-WGLSSTSVDNNYNRQQRNSATYANHCT-TWYQTGLQRLQGSDASSWVN 270
 4  235:LLRDSSLYGAS-WGFAQATIDNNYNRQIRKTAEYANHCT-TWYQTGLQRLQGTTASSWLS 292
 6  236:LLRDSSIFGLD-WGLSQTHVNDNYNLQIRRSADYANHCT-TWYRTGLQRLQGTNASSWVN 293

18  253:YNRFRREMTLTVLDICALFSSYDIPSYPMGTKIQLTREIYTDP-VVHSD----WLQSTSP 307
20  271:YNRFRREITLIVLDICALFSNYDVRSYPIQLRGELTRGIYTDPAVYSGTGSYSWLSQA-P 329
 4  293:YHRFRREMTLTVLDICALFSNYDARSYPLEVRGELTREIYTDP-VAPGTN---WIDRA-P 347
 6  294:YNRFRREMTLTVLDVCALFSSYDYRSYPMELRGELTREIYTDP-VGA-SF---WVNRA-P 347

18  308:GLISFSSLENLVVRAPHLFTWLSRVTID--TGILSTVIGGQYSNNNF-WRTHYQTLRTTG 364
20  330:S---FAEIENIAIREPSNFTWASYARVT--TGTLE----YLSSKNDF-WKSHYMNYTEIN 379
 4  348:S---FAEIENLVIRAPRTVTWI-SGDLIVYTGR-LY--GYTGNW-DY-WAAHRLDFLETN 398
 6  348:N---FASIENTVVRQPHPFTWLVTLTVN--TGQVRS--G--DGNSNYYWKSHSQTVSEIG 398

18  365:-GT-SFQSPTYGSTAFP--IQRTNT--LTFS-----GDVYTIESSVV-TRSSLYGANSVA 412
20  380:SGILI-QGPTYGMTTGTN I--RIESVSMQE--IYSVRLEAVAH-AGAGGPF-LGISTSE 431
 4  399:-GYRF-EGPTYGSTI--NIS-RTDSIPMNSIDVYSTTVVTVGSAWPTG-GFVL-CVASAR 451
 6  399:-GSGPIQSPTCGSTG-T-IY-RTDN--LLFNP-FLLGDIYTINTGYVSYLANLFGIYSAR 451

18  413:-FTGTTGRS--L-----YENPTVY-PFAQKLIHE--LPGVDSGRPNATNYSHRLSYISGF 461
20  432:FFW-----S---LGVRRYQNSRS-PQ-FASQIITRQLPGVNSAVPSALDHSHELSYITAF 481
 4  452:FFSKSP--STGLLGERVYQN----PVYFSSSTLTFNLPGVDQDTPTAADYSHKLSCITAF 505
 6  452:-FTT-T-RSIEL-L---YENQRVFPAYNHQ-IRE--LPGVNSDRPTAADYSHRLSYISGF 501
```

Fig. 6

SEQ ID NO:

```
18   462:SLGYSPSGTGLVYGWTSTTATRENNITLDDRIVQLPAVKGASLNNCQVVKGTGFTGGDWL 521
20   482:PVRS-V-GTILVHEWTSTTVSRNNRIEPD-KITQIPAVKSHTLSNCQVVSGTGFTGGNWL 538
 4   506:--RTGLNGTVPVFGRYSATVSRDNRIEPD-KITQIPAVKSNSLDNCPVVRGTGFTGGDWL 562
 6   502:ATDVG--GTVLVYGWTSSTATRENNITLDDRIVQLPAVKGTSLNNCQVVRGTGFTGGDWL 559

18   522:KPNNNGTFSMYFAF-RSAY--TYHFRIRYASSA---SFSFVISEEYGRFPTTTVPLLSTM 575
20   539:RPSDNGSFRLTITS-FS-S-QSYRIRIHYASA-TFFYLD-IRTGDT-S-NTFAVTPTTLS 591
 4   563:KTSYLSVFVLTITS--SRAGQSYRIRVRYAAAVDLI-MS-IYSNDPFISKGISLTKS-MP 617
 6   560:KPNNNGTFSLALGF-RSTY--TYRLRIRYAAAAGGSGFSLVISDQYGEFPTTTVSLSSTM 616

18   576:SPLPQNTPFEAFKTVDLPSTVTIRYTS--AASTTFQLNFRFTV-PGS-ANVLIDRIEFVP 631
20   592:SGSQTV-PYESFGFINIPYTFTTAPTESRY---TFDFM--FYSI-GSANVLIDRIEIVP 643
 4   618:PLTETV-PYEAFKFADFGVTFTTATANKRY---TFQF----HTG-G-AAI--IDRIEFVP 665
 6   617:YSLPQNVPYEAFKIVDLPSTVTIRNTS--PASTTFRLDFRFIVPLGILANILIDRIEFVP 674

18   632:IEGS-LFEYETKQQLEKARKAVNHLFTDGSKKALKEDTTDYEIDQAANVVDCISDECGHE 690
20   644:I-GVPLFEYETKQQLEKARKAVNHLFTDGSKKALKEDTTDYEIDQAANVVDCISDECGHD 702
 4   666:IEG-SLFEYETKQQLEKARKAVNHLFTDGSKKALKEGTTDYEIDQAANVVDCISDECGHE 724
 6   675:IEGS-LFEYETKQQLEKARKAVNHLFTDGSKKALKEGTTDYEIDQAANVVDCISDECGHE 733

18   691:KMILLDEVKYAKQLSQARNLLLNGNFDDLYPALERENPWKTSPNVTIRQDNPIFKGHYLS 750
20   703:KMILLDEVKYAKQLSQARNLLLNGNFDDLYSALEKENPWKTSPNVTIRQDNPIFKGHYLS 762
 4   725:KMILLDEVKYAKQLSQARNLLLNGNFDDLYPALERENPWKTSPHVTIRQDNPIFKGHYLS 784
 6   734:KMILLDEVKYAKQLSQARNLLLNGNFDDLYPALERENPWKTSPNVTIRQDNPIFKGHYLS 793

18   751:MAGANDIEATNDTFPTYVYQKIDEAKLKPYTRYKVRGFVGSSKDLELLVTRYNEEVDAIL 810
20   763:MAGANDIEATNDTFPTYVYQKIDEAKLKPYTRYKVRGFVGSSKALELLVTRYNEEVDAIL 822
 4   785:MAGANDIEATNDTFPTYVYQKIDEAKLKPYTRYKVRGFVGSSKALELLVTRYNEEVDAIL 844
 6   794:MAGANDIEATNDTFPTYAYQKIDEAKLKPYTRYKVRGFVGSSKALELLVTRYNEEVDAIL 853

18   811:DVPDNIPHAPTPVCGEFDRCKPYSYPPLLPECNPEFINQMQPSSCHHNQMVDYNNMNTST 870
20   823:DVPDNIPHAPTPVCGEFDRCKPYSYPPLLPECNPEFINQMQPSSCHHNQMVDYNNMNTST 882
 4   845:DVPDNIPHAPTPVCGEFDRCKPYSYPPLLPECNPEFINQMQPSSCHHNQMVDYNN----- 899
 6   854:DVPDNIPHAPTPVCGEFDRCKPYSYPPLLPECNPEFINQMQPSSCHHTQMVDYNNMNMST 913

18   871:STTMNPSMNPPLTPEIASSQSGFGRKHRKCHQAHQFEFHIDTGTIDLVEDLGIWVIFKIC 930
20   883:STTMNPSMNPPLTPEIASSQSGFGRKHRKCHQAHQFEFHIDTGTIDLVEDLGIWVIFKIC 942
 4   900:---------------------RKHRKCHQAHQFEFHIDTGTIDLVEDLGIWVIFKIC 935
 6   914:STTMNP-----TLTPEIASSQSGFGRKHRKCHQAHQFEFHIDTGTIDLVEDLGIWVIFKIC 969

18   931:ATDGYASLDDLEVIEEGALGVEALELVKKREKKWRHQKEQHCSQTKHKYDAAKHAVMALF 990
20   943:ATDGYASLDDLEVIEEGALGVEALELVKKREKKWRHQKEQHCSQTKHKYDAAKHAVMALF 1002
 4   936:ATDGYASLDDLEVIEEGALGVEALELVKKREKKWRHQKEQHCSQTKHKYDAAKHAVMALF 995
 6   970:ATDGYASLDDLEVIEEGALGVEALELVKKREKKWRHQKEQHCSQTKHKYDAAKHAVMALF 1029
```

Fig. 7

| SEQ ID NO: | | | |
|---|---|---|---|
| 18 | 991: | TNTRYEKLKFETTISDILYADHLVQSIPYVYNKYVPEVSGMNYELYTELNTLVQNAFYLY | 1050 |
| 20 | 1003: | TNKRYEKLKFETTISDILYADHLVQSIPYVYNKYVPEVPGMNYELYSELNTLVQNAFYLY | 1062 |
| 4 | 996: | TNTRYEKLKFETTISNILYADHLVQSIPYVYNKYVPEVPGMNYELYTELNTLVQNAFYLY | 1055 |
| 6 | 1030: | TNTRYEKLKFETTISDILYADHLVQSIPYVYNKYVPEVPGMNYELYSELNTLVQNAFYLY | 1089 |
| 18 | 1051: | DQRNLIKNGRFSNGLMYWQATPHARVEQEYDRSVLVLPNWDANVSQQLCIEHNRGYVLRV | 1110 |
| 20 | 1063: | DQRNLIKNGRFSNGLMHWQATPHARVEQEYEKSVLVLPNWDANVSQDLCIEHNRGYVLRV | 1122 |
| 4 | 1056: | DQRNLIKNGRFSNGLMYWQATPHARVEQEYEKSVLVLPNWDANVSQDLCIEHNRGYVLRV | 1115 |
| 6 | 1090: | DQRNLIKNGRFSNGLMHWQATPHARVEQEHEKSVLVLPNWDANVSQDLCIEHNRGYVLRV | 1149 |
| 18 | 1111: | TARKEDPGAGNVTFSDCANHVDKLSFTSCDIATNAVPGAQANDPAAGVAYGQQGCQIDRV | 1170 |
| 20 | 1123: | TARKEDPGAGNVTFSDCENHVDKLSFTSCDIATNAVPGAQANDPAAGVAYGQQGCQIDRV | 1182 |
| 4 | 1116: | TARKEDPGAGNVTFSDCANHVDKLSFTSCDIATNAVPGAQANDPAAGVAYGQQGCQIDRV | 1175 |
| 6 | 1150: | TARKEDPGAGNVTFSDCANHVNKLSFTSCDIATNAVPGAQANDPAAGVAYGQQGCQIDRV | 1209 |
| 18 | 1171: | PYGPSGYRADGV---AYEQSGHRTDGVPYRQSGYRADGVAHDQPGYRADGVAYEQSGYRA | 1227 |
| 20 | 1183: | PYGQSGYRADGV---AYEQSGHRTDGVPYRQSGYGTDGVTYEQSGHRADGVPYGQSGYRA | 1239 |
| 4 | 1176: | PYGQSGYRTDGTNGMPYGQSGNRADGVPYRQSGYGTDGVAHDQPGYRADGVAYEQSGYRA | 1235 |
| 6 | 1210: | PYGQSGYRTDGTNGMPYGQSGNRADGVPYRQSGYGTDGVAHDQPGYRADGAAYEQSGHRA | 1269 |
| 18 | 1228: | DGVA-----------YEQSGHRADGVPYGQSGYGTDGVTYDQSAKQTRKYHGCHTDGLP | 1275 |
| 20 | 1240: | DGVA-----------YEQSGHRADGVPYGQSGYGTDGVTYDQSANQTRKYHGCHTDGLP | 1287 |
| 4 | 1236: | DGVT---------------------------------------YDQSANQTRKYHGCHTVGLP | 1259 |
| 6 | 1270: | DGVAYEQSGYRAGGVAYEQSGHRADGVPYGQSGYGTDGVTYDQSVKQTRKYHGCHTDGLP | 1329 |
| 18 | 1276: | HPEHGCCYPDRVSDGQQLAYVTKSIDLFPDTDKVRIDIGETEGNFRVESVELICMEK | 1332 |
| 20 | 1288: | HPEHGCCYPDRVSDGQQLAYVTKSIDLFPDTDKVRIDIGETEGNFRVESVELICMEK | 1344 |
| 4 | 1260: | HPEHGCCYPDRVSDGQQLAYVTKSIDLFPDTDKVRIDIGETEGNFRVESVELICMEK | 1316 |
| 6 | 1330: | HPEHGCCYPDRVSDGQQLAYVTKSIDLFPDTDKVRIDIGETEGNFRVESVELICMEK | 1386 |

SEQUENCE LISTING

```
<160> NUMBER OF SEQ ID NOS: 22

<210> SEQ ID NO 1
<211> LENGTH: 402
<212> TYPE: DNA
<213> ORGANISM: Bacillus popilliae
<220> FEATURE:
<221> NAME/KEY: CDS
<222> LOCATION: (1)..(402)

<400> SEQUENCE: 1 aga aaa cac cgc aaa tgt cat caa gcg cat caa ttt gag ttc cat att      48
Arg Lys His Arg Lys Cys His Gln Ala His Gln Phe Glu Phe His Ile
  1               5                  10                  15 gat acc ggg aca atc gat ctg gtc gaa gat ttg ggc att tgg gtg atc      96
Asp Thr Gly Thr Ile Asp Leu Val Glu Asp Leu Gly Ile Trp Val Ile
             20                  25                  30 ttc aaa atc tgt gcc aca gat ggt tac gca agc tta gat gat ttg gaa     144
Phe Lys Ile Cys Ala Thr Asp Gly Tyr Ala Ser Leu Asp Asp Leu Glu
         35                  40                  45 gtg att gaa gaa gga gcg ctg ggt gtc gaa gca tta gaa ctt gtc aag     192
Val Ile Glu Glu Gly Ala Leu Gly Val Glu Ala Leu Glu Leu Val Lys
     50                  55                  60 aaa aga gaa aag aaa tgg aga cat cag aag gag cag cac tgt tcg caa     240
Lys Arg Glu Lys Lys Trp Arg His Gln Lys Glu Gln His Cys Ser Gln
 65                  70                  75                  80 acg aaa cac aaa tat gat gcg gcc aaa cac gcg gtg atg gcg tta ttc     288
Thr Lys His Lys Tyr Asp Ala Ala Lys His Ala Val Met Ala Leu Phe
                 85                  90                  95 aca aac acg cgc tat gaa aaa ttg aag ttc gaa aca acc atc tcc aat     336
Thr Asn Thr Arg Tyr Glu Lys Leu Lys Phe Glu Thr Thr Ile Ser Asn
            100                 105                 110 att ttg tat gct gat cat ctc gtg cag tcg att cct tat gta tat aat     384
Ile Leu Tyr Ala Asp His Leu Val Gln Ser Ile Pro Tyr Val Tyr Asn
        115                 120                 125 aaa tat gta ccg gaa gtt                                             402
Lys Tyr Val Pro Glu Val
    130

<210> SEQ ID NO 2
<211> LENGTH: 134
<212> TYPE: PRT
<213> ORGANISM: Bacillus popilliae

<400> SEQUENCE: 2

Arg Lys His Arg Lys Cys His Gln Ala His Gln Phe Glu Phe His Ile
  1               5                  10                  15

Asp Thr Gly Thr Ile Asp Leu Val Glu Asp Leu Gly Ile Trp Val Ile
             20                  25                  30

Phe Lys Ile Cys Ala Thr Asp Gly Tyr Ala Ser Leu Asp Asp Leu Glu
```

-continued

```
                35                  40                  45
Val Ile Glu Glu Gly Ala Leu Gly Val Glu Ala Leu Glu Leu Val Lys
     50                  55                  60

Lys Arg Glu Lys Lys Trp Arg His Gln Lys Glu Gln His Cys Ser Gln
 65                  70                  75                  80

Thr Lys His Lys Tyr Asp Ala Ala Lys His Ala Val Met Ala Leu Phe
                 85                  90                  95

Thr Asn Thr Arg Tyr Glu Lys Leu Lys Phe Glu Thr Thr Ile Ser Asn
                100                 105                 110

Ile Leu Tyr Ala Asp His Leu Val Gln Ser Ile Pro Tyr Val Tyr Asn
                115                 120                 125

Lys Tyr Val Pro Glu Val
            130

<210> SEQ ID NO 3
<211> LENGTH: 4359
<212> TYPE: DNA
<213> ORGANISM: Bacillus popilliae
<220> FEATURE:
<221> NAME/KEY: CDS
<222> LOCATION: (282)..(4229)

<400> SEQUENCE: 3
gctgcattcc ctttatcatc aatattgaag tcaaaccgaa gggaaatcgt gaaacatgtt      60
ttactgaccc ccatgccaaa gaaatctcac tttgttgtga ggggagtgta tgtgtagacc     120
atgtactcaa atgcagtgtc ggaagtttgc cagatgttca tatcaattgt aaatatgtga     180
cggtatgtga tttacagatg aggcccgttc atgagggagc ttgtcaattt gtgaagatta     240
gcggagaatt tcaatttat tcactttaac attagctaca a atg ttg tgg cta aat      296
                                              Met Leu Trp Leu Asn
                                                1               5 act cat tgt tca tta ata gga ata act ggg agg caa act atg aat caa      344
Thr His Cys Ser Leu Ile Gly Ile Thr Gly Arg Gln Thr Met Asn Gln
             10                  15                  20 tat cat aac caa aac gat aac aaa agt tac aac caa agt gga aat gaa      392
Tyr His Asn Gln Asn Asp Asn Lys Ser Tyr Asn Gln Ser Gly Asn Glu
         25                  30                  35 atg caa atc att caa cct tca agt aac gct tta ctt tac agt ccc aat      440
Met Gln Ile Ile Gln Pro Ser Ser Asn Ala Leu Leu Tyr Ser Pro Asn
     40                  45                  50 aag tat ccg tat gct acg gat ccc aat gtc ata gca gag ggt gga agt      488
Lys Tyr Pro Tyr Ala Thr Asp Pro Asn Val Ile Ala Glu Gly Gly Ser
 55                  60                  65 tat aaa aat tgg ttg gat atg tgt aca ggg aca ggc gac aca cga agc      536
Tyr Lys Asn Trp Leu Asp Met Cys Thr Gly Thr Gly Asp Thr Arg Ser
 70                  75                  80                  85 ccc gaa act gct gct att tca aaa ggt gct gtt tct gct gca att act      584
Pro Glu Thr Ala Ala Ile Ser Lys Gly Ala Val Ser Ala Ala Ile Thr
             90                  95                 100 ata agc acc ggg ctt ctt ggc tta cta ggt gtt ccg ttt gca tca caa      632
Ile Ser Thr Gly Leu Leu Gly Leu Leu Gly Val Pro Phe Ala Ser Gln
        105                 110                 115 atc ggg gca ttt tat acc ttc cta ttg aat acc tta tgg cct gca agc      680
Ile Gly Ala Phe Tyr Thr Phe Leu Leu Asn Thr Leu Trp Pro Ala Ser
    120                 125                 130 aat act caa tgg gag cag ttt ata gca cat gtg gaa gaa ctc ata aat      728
Asn Thr Gln Trp Glu Gln Phe Ile Ala His Val Glu Glu Leu Ile Asn
135                 140                 145
```

```
gca aaa cta aca gat cat gta aga aat tcg gca ctt aca aaa tta aat        776
Ala Lys Leu Thr Asp His Val Arg Asn Ser Ala Leu Thr Lys Leu Asn
150                 155                 160                 165 ggt tta cgt aat aac ata gag ata tat aac gaa gct tta ata gtt tgg        824
Gly Leu Arg Asn Asn Ile Glu Ile Tyr Asn Glu Ala Leu Ile Val Trp
                170                 175                 180 aaa caa gat cct aac aat agc aaa cta aaa gat gat gta aga agt aaa        872
Lys Gln Asp Pro Asn Asn Ser Lys Leu Lys Asp Asp Val Arg Ser Lys
            185                 190                 195 ttc gta ggt cta aat agc caa ttc gaa gaa tat att cca caa ttt aaa        920
Phe Val Gly Leu Asn Ser Gln Phe Glu Glu Tyr Ile Pro Gln Phe Lys
        200                 205                 210 gaa gaa ggt ttt gaa gtt caa tta tta act ata tat gca caa tct gca        968
Glu Glu Gly Phe Glu Val Gln Leu Leu Thr Ile Tyr Ala Gln Ser Ala
    215                 220                 225 aat ctt cat cta tta tta tta aga gat tcc tct ttg tat ggt gca tct       1016
Asn Leu His Leu Leu Leu Leu Arg Asp Ser Ser Leu Tyr Gly Ala Ser
230                 235                 240                 245 tgg gga ttt gct caa gct act att gac aat aat tac aat cgc caa ata       1064
Trp Gly Phe Ala Gln Ala Thr Ile Asp Asn Asn Tyr Asn Arg Gln Ile
                250                 255                 260 agg aaa acc gca gag tat gca aat cat tgt acc act tgg tat cag acg       1112
Arg Lys Thr Ala Glu Tyr Ala Asn His Cys Thr Thr Trp Tyr Gln Thr
            265                 270                 275 ggt tta caa aga ttg caa ggc act act gct agc agt tgg ctc tct tat       1160
Gly Leu Gln Arg Leu Gln Gly Thr Thr Ala Ser Ser Trp Leu Ser Tyr
        280                 285                 290 cat aga ttt aga aga gaa atg aca cta aca gta ttg gat att tgc gca       1208
His Arg Phe Arg Arg Glu Met Thr Leu Thr Val Leu Asp Ile Cys Ala
    295                 300                 305 tta ttt tca aat tat gat gcc cgt agt tac cca ctg gag gta agg gga       1256
Leu Phe Ser Asn Tyr Asp Ala Arg Ser Tyr Pro Leu Glu Val Arg Gly
310                 315                 320                 325 gag ctt acg aga gaa att tat acg gat cca gta gca ccc ggt act aac       1304
Glu Leu Thr Arg Glu Ile Tyr Thr Asp Pro Val Ala Pro Gly Thr Asn
                330                 335                 340 tgg ata gat cga gca cca tca ttc gca gaa ata gaa aat cta gta att       1352
Trp Ile Asp Arg Ala Pro Ser Phe Ala Glu Ile Glu Asn Leu Val Ile
            345                 350                 355 agg gca cca aga act gtt act tgg ata tcc ggt gat tta ata gta tat       1400
Arg Ala Pro Arg Thr Val Thr Trp Ile Ser Gly Asp Leu Ile Val Tyr
        360                 365                 370 aca ggt aga ttg tac ggc tat act ggt aat aac gat tat tgg gca gca       1448
Thr Gly Arg Leu Tyr Gly Tyr Thr Gly Asn Asn Asp Tyr Trp Ala Ala
    375                 380                 385 cac agg cta gat ttt ctt gaa acc aat ggt tat cgg ttt gag ggt cct       1496
His Arg Leu Asp Phe Leu Glu Thr Asn Gly Tyr Arg Phe Glu Gly Pro
390                 395                 400                 405 acc tat gga tcg acg att aat ata agt cgt aca gat tct att ccc atg       1544
Thr Tyr Gly Ser Thr Ile Asn Ile Ser Arg Thr Asp Ser Ile Pro Met
                410                 415                 420 aat tct att gat gtt tat tcc act act gta gtg act gtt ggc tct gct       1592
Asn Ser Ile Asp Val Tyr Ser Thr Thr Val Val Thr Val Gly Ser Ala
            425                 430                 435 tgg cca act ggc ggt ttt gtg ttg gga gtc gct tcg gct aga ttt ttt       1640
Trp Pro Thr Gly Gly Phe Val Leu Gly Val Ala Ser Ala Arg Phe Phe
        440                 445                 450 tcg aaa agt cct agc acc ggt tta tta ggt gag cgg gtg tat cag aat       1688
Ser Lys Ser Pro Ser Thr Gly Leu Leu Gly Glu Arg Val Tyr Gln Asn
    455                 460                 465
```

```
cca gta tat ttt tcg agt tcc act tta act ttt aac tta cct gga gta      1736
Pro Val Tyr Phe Ser Ser Ser Thr Leu Thr Phe Asn Leu Pro Gly Val
470                 475                 480                 485 gac caa gat acg cca act gct gcc gac tat agt cat aaa cta tcg tgt      1784
Asp Gln Asp Thr Pro Thr Ala Ala Asp Tyr Ser His Lys Leu Ser Cys
                490                 495                 500 atc aca gca ttt cga act gga ttg aat gga act gtt ccg gtt ttt gga      1832
Ile Thr Ala Phe Arg Thr Gly Leu Asn Gly Thr Val Pro Val Phe Gly
            505                 510                 515 cgg tat tct gca act gtt agt cgt gac aat aga att gag cca gac aaa      1880
Arg Tyr Ser Ala Thr Val Ser Arg Asp Asn Arg Ile Glu Pro Asp Lys
        520                 525                 530 ata acg caa atc ccg gct gtt aag tca aac tcc ctc gac aat tgt cca      1928
Ile Thr Gln Ile Pro Ala Val Lys Ser Asn Ser Leu Asp Asn Cys Pro
    535                 540                 545 gta gtt aga ggg act gga ttt aca gga gga gac tgg ttg aag aca agt      1976
Val Val Arg Gly Thr Gly Phe Thr Gly Gly Asp Trp Leu Lys Thr Ser
550                 555                 560                 565 tat ctt agt gtt ttt gtc cta act atc act tca tcg aga gcg ggc caa      2024
Tyr Leu Ser Val Phe Val Leu Thr Ile Thr Ser Ser Arg Ala Gly Gln
                570                 575                 580 tct tac cgc atc cgc gtc cgt tat gct gct gca gta gat tta att atg      2072
Ser Tyr Arg Ile Arg Val Arg Tyr Ala Ala Ala Val Asp Leu Ile Met
            585                 590                 595 agt ata tat tct aat gac cct ttt att tcc aaa gga att agt ctt acc      2120
Ser Ile Tyr Ser Asn Asp Pro Phe Ile Ser Lys Gly Ile Ser Leu Thr
        600                 605                 610 aaa tca atg cca cca ctg acc gaa act gta cct tac gaa gct ttt aaa      2168
Lys Ser Met Pro Pro Leu Thr Glu Thr Val Pro Tyr Glu Ala Phe Lys
    615                 620                 625 ttt gca gat ttt ggt gtc act ttt aca aca gct act gct aac aaa aga      2216
Phe Ala Asp Phe Gly Val Thr Phe Thr Thr Ala Thr Ala Asn Lys Arg
630                 635                 640                 645 tat act ttt caa ttc cat acg ggt gga gca gct ata att gac aga att      2264
Tyr Thr Phe Gln Phe His Thr Gly Gly Ala Ala Ile Ile Asp Arg Ile
                650                 655                 660 gaa ttt gtt cca att gag ggt agt ttg ttc gag tac gaa acc aaa caa      2312
Glu Phe Val Pro Ile Glu Gly Ser Leu Phe Glu Tyr Glu Thr Lys Gln
            665                 670                 675 cag cta gaa aaa gca agg aaa gcg gtg aac cat ttg ttt aca gat gga      2360
Gln Leu Glu Lys Ala Arg Lys Ala Val Asn His Leu Phe Thr Asp Gly
        680                 685                 690 tcg aaa aag gcg cta aaa gaa ggc acg acc gat tat gag atc gat caa      2408
Ser Lys Lys Ala Leu Lys Glu Gly Thr Thr Asp Tyr Glu Ile Asp Gln
    695                 700                 705 gcc gcc aac gtg gtg gat tgt ata tcg gat gag tgt gga cat gag aaa      2456
Ala Ala Asn Val Val Asp Cys Ile Ser Asp Glu Cys Gly His Glu Lys
710                 715                 720                 725 atg atc ctg tta gat gaa gta aaa tat gca aaa caa ctc agc caa gcc      2504
Met Ile Leu Leu Asp Glu Val Lys Tyr Ala Lys Gln Leu Ser Gln Ala
                730                 735                 740 cgc aat tta ctg ctc aat ggg aat ttc gat gat cta tat cca gct ctg      2552
Arg Asn Leu Leu Leu Asn Gly Asn Phe Asp Asp Leu Tyr Pro Ala Leu
            745                 750                 755 gag agg gag aat cca tgg aaa aca agt ccg cat gtt acg atc cgt caa      2600
Glu Arg Glu Asn Pro Trp Lys Thr Ser Pro His Val Thr Ile Arg Gln
        760                 765                 770 gat aac ccg att ttt aaa ggc cat tat ctc agt atg gcg ggt gcg aac      2648
Asp Asn Pro Ile Phe Lys Gly His Tyr Leu Ser Met Ala Gly Ala Asn
```

-continued

|                                                                                          |      |
|------------------------------------------------------------------------------------------|------|
|         775                    780                    785 | |
| gat att gag gcc acc aat gat acc ttc ccc acg tat gtc tat caa aaa<br>Asp Ile Glu Ala Thr Asn Asp Thr Phe Pro Thr Tyr Val Tyr Gln Lys<br>790                   795                    800                 805 | 2696 |
| ata gac gaa gcc aaa tta aag cca tat aca cgg tat aaa gtg cgc ggg<br>Ile Asp Glu Ala Lys Leu Lys Pro Tyr Thr Arg Tyr Lys Val Arg Gly<br>                810                    815                    820 | 2744 |
| ttt gtt ggt agc agc aaa gct cta gag ctg ttg gtt aca cgc tat aat<br>Phe Val Gly Ser Ser Lys Ala Leu Glu Leu Leu Val Thr Arg Tyr Asn<br>           825                    830                    835 | 2792 |
| gaa gaa gtc gat gcg att tta gat gta ccg gat aat atc ccg cat gcg<br>Glu Glu Val Asp Ala Ile Leu Asp Val Pro Asp Asn Ile Pro His Ala<br>                840                    845                    850 | 2840 |
| ccg act cct gtc tgc ggt gaa ttt gat cga tgc aag ccc tat tcg tat<br>Pro Thr Pro Val Cys Gly Glu Phe Asp Arg Cys Lys Pro Tyr Ser Tyr<br>855                   860                    865 | 2888 |
| cca cct tta ctt cca gaa tgt aac cct gag ttt ata aat cag atg caa<br>Pro Pro Leu Leu Pro Glu Cys Asn Pro Glu Phe Ile Asn Gln Met Gln<br>870                   875                    880                 885 | 2936 |
| cca tcc tct tgc cac cac aat cag atg gtc gat tac aat aac aga aaa<br>Pro Ser Ser Cys His His Asn Gln Met Val Asp Tyr Asn Asn Arg Lys<br>                890                    895                    900 | 2984 |
| cac cgc aaa tgt cat caa gcg cat caa ttt gag ttc cat att gat acc<br>His Arg Lys Cys His Gln Ala His Gln Phe Glu Phe His Ile Asp Thr<br>           905                    910                    915 | 3032 |
| ggg aca atc gat ctg gtc gaa gat ttg ggc att tgg gtg atc ttc aaa<br>Gly Thr Ile Asp Leu Val Glu Asp Leu Gly Ile Trp Val Ile Phe Lys<br>                920                    925                    930 | 3080 |
| atc tgt gcc aca gat ggt tac gca agc tta gat gat ttg gaa gtg att<br>Ile Cys Ala Thr Asp Gly Tyr Ala Ser Leu Asp Asp Leu Glu Val Ile<br>935                   940                    945 | 3128 |
| gaa gaa gga gcg ctg ggt gtc gaa gca tta gaa ctt gtc aag aaa aga<br>Glu Glu Gly Ala Leu Gly Val Glu Ala Leu Glu Leu Val Lys Lys Arg<br>950                   955                    960                 965 | 3176 |
| gaa aag aaa tgg aga cat cag aag gag cag cac tgt tcg caa acg aaa<br>Glu Lys Lys Trp Arg His Gln Lys Glu Gln His Cys Ser Gln Thr Lys<br>                970                    975                    980 | 3224 |
| cac aaa tat gat gcg gcc aaa cac gcg gtg atg gcg tta ttc aca aac<br>His Lys Tyr Asp Ala Ala Lys His Ala Val Met Ala Leu Phe Thr Asn<br>           985                    990                    995 | 3272 |
| acg cgc tat gaa aaa ttg aag ttc gaa aca acc atc tcc aat att ttg<br>Thr Arg Tyr Glu Lys Leu Lys Phe Glu Thr Thr Ile Ser Asn Ile Leu<br>         1000                 1005                1010 | 3320 |
| tat gct gat cat ctc gtg cag tcg att cct tat gta tat aat aaa tat<br>Tyr Ala Asp His Leu Val Gln Ser Ile Pro Tyr Val Tyr Asn Lys Tyr<br>    1015                 1020                1025 | 3368 |
| gta ccg gaa gtt cca ggt atg aat tac gaa ctc tat aca gag cta aac<br>Val Pro Glu Val Pro Gly Met Asn Tyr Glu Leu Tyr Thr Glu Leu Asn<br>1030                 1035                1040               1045 | 3416 |
| act ctc gtt cag aat gcg ttc tat cta tat gac cag cgg aat ctg att<br>Thr Leu Val Gln Asn Ala Phe Tyr Leu Tyr Asp Gln Arg Asn Leu Ile<br>            1050                1055                1060 | 3464 |
| aaa aat ggg cgc ttt agc aat ggg ctt atg tat tgg cag gct acc ccg<br>Lys Asn Gly Arg Phe Ser Asn Gly Leu Met Tyr Trp Gln Ala Thr Pro<br>1065                 1070                1075 | 3512 |
| cat gca cga gtg gaa caa gaa tat gag aaa tct gta ctc gtg ctg cca<br>His Ala Arg Val Glu Gln Glu Tyr Glu Lys Ser Val Leu Val Leu Pro<br>            1080                1085                1090 | 3560 |
| aat tgg gat gcc aat gtg tcg caa gat ctt tgt atc gaa cac aat cgc | 3608 |

-continued

```
            Asn Trp Asp Ala Asn Val Ser Gln Asp Leu Cys Ile Glu His Asn Arg
               1095                1100                1105 ggt tat gta ttg cgt gtc acg gcg aga aaa gaa gat ccg gga gct ggc      3656
Gly Tyr Val Leu Arg Val Thr Ala Arg Lys Glu Asp Pro Gly Ala Gly
1110                1115                1120                1125 aat gtt acc ttc agt gac tgt gca aac cat gtc gac aag ctg agc ttt      3704
Asn Val Thr Phe Ser Asp Cys Ala Asn His Val Asp Lys Leu Ser Phe
                1130                1135                1140 act tct tgc gat ata gct aca aac gca gtg cca ggt gcc caa gcg aat      3752
Thr Ser Cys Asp Ile Ala Thr Asn Ala Val Pro Gly Ala Gln Ala Asn
            1145                1150                1155 gat cca gcc gcc gga gta gcc tat gga caa cag ggc tgt caa ata gat      3800
Asp Pro Ala Ala Gly Val Ala Tyr Gly Gln Gln Gly Cys Gln Ile Asp
        1160                1165                1170 aga gtg ccg tac gga caa tct gga tat aga aca gac gga aca aat gga      3848
Arg Val Pro Tyr Gly Gln Ser Gly Tyr Arg Thr Asp Gly Thr Asn Gly
    1175                1180                1185 atg ccg tac gga cag tct ggt aat cga gca gac ggg gtg cca tac aga      3896
Met Pro Tyr Gly Gln Ser Gly Asn Arg Ala Asp Gly Val Pro Tyr Arg
1190                1195                1200                1205 caa tcc gga tat gga aca gat gga gta gcg cac gac caa cct gga tat      3944
Gln Ser Gly Tyr Gly Thr Asp Gly Val Ala His Asp Gln Pro Gly Tyr
                1210                1215                1220 cga gca gac gga gta gcg tac gaa caa tct gga tat cga gca gac gga      3992
Arg Ala Asp Gly Val Ala Tyr Glu Gln Ser Gly Tyr Arg Ala Asp Gly
            1225                1230                1235 gta acg tat gac caa tct gcc aat caa acc cgc aaa tat cat ggt tgc      4040
Val Thr Tyr Asp Gln Ser Ala Asn Gln Thr Arg Lys Tyr His Gly Cys
        1240                1245                1250 cat aca gtc gga ctg cca cat cca gag cat ggt tgt tgt tat cca gac      4088
His Thr Val Gly Leu Pro His Pro Glu His Gly Cys Cys Tyr Pro Asp
    1255                1260                1265 aga gta agc gat ggc caa cag ctt gca tat gta aca aaa tcg att gat      4136
Arg Val Ser Asp Gly Gln Gln Leu Ala Tyr Val Thr Lys Ser Ile Asp
1270                1275                1280                1285 ctg ttc ccg gat aca gat aaa gtc cgg atc gac att gga gaa acc gaa      4184
Leu Phe Pro Asp Thr Asp Lys Val Arg Ile Asp Ile Gly Glu Thr Glu
                1290                1295                1300 ggg aac ttt aga gtg gaa agt gtg gaa ttg att tgt atg gaa aag          4229
Gly Asn Phe Arg Val Glu Ser Val Glu Leu Ile Cys Met Glu Lys
            1305                1310                1315 taaatcatca caagtaaaag tatcgtttac taaaaattta ttttccaagc aacaggggag    4289
aagatgattt gggtgtaata ctcaaaccat cttttcttat aagccacttt atgatcattc    4349
gtgatcgaga                                                           4359

<210> SEQ ID NO 4
<211> LENGTH: 1316
<212> TYPE: PRT
<213> ORGANISM: Bacillus popilliae

<400> SEQUENCE: 4

Met Leu Trp Leu Asn Thr His Cys Ser Leu Ile Gly Ile Thr Gly Arg
1               5                   10                  15

Gln Thr Met Asn Gln Tyr His Asn Gln Asn Asp Asn Lys Ser Tyr Asn
            20                  25                  30

Gln Ser Gly Asn Glu Met Gln Ile Ile Gln Pro Ser Ser Asn Ala Leu
        35                  40                  45

Leu Tyr Ser Pro Asn Lys Tyr Pro Tyr Ala Thr Asp Pro Asn Val Ile
```

-continued

```
            50                  55                  60
Ala Glu Gly Gly Ser Tyr Lys Asn Trp Leu Asp Met Cys Thr Gly Thr
 65                  70                  75                  80

Gly Asp Thr Arg Ser Pro Glu Thr Ala Ala Ile Ser Lys Gly Ala Val
                 85                  90                  95

Ser Ala Ala Ile Thr Ile Ser Thr Gly Leu Leu Gly Leu Leu Gly Val
                100                 105                 110

Pro Phe Ala Ser Gln Ile Gly Ala Phe Tyr Thr Phe Leu Leu Asn Thr
                115                 120                 125

Leu Trp Pro Ala Ser Asn Thr Gln Trp Glu Gln Phe Ile Ala His Val
130                 135                 140

Glu Leu Ile Asn Ala Lys Leu Thr Asp His Val Arg Asn Ser Ala
145                 150                 155                 160

Leu Thr Lys Leu Asn Gly Leu Arg Asn Asn Ile Glu Ile Tyr Asn Glu
                165                 170                 175

Ala Leu Ile Val Trp Lys Gln Asp Pro Asn Asn Ser Lys Leu Lys Asp
                180                 185                 190

Asp Val Arg Ser Lys Phe Val Gly Leu Asn Ser Gln Phe Glu Glu Tyr
                195                 200                 205

Ile Pro Gln Phe Lys Glu Glu Gly Phe Glu Val Gln Leu Leu Thr Ile
210                 215                 220

Tyr Ala Gln Ser Ala Asn Leu His Leu Leu Leu Arg Asp Ser Ser
225                 230                 235                 240

Leu Tyr Gly Ala Ser Trp Gly Phe Ala Gln Ala Thr Ile Asp Asn Asn
                245                 250                 255

Tyr Asn Arg Gln Ile Arg Lys Thr Ala Glu Tyr Ala Asn His Cys Thr
                260                 265                 270

Thr Trp Tyr Gln Thr Gly Leu Gln Arg Leu Gln Gly Thr Thr Ala Ser
                275                 280                 285

Ser Trp Leu Ser Tyr His Arg Phe Arg Arg Glu Met Thr Leu Thr Val
                290                 295                 300

Leu Asp Ile Cys Ala Leu Phe Ser Asn Tyr Asp Ala Arg Ser Tyr Pro
305                 310                 315                 320

Leu Glu Val Arg Gly Glu Leu Thr Arg Glu Ile Tyr Thr Asp Pro Val
                325                 330                 335

Ala Pro Gly Thr Asn Trp Ile Asp Arg Ala Pro Ser Phe Ala Glu Ile
                340                 345                 350

Glu Asn Leu Val Ile Arg Ala Pro Arg Thr Val Thr Trp Ile Ser Gly
                355                 360                 365

Asp Leu Ile Val Tyr Thr Gly Arg Leu Tyr Gly Tyr Thr Gly Asn Asn
                370                 375                 380

Asp Tyr Trp Ala Ala His Arg Leu Asp Phe Leu Glu Thr Asn Gly Tyr
385                 390                 395                 400

Arg Phe Glu Gly Pro Thr Tyr Gly Ser Thr Ile Asn Ile Ser Arg Thr
                405                 410                 415

Asp Ser Ile Pro Met Asn Ser Ile Asp Val Tyr Ser Thr Thr Val Val
                420                 425                 430

Thr Val Gly Ser Ala Trp Pro Thr Gly Gly Phe Val Leu Gly Val Ala
                435                 440                 445

Ser Ala Arg Phe Phe Ser Lys Ser Pro Ser Thr Gly Leu Leu Gly Glu
                450                 455                 460

Arg Val Tyr Gln Asn Pro Val Tyr Phe Ser Ser Ser Thr Leu Thr Phe
465                 470                 475                 480
```

-continued

```
Asn Leu Pro Gly Val Asp Gln Asp Thr Pro Thr Ala Ala Asp Tyr Ser
                485                 490                 495
His Lys Leu Ser Cys Ile Thr Ala Phe Arg Thr Gly Leu Asn Gly Thr
            500                 505                 510
Val Pro Val Phe Gly Arg Tyr Ser Ala Thr Val Ser Arg Asp Asn Arg
        515                 520                 525
Ile Glu Pro Asp Lys Ile Thr Gln Ile Pro Ala Val Lys Ser Asn Ser
    530                 535                 540
Leu Asp Asn Cys Pro Val Val Arg Gly Thr Gly Phe Thr Gly Gly Asp
545                 550                 555                 560
Trp Leu Lys Thr Ser Tyr Leu Ser Val Phe Val Leu Thr Ile Thr Ser
                565                 570                 575
Ser Arg Ala Gly Gln Ser Tyr Arg Ile Arg Val Arg Tyr Ala Ala Ala
            580                 585                 590
Val Asp Leu Ile Met Ser Ile Tyr Ser Asn Asp Pro Phe Ile Ser Lys
        595                 600                 605
Gly Ile Ser Leu Thr Lys Ser Met Pro Pro Leu Thr Glu Thr Val Pro
    610                 615                 620
Tyr Glu Ala Phe Lys Phe Ala Asp Phe Gly Val Thr Phe Thr Thr Ala
625                 630                 635                 640
Thr Ala Asn Lys Arg Tyr Thr Phe Gln Phe His Thr Gly Gly Ala Ala
                645                 650                 655
Ile Ile Asp Arg Ile Glu Phe Val Pro Ile Glu Gly Ser Leu Phe Glu
            660                 665                 670
Tyr Glu Thr Lys Gln Gln Leu Glu Lys Ala Arg Lys Ala Val Asn His
        675                 680                 685
Leu Phe Thr Asp Gly Ser Lys Lys Ala Leu Lys Glu Gly Thr Thr Asp
    690                 695                 700
Tyr Glu Ile Asp Gln Ala Ala Asn Val Val Asp Cys Ile Ser Asp Glu
705                 710                 715                 720
Cys Gly His Glu Lys Met Ile Leu Leu Asp Glu Val Lys Tyr Ala Lys
                725                 730                 735
Gln Leu Ser Gln Ala Arg Asn Leu Leu Leu Asn Gly Asn Phe Asp Asp
            740                 745                 750
Leu Tyr Pro Ala Leu Glu Arg Glu Asn Pro Trp Lys Thr Ser Pro His
        755                 760                 765
Val Thr Ile Arg Gln Asp Asn Pro Ile Phe Lys Gly His Tyr Leu Ser
    770                 775                 780
Met Ala Gly Ala Asn Asp Ile Glu Ala Thr Asn Asp Thr Phe Pro Thr
785                 790                 795                 800
Tyr Val Tyr Gln Lys Ile Asp Glu Ala Lys Leu Lys Pro Tyr Thr Arg
                805                 810                 815
Tyr Lys Val Arg Gly Phe Val Gly Ser Ser Lys Ala Leu Glu Leu Leu
            820                 825                 830
Val Thr Arg Tyr Asn Glu Glu Val Asp Ala Ile Leu Asp Val Pro Asp
        835                 840                 845
Asn Ile Pro His Ala Pro Thr Pro Val Cys Gly Glu Phe Asp Arg Cys
    850                 855                 860
Lys Pro Tyr Ser Tyr Pro Pro Leu Leu Pro Glu Cys Asn Pro Glu Phe
865                 870                 875                 880
Ile Asn Gln Met Gln Pro Ser Ser Cys His His Asn Gln Met Val Asp
                885                 890                 895
```

```
Tyr Asn Asn Arg Lys His Arg Lys Cys His Gln Ala His Gln Phe Glu
            900                 905                 910

Phe His Ile Asp Thr Gly Thr Ile Asp Leu Val Glu Asp Leu Gly Ile
            915                 920                 925

Trp Val Ile Phe Lys Ile Cys Ala Thr Asp Gly Tyr Ala Ser Leu Asp
            930                 935                 940

Asp Leu Glu Val Ile Glu Glu Gly Ala Leu Gly Val Glu Ala Leu Glu
945                 950                 955                 960

Leu Val Lys Lys Arg Glu Lys Lys Trp Arg His Gln Lys Glu Gln His
            965                 970                 975

Cys Ser Gln Thr Lys His Lys Tyr Asp Ala Ala Lys His Ala Val Met
            980                 985                 990

Ala Leu Phe Thr Asn Thr Arg Tyr Glu Lys Leu Lys Phe Glu Thr Thr
            995                 1000                1005

Ile Ser Asn Ile Leu Tyr Ala Asp His Leu Val Gln Ser Ile Pro Tyr
        1010                1015                1020

Val Tyr Asn Lys Tyr Val Pro Glu Val Pro Gly Met Asn Tyr Glu Leu
1025                1030                1035                1040

Tyr Thr Glu Leu Asn Thr Leu Val Gln Asn Ala Phe Tyr Leu Tyr Asp
            1045                1050                1055

Gln Arg Asn Leu Ile Lys Asn Gly Arg Phe Ser Asn Gly Leu Met Tyr
            1060                1065                1070

Trp Gln Ala Thr Pro His Ala Arg Val Glu Gln Glu Tyr Glu Lys Ser
            1075                1080                1085

Val Leu Val Leu Pro Asn Trp Asp Ala Asn Val Ser Gln Asp Leu Cys
            1090                1095                1100

Ile Glu His Asn Arg Gly Tyr Val Leu Arg Val Thr Ala Arg Lys Glu
1105                1110                1115                1120

Asp Pro Gly Ala Gly Asn Val Thr Phe Ser Asp Cys Ala Asn His Val
            1125                1130                1135

Asp Lys Leu Ser Phe Thr Ser Cys Asp Ile Ala Thr Asn Ala Val Pro
            1140                1145                1150

Gly Ala Gln Ala Asn Asp Pro Ala Ala Gly Val Ala Tyr Gly Gln Gln
            1155                1160                1165

Gly Cys Gln Ile Asp Arg Val Pro Tyr Gly Gln Ser Gly Tyr Arg Thr
            1170                1175                1180

Asp Gly Thr Asn Gly Met Pro Tyr Gly Gln Ser Gly Asn Arg Ala Asp
1185                1190                1195                1200

Gly Val Pro Tyr Arg Gln Ser Gly Tyr Gly Thr Asp Gly Val Ala His
            1205                1210                1215

Asp Gln Pro Gly Tyr Arg Ala Asp Gly Val Ala Tyr Glu Gln Ser Gly
            1220                1225                1230

Tyr Arg Ala Asp Gly Val Thr Tyr Asp Gln Ser Ala Asn Gln Thr Arg
            1235                1240                1245

Lys Tyr His Gly Cys His Thr Val Gly Leu Pro His Pro Glu His Gly
            1250                1255                1260

Cys Cys Tyr Pro Asp Arg Val Ser Asp Gly Gln Gln Leu Ala Tyr Val
1265                1270                1275                1280

Thr Lys Ser Ile Asp Leu Phe Pro Asp Thr Asp Lys Val Arg Ile Asp
            1285                1290                1295

Ile Gly Glu Thr Glu Gly Asn Phe Arg Val Glu Ser Val Glu Leu Ile
            1300                1305                1310

Cys Met Glu Lys
```

-continued

```
                                                1315

<210> SEQ ID NO 5
<211> LENGTH: 4188
<212> TYPE: DNA
<213> ORGANISM: Bacillus popilliae
<220> FEATURE:
<221> NAME/KEY: CDS
<222> LOCATION: (1)..(4158)

<400> SEQUENCE: 5 atg ttg tgg cta aat act cat tgt tca tta ata gaa ata act ggg agg        48
Met Leu Trp Leu Asn Thr His Cys Ser Leu Ile Glu Ile Thr Gly Arg
 1               5                  10                  15 caa act atg aat caa tat cat aac caa aac gat aac aaa agt tac aac        96
Gln Thr Met Asn Gln Tyr His Asn Gln Asn Asp Asn Lys Ser Tyr Asn
             20                  25                  30 caa agt gga aat gaa gtg caa att ata caa cct tca agt aac gct tta       144
Gln Ser Gly Asn Glu Val Gln Ile Ile Gln Pro Ser Ser Asn Ala Leu
         35                  40                  45 ctt tac agt ccc aac aag tat ccg tat gct acg gat ccc aat gtc ata       192
Leu Tyr Ser Pro Asn Lys Tyr Pro Tyr Ala Thr Asp Pro Asn Val Ile
     50                  55                  60 gca gag ggt aga agt tat aaa aat tgg ttg gat atg tgt gta ggt gta       240
Ala Glu Gly Arg Ser Tyr Lys Asn Trp Leu Asp Met Cys Val Gly Val
 65                  70                  75                  80 ggt gac gat aca cga agt ccc gaa gct cgg gtt act gca caa agt tct       288
Gly Asp Asp Thr Arg Ser Pro Glu Ala Arg Val Thr Ala Gln Ser Ser
                 85                  90                  95 att tcg act tct ctt ggt ata acc agc aca atc att ggc gct cta ggt       336
Ile Ser Thr Ser Leu Gly Ile Thr Ser Thr Ile Ile Gly Ala Leu Gly
            100                 105                 110 att ccg gtt gta ggc gaa gcc att gga att ttc ggc gca cta ttg gat       384
Ile Pro Val Val Gly Glu Ala Ile Gly Ile Phe Gly Ala Leu Leu Asp
        115                 120                 125 tgg ttg tgg cct gca ggc gct gat cca tgg gta ata ttt atg aat cat       432
Trp Leu Trp Pro Ala Gly Ala Asp Pro Trp Val Ile Phe Met Asn His
    130                 135                 140 gta gaa gaa ctc ata aat tca aaa ata aca gag act gta aaa aat gag       480
Val Glu Glu Leu Ile Asn Ser Lys Ile Thr Glu Thr Val Lys Asn Glu
145                 150                 155                 160 gca att aca aga tta gac ggt tta ggc aat gtc cta gcg cta tat caa       528
Ala Ile Thr Arg Leu Asp Gly Leu Gly Asn Val Leu Ala Leu Tyr Gln
                165                 170                 175 aag gct ttc gaa gaa tgg caa caa cat cct act ctt gaa tca gct cga       576
Lys Ala Phe Glu Glu Trp Gln Gln His Pro Thr Leu Glu Ser Ala Arg
            180                 185                 190 cta cgt gta aca gat gat ttt tct aat gta aat aaa ttt ttt gag gca       624
Leu Arg Val Thr Asp Asp Phe Ser Asn Val Asn Lys Phe Phe Glu Ala
        195                 200                 205 ttt atg cct tca ttc aga gta cca ggt tat gaa gta cca tta tta agc       672
Phe Met Pro Ser Phe Arg Val Pro Gly Tyr Glu Val Pro Leu Leu Ser
    210                 215                 220 gta tac gta tcc gct gca aac ctc cat tta tta tta aga gat agc       720
Val Tyr Val Ser Ala Ala Asn Leu His Leu Leu Leu Arg Asp Ser
225                 230                 235                 240 tcg att ttc ggt ttg gat tgg gga tta agt caa act cat gtt aac gat       768
Ser Ile Phe Gly Leu Asp Trp Gly Leu Ser Gln Thr His Val Asn Asp
                245                 250                 255 aat tat aat ctc caa ata agg cgc tct gca gat tat gca aat cat tgt       816
Asn Tyr Asn Leu Gln Ile Arg Arg Ser Ala Asp Tyr Ala Asn His Cys
```

-continued

|  | 260 |  |  |  | 265 |  |  |  | 270 |  |  |  |  |
|---|---|---|---|---|---|---|---|---|---|---|---|---|---|
| aca | act | tgg | tat | cgg | acg | ggt | tta | caa | aga | ttg | caa | ggc | acc | aat | gct | 864 |
| Thr | Thr | Trp | Tyr | Arg | Thr | Gly | Leu | Gln | Arg | Leu | Gln | Gly | Thr | Asn | Ala |  |
|  | 275 |  |  |  | 280 |  |  |  | 285 |  |  |  |  |

| agc | agt | tgg | gtc | aat | tat | aat | cga | ttt | aga | aga | gaa | atg | aca | cta | act | 912 |
| Ser | Ser | Trp | Val | Asn | Tyr | Asn | Arg | Phe | Arg | Arg | Glu | Met | Thr | Leu | Thr |
| 290 |  |  |  | 295 |  |  |  | 300 |

| gta | tta | gat | gtt | tgt | gca | tta | ttt | tca | agt | tat | gat | tat | cgt | agt | tac | 960 |
| Val | Leu | Asp | Val | Cys | Ala | Leu | Phe | Ser | Ser | Tyr | Asp | Tyr | Arg | Ser | Tyr |
|  | 305 |  |  |  | 310 |  |  |  | 315 |  |  |  | 320 |

| cca | atg | gag | cta | agg | gga | gag | ctt | acg | aga | gaa | att | tat | acg | gat | cca | 1008 |
| Pro | Met | Glu | Leu | Arg | Gly | Glu | Leu | Thr | Arg | Glu | Ile | Tyr | Thr | Asp | Pro |
|  |  |  |  | 325 |  |  |  | 330 |  |  |  | 335 |

| gta | gga | gcc | tct | ttt | tgg | gtg | aat | aga | gca | cca | aac | ttc | gca | tca | ata | 1056 |
| Val | Gly | Ala | Ser | Phe | Trp | Val | Asn | Arg | Ala | Pro | Asn | Phe | Ala | Ser | Ile |
|  |  | 340 |  |  |  | 345 |  |  |  | 350 |

| gaa | aat | aca | gta | gtt | agg | caa | cca | cac | ccc | ttt | act | tgg | cta | gtt | act | 1104 |
| Glu | Asn | Thr | Val | Val | Arg | Gln | Pro | His | Pro | Phe | Thr | Trp | Leu | Val | Thr |
|  | 355 |  |  |  | 360 |  |  |  | 365 |

| tta | aca | gtt | aat | aca | ggt | caa | gtg | aga | tct | ggc | gat | gga | aat | tct | aac | 1152 |
| Leu | Thr | Val | Asn | Thr | Gly | Gln | Val | Arg | Ser | Gly | Asp | Gly | Asn | Ser | Asn |
| 370 |  |  |  | 375 |  |  |  | 380 |

| tat | tat | tgg | aaa | tca | cat | agt | caa | acc | gtg | agt | gaa | acc | gga | ggg | tca | 1200 |
| Tyr | Tyr | Trp | Lys | Ser | His | Ser | Gln | Thr | Val | Ser | Glu | Thr | Gly | Gly | Ser |
| 385 |  |  |  | 390 |  |  |  | 395 |  |  |  | 400 |

| ggt | cct | att | cag | agt | cct | acc | tgt | gga | agt | act | ggt | aca | att | tat | cgc | 1248 |
| Gly | Pro | Ile | Gln | Ser | Pro | Thr | Cys | Gly | Ser | Thr | Gly | Thr | Ile | Tyr | Arg |
|  |  |  |  | 405 |  |  |  | 410 |  |  |  | 415 |

| acg | gat | aat | tta | ctt | ttt | aat | cca | ttt | tta | tta | ggt | gat | att | tat | acc | 1296 |
| Thr | Asp | Asn | Leu | Leu | Phe | Asn | Pro | Phe | Leu | Leu | Gly | Asp | Ile | Tyr | Thr |
|  |  | 420 |  |  |  | 425 |  |  |  | 430 |

| att | aat | aca | ggt | tat | gtt | tct | tat | ctg | gct | aat | ttg | ttt | gga | atc | tat | 1344 |
| Ile | Asn | Thr | Gly | Tyr | Val | Ser | Tyr | Leu | Ala | Asn | Leu | Phe | Gly | Ile | Tyr |
|  | 435 |  |  |  | 440 |  |  |  | 445 |

| tca | gct | aga | ttt | acg | acg | act | cgt | tct | att | gag | ctt | ctg | tat | gag | aac | 1392 |
| Ser | Ala | Arg | Phe | Thr | Thr | Thr | Arg | Ser | Ile | Glu | Leu | Leu | Tyr | Glu | Asn |
| 450 |  |  |  | 455 |  |  |  | 460 |

| caa | aga | gtt | ttc | cca | gcc | tac | aat | cat | caa | att | cgt | gaa | tta | cct | gga | 1440 |
| Gln | Arg | Val | Phe | Pro | Ala | Tyr | Asn | His | Gln | Ile | Arg | Glu | Leu | Pro | Gly |
| 465 |  |  |  | 470 |  |  |  | 475 |  |  |  | 480 |

| gta | aac | tcg | gat | agg | cca | act | gct | gcc | gac | tat | agt | cat | aga | cta | tcg | 1488 |
| Val | Asn | Ser | Asp | Arg | Pro | Thr | Ala | Ala | Asp | Tyr | Ser | His | Arg | Leu | Ser |
|  |  |  | 485 |  |  |  | 490 |  |  |  | 495 |

| tat | atc | tca | ggt | ttt | gca | act | gat | gtg | gga | gga | acg | gtt | cta | gtt | tat | 1536 |
| Tyr | Ile | Ser | Gly | Phe | Ala | Thr | Asp | Val | Gly | Gly | Thr | Val | Leu | Val | Tyr |
|  |  | 500 |  |  |  | 505 |  |  |  | 510 |

| ggg | tgg | aca | tct | tca | act | gct | act | cgt | gag | aat | aat | att | acg | cta | gac | 1584 |
| Gly | Trp | Thr | Ser | Ser | Thr | Ala | Thr | Arg | Glu | Asn | Asn | Ile | Thr | Leu | Asp |
|  | 515 |  |  |  | 520 |  |  |  | 525 |

| gac | aga | ata | gta | caa | ctt | cca | gct | gtt | aag | gga | aca | agt | ctc | aac | aat | 1632 |
| Asp | Arg | Ile | Val | Gln | Leu | Pro | Ala | Val | Lys | Gly | Thr | Ser | Leu | Asn | Asn |
| 530 |  |  |  | 535 |  |  |  | 540 |

| tgc | caa | gta | gtt | aga | gga | act | gga | ttt | aca | gga | gga | gac | tgg | ttg | aag | 1680 |
| Cys | Gln | Val | Val | Arg | Gly | Thr | Gly | Phe | Thr | Gly | Gly | Asp | Trp | Leu | Lys |
| 545 |  |  |  | 550 |  |  |  | 555 |  |  |  | 560 |

| cct | aat | aat | aat | ggt | aca | ttt | tct | cta | gct | ctt | ggt | ttc | agg | tcg | act | 1728 |
| Pro | Asn | Asn | Asn | Gly | Thr | Phe | Ser | Leu | Ala | Leu | Gly | Phe | Arg | Ser | Thr |
|  |  |  | 565 |  |  |  | 570 |  |  |  | 575 |

| tac | act | tac | cgc | ctc | cgc | att | cgt | tat | gct | gcc | gca | gca | ggc | gga | tca | 1776 |

```
Tyr Thr Tyr Arg Leu Arg Ile Arg Tyr Ala Ala Ala Gly Gly Ser
            580                 585                 590 ggt ttt tct ctt gtt ata tcg gat caa tat gga gaa ttt cca acc aca   1824
Gly Phe Ser Leu Val Ile Ser Asp Gln Tyr Gly Glu Phe Pro Thr Thr
        595                 600                 605 aca gta tcg ctt tcc tcc aca atg tac tca ctg ccc caa aat gta cca   1872
Thr Val Ser Leu Ser Ser Thr Met Tyr Ser Leu Pro Gln Asn Val Pro
    610                 615                 620 tac gag gct ttt aag att gta gat tta cct tct act gtt act att aga   1920
Tyr Glu Ala Phe Lys Ile Val Asp Leu Pro Ser Thr Val Thr Ile Arg
625                 630                 635                 640 aat act tct cct gct tca aca act ttt cga ctt gat ttc cgt ttc att   1968
Asn Thr Ser Pro Ala Ser Thr Thr Phe Arg Leu Asp Phe Arg Phe Ile
                645                 650                 655 gtg cca tta gga ata ctc gca aat ata tta att gac cga att gaa ttt   2016
Val Pro Leu Gly Ile Leu Ala Asn Ile Leu Ile Asp Arg Ile Glu Phe
            660                 665                 670 gtt ccc att gag ggt tcc ttg ttc gag tac gaa acc aaa cag cag cta   2064
Val Pro Ile Glu Gly Ser Leu Phe Glu Tyr Glu Thr Lys Gln Gln Leu
        675                 680                 685 gaa aaa gca agg aaa gcg gtg aac cat ttg ttt aca gat gga tcg aaa   2112
Glu Lys Ala Arg Lys Ala Val Asn His Leu Phe Thr Asp Gly Ser Lys
    690                 695                 700 aag gcg cta aaa gaa ggc acg aca gat tat gag atc gat caa gcc gcc   2160
Lys Ala Leu Lys Glu Gly Thr Thr Asp Tyr Glu Ile Asp Gln Ala Ala
705                 710                 715                 720 aac gtg gtg gat tgt ata tcg gat gag tgt gga cat gag aaa atg atc   2208
Asn Val Val Asp Cys Ile Ser Asp Glu Cys Gly His Glu Lys Met Ile
                725                 730                 735 ctg ttg gat gaa gtg aaa tat gca aaa caa ctc agc caa gcc cgc aat   2256
Leu Leu Asp Glu Val Lys Tyr Ala Lys Gln Leu Ser Gln Ala Arg Asn
            740                 745                 750 tta ctg ctc aat ggg aat ttc gat gat cta tat cca gct ctg gag agg   2304
Leu Leu Leu Asn Gly Asn Phe Asp Asp Leu Tyr Pro Ala Leu Glu Arg
        755                 760                 765 gag aat cca tgg aaa aca agc ccg aat gtt acg atc cgt caa gat aac   2352
Glu Asn Pro Trp Lys Thr Ser Pro Asn Val Thr Ile Arg Gln Asp Asn
    770                 775                 780 ccg att ttt aaa ggc cat tat ctc agt atg gcg ggt gcg aac gat atc   2400
Pro Ile Phe Lys Gly His Tyr Leu Ser Met Ala Gly Ala Asn Asp Ile
785                 790                 795                 800 gag gcc acc aat gat acc ttc ccc acg tat gcc tat caa aaa ata gac   2448
Glu Ala Thr Asn Asp Thr Phe Pro Thr Tyr Ala Tyr Gln Lys Ile Asp
                805                 810                 815 gaa gcc aaa tta aag ccg tat aca cgt tat aaa gtg cgc ggg ttt gtt   2496
Glu Ala Lys Leu Lys Pro Tyr Thr Arg Tyr Lys Val Arg Gly Phe Val
            820                 825                 830 ggc agc agc aaa gct cta gag ctg ttg gtt aca cgc tat aat gaa gaa   2544
Gly Ser Ser Lys Ala Leu Glu Leu Leu Val Thr Arg Tyr Asn Glu Glu
        835                 840                 845 gtc gat gcg att tta gat gta ccg gat aat atc ccg cat gcg ccg ata   2592
Val Asp Ala Ile Leu Asp Val Pro Asp Asn Ile Pro His Ala Pro Ile
    850                 855                 860 cct gtc tgc ggt gaa ttt gat cga tgc aag ccc tat tcg tat cca cct   2640
Pro Val Cys Gly Glu Phe Asp Arg Cys Lys Pro Tyr Ser Tyr Pro Pro
865                 870                 875                 880 tta ctt cca gaa tgt aac cct gag ttt ata aat cag atg caa cca tcc   2688
Leu Leu Pro Glu Cys Asn Pro Glu Phe Ile Asn Gln Met Gln Pro Ser
                885                 890                 895
```

```
                                                       -continued tct tgc cac cac act cag atg gtc gat tac aat aac atg aac atg agc         2736
Ser Cys His His Thr Gln Met Val Asp Tyr Asn Asn Met Asn Met Ser
            900                 905                 910 acg agt act acc atg aat cct acc ctt acg cct gaa ata gca tcc agc         2784
Thr Ser Thr Thr Met Asn Pro Thr Leu Thr Pro Glu Ile Ala Ser Ser
        915                 920                 925 caa agt gga ttc ggc aga aaa cat cgc aaa tgt cat caa gcg cat caa         2832
Gln Ser Gly Phe Gly Arg Lys His Arg Lys Cys His Gln Ala His Gln
    930                 935                 940 ttt gag ttc cat att gat acc ggg aca atc gat ctg gtc gaa gat ttg         2880
Phe Glu Phe His Ile Asp Thr Gly Thr Ile Asp Leu Val Glu Asp Leu
945                 950                 955                 960 ggc att tgg gtg atc ttc aaa atc tgt gcc aca gat ggt tac gca agc         2928
Gly Ile Trp Val Ile Phe Lys Ile Cys Ala Thr Asp Gly Tyr Ala Ser
                965                 970                 975 tta gat gat ttg gaa gtg att gaa gaa gga gcg ctg ggt gtc gaa gca         2976
Leu Asp Asp Leu Glu Val Ile Glu Glu Gly Ala Leu Gly Val Glu Ala
            980                 985                 990 tta gaa ctt gtc aag aaa aga gaa aag aaa tgg aga cat cag aag gag         3024
Leu Glu Leu Val Lys Lys Arg Glu Lys Lys Trp Arg His Gln Lys Glu
        995                 1000                1005 cag cac tgt tcg caa acg aaa cac aaa tat gat gcg gcc aaa cat gcg         3072
Gln His Cys Ser Gln Thr Lys His Lys Tyr Asp Ala Ala Lys His Ala
    1010                1015                1020 gtg atg gcg tta ttt aca aac acg cgc tat gaa aaa ttg aag ttc gaa         3120
Val Met Ala Leu Phe Thr Asn Thr Arg Tyr Glu Lys Leu Lys Phe Glu
1025                1030                1035                1040 aca acc att tct gac att ttg tat gct gat cat ctc gtg cag tcg atc         3168
Thr Thr Ile Ser Asp Ile Leu Tyr Ala Asp His Leu Val Gln Ser Ile
                1045                1050                1055 cct tat gta tat aat aaa tat gta ccg gaa gtt cca ggt atg aat tac         3216
Pro Tyr Val Tyr Asn Lys Tyr Val Pro Glu Val Pro Gly Met Asn Tyr
            1060                1065                1070 gaa ctc tat tca gag cta aac aca ctg gtt cag aat gcg ttc tac ctg         3264
Glu Leu Tyr Ser Glu Leu Asn Thr Leu Val Gln Asn Ala Phe Tyr Leu
        1075                1080                1085 tat gac cag cgg aat ctg att aaa aat ggg cgc ttt agc aat ggg ctt         3312
Tyr Asp Gln Arg Asn Leu Ile Lys Asn Gly Arg Phe Ser Asn Gly Leu
    1090                1095                1100 atg cat tgg caa gct act cct cat gca aga gta gag caa gaa cat gag         3360
Met His Trp Gln Ala Thr Pro His Ala Arg Val Glu Gln Glu His Glu
1105                1110                1115                1120 aaa tcg gtg ctc gtg ctg cca aat tgg gat gcc aat gtg tcg caa gat         3408
Lys Ser Val Leu Val Leu Pro Asn Trp Asp Ala Asn Val Ser Gln Asp
                1125                1130                1135 ctt tgt atc gaa cac aat cgc ggt tat gta ttg cgt gtc acg gcg aga         3456
Leu Cys Ile Glu His Asn Arg Gly Tyr Val Leu Arg Val Thr Ala Arg
            1140                1145                1150 aaa gaa gat ccg gga gcc ggc aat gtt acc ttt agt gac tgt gca aat         3504
Lys Glu Asp Pro Gly Ala Gly Asn Val Thr Phe Ser Asp Cys Ala Asn
        1155                1160                1165 cat gtc aac aag ctg agc ttt act tct tgc gat ata gct aca aac gca         3552
His Val Asn Lys Leu Ser Phe Thr Ser Cys Asp Ile Ala Thr Asn Ala
    1170                1175                1180 gtg cca ggt gcc caa gcg aat gat cca gcc gcc gga gta gcc tat gga         3600
Val Pro Gly Ala Gln Ala Asn Asp Pro Ala Ala Gly Val Ala Tyr Gly
1185                1190                1195                1200 caa cag ggt tgt caa ata gat aga gtg ccg tac ggg caa tct gga tat         3648
Gln Gln Gly Cys Gln Ile Asp Arg Val Pro Tyr Gly Gln Ser Gly Tyr
                1205                1210                1215
```

```
aga aca gac gga aca aat gga atg ccg tac ggg cag tct ggt aat cga    3696
Arg Thr Asp Gly Thr Asn Gly Met Pro Tyr Gly Gln Ser Gly Asn Arg
            1220                1225                1230 gcg gac ggg gtg cca tac aga caa tcc gga tat gga aca gat gga gta    3744
Ala Asp Gly Val Pro Tyr Arg Gln Ser Gly Tyr Gly Thr Asp Gly Val
        1235                1240                1245 gcg cac gac caa cct gga tat cga gca gac gga gca gcg tac gaa cag    3792
Ala His Asp Gln Pro Gly Tyr Arg Ala Asp Gly Ala Ala Tyr Glu Gln
    1250                1255                1260 tct ggt cat cga gca gac gga gta gcg tac gaa caa tct gga tat cga    3840
Ser Gly His Arg Ala Asp Gly Val Ala Tyr Glu Gln Ser Gly Tyr Arg
1265                1270                1275                1280 gca ggt gga gta gcg tac gaa cag tct ggt cat cga gca gat gga gtg    3888
Ala Gly Gly Val Ala Tyr Glu Gln Ser Gly His Arg Ala Asp Gly Val
                1285                1290                1295 ccg tac gga caa tct gga tat gga aca gac gga gta acg tac gac caa    3936
Pro Tyr Gly Gln Ser Gly Tyr Gly Thr Asp Gly Val Thr Tyr Asp Gln
            1300                1305                1310 tct gtc aaa caa acc cgc aaa tac cat ggt tgc cat aca gac ggg ctg    3984
Ser Val Lys Gln Thr Arg Lys Tyr His Gly Cys His Thr Asp Gly Leu
        1315                1320                1325 cca cat cca gag cat ggt tgt tgt tat cca gac aga gta agc gat ggc    4032
Pro His Pro Glu His Gly Cys Cys Tyr Pro Asp Arg Val Ser Asp Gly
    1330                1335                1340 caa cag ctt gca tat gta aca aaa tcg att gat ctg ttc ccg gat aca    4080
Gln Gln Leu Ala Tyr Val Thr Lys Ser Ile Asp Leu Phe Pro Asp Thr
1345                1350                1355                1360 gat aaa gtc cgg atc gac att gga gaa acc gaa ggg aac ttt aga gtg    4128
Asp Lys Val Arg Ile Asp Ile Gly Glu Thr Glu Gly Asn Phe Arg Val
                1365                1370                1375 gaa agt gtg gaa ttg att tgt atg gaa aag taaatcatca caagtaaaag       4178
Glu Ser Val Glu Leu Ile Cys Met Glu Lys
            1380                1385 tatcgtttac                                                          4188

<210> SEQ ID NO 6
<211> LENGTH: 1386
<212> TYPE: PRT
<213> ORGANISM: Bacillus popilliae

<400> SEQUENCE: 6

Met Leu Trp Leu Asn Thr His Cys Ser Leu Ile Glu Ile Thr Gly Arg
  1               5                  10                  15

Gln Thr Met Asn Gln Tyr His Asn Gln Asn Asp Asn Lys Ser Tyr Asn
             20                  25                  30

Gln Ser Gly Asn Glu Val Gln Ile Ile Gln Pro Ser Ser Asn Ala Leu
         35                  40                  45

Leu Tyr Ser Pro Asn Lys Tyr Pro Tyr Ala Thr Asp Pro Asn Val Ile
     50                  55                  60

Ala Glu Gly Arg Ser Tyr Lys Asn Trp Leu Asp Met Cys Val Gly Val
 65                  70                  75                  80

Gly Asp Asp Thr Arg Ser Pro Glu Ala Arg Val Thr Ala Gln Ser Ser
                 85                  90                  95

Ile Ser Thr Ser Leu Gly Ile Thr Ser Thr Ile Ile Gly Ala Leu Gly
            100                 105                 110

Ile Pro Val Val Gly Glu Ala Ile Gly Ile Phe Gly Ala Leu Leu Asp
        115                 120                 125
```

```
Trp Leu Trp Pro Ala Gly Ala Asp Pro Trp Val Ile Phe Met Asn His
    130                 135                 140

Val Glu Glu Leu Ile Asn Ser Lys Ile Thr Glu Thr Val Lys Asn Glu
145                 150                 155                 160

Ala Ile Thr Arg Leu Asp Gly Leu Gly Asn Val Leu Ala Leu Tyr Gln
                165                 170                 175

Lys Ala Phe Glu Glu Trp Gln Gln His Pro Thr Leu Glu Ser Ala Arg
            180                 185                 190

Leu Arg Val Thr Asp Asp Phe Ser Asn Val Asn Lys Phe Glu Ala
        195                 200                 205

Phe Met Pro Ser Phe Arg Val Pro Gly Tyr Glu Val Pro Leu Leu Ser
210                 215                 220

Val Tyr Val Ser Ala Ala Asn Leu His Leu Leu Leu Arg Asp Ser
225                 230                 235                 240

Ser Ile Phe Gly Leu Asp Trp Gly Leu Ser Gln Thr His Val Asn Asp
                245                 250                 255

Asn Tyr Asn Leu Gln Ile Arg Arg Ser Ala Asp Tyr Ala Asn His Cys
            260                 265                 270

Thr Thr Trp Tyr Arg Thr Gly Leu Gln Arg Leu Gln Gly Thr Asn Ala
        275                 280                 285

Ser Ser Trp Val Asn Tyr Asn Arg Phe Arg Arg Glu Met Thr Leu Thr
290                 295                 300

Val Leu Asp Val Cys Ala Leu Phe Ser Ser Tyr Asp Tyr Arg Ser Tyr
305                 310                 315                 320

Pro Met Glu Leu Arg Gly Glu Leu Thr Arg Glu Ile Tyr Thr Asp Pro
                325                 330                 335

Val Gly Ala Ser Phe Trp Val Asn Arg Ala Pro Asn Phe Ala Ser Ile
            340                 345                 350

Glu Asn Thr Val Val Arg Gln Pro His Pro Phe Thr Trp Leu Val Thr
        355                 360                 365

Leu Thr Val Asn Thr Gly Gln Val Arg Ser Gly Asp Gly Asn Ser Asn
370                 375                 380

Tyr Tyr Trp Lys Ser His Ser Gln Thr Val Ser Glu Thr Gly Gly Ser
385                 390                 395                 400

Gly Pro Ile Gln Ser Pro Thr Cys Gly Ser Thr Gly Thr Ile Tyr Arg
                405                 410                 415

Thr Asp Asn Leu Leu Phe Asn Pro Phe Leu Leu Gly Asp Ile Tyr Thr
            420                 425                 430

Ile Asn Thr Gly Tyr Val Ser Tyr Leu Ala Asn Leu Phe Gly Ile Tyr
        435                 440                 445

Ser Ala Arg Phe Thr Thr Thr Arg Ser Ile Glu Leu Leu Tyr Glu Asn
450                 455                 460

Gln Arg Val Phe Pro Ala Tyr Asn His Gln Ile Arg Glu Leu Pro Gly
465                 470                 475                 480

Val Asn Ser Asp Arg Pro Thr Ala Ala Asp Tyr Ser His Arg Leu Ser
                485                 490                 495

Tyr Ile Ser Gly Phe Ala Thr Asp Val Gly Gly Thr Val Leu Val Tyr
            500                 505                 510

Gly Trp Thr Ser Thr Ala Thr Arg Glu Asn Asn Ile Thr Leu Asp
        515                 520                 525

Asp Arg Ile Val Gln Leu Pro Ala Val Lys Gly Thr Ser Leu Asn Asn
530                 535                 540

Cys Gln Val Val Arg Gly Thr Gly Phe Thr Gly Gly Asp Trp Leu Lys
```

```
                        545                 550                 555                 560

Pro Asn Asn Gly Thr Phe Ser Leu Ala Leu Gly Phe Arg Ser Thr
                            565                 570                 575

Tyr Thr Tyr Arg Leu Arg Ile Arg Tyr Ala Ala Ala Gly Gly Ser
                        580                 585                 590

Gly Phe Ser Leu Val Ile Ser Asp Gln Tyr Gly Glu Phe Pro Thr Thr
                        595                 600                 605

Thr Val Ser Leu Ser Ser Thr Met Tyr Ser Leu Pro Gln Asn Val Pro
                        610                 615                 620

Tyr Glu Ala Phe Lys Ile Val Asp Leu Pro Ser Thr Val Thr Ile Arg
            625                 630                 635                 640

Asn Thr Ser Pro Ala Ser Thr Thr Phe Arg Leu Asp Phe Arg Phe Ile
                            645                 650                 655

Val Pro Leu Gly Ile Leu Ala Asn Ile Leu Ile Asp Arg Ile Glu Phe
                        660                 665                 670

Val Pro Ile Glu Gly Ser Leu Phe Glu Tyr Glu Thr Lys Gln Gln Leu
                        675                 680                 685

Glu Lys Ala Arg Lys Ala Val Asn His Leu Phe Thr Asp Gly Ser Lys
                        690                 695                 700

Lys Ala Leu Lys Glu Gly Thr Thr Asp Tyr Glu Ile Asp Gln Ala Ala
            705                 710                 715                 720

Asn Val Val Asp Cys Ile Ser Asp Glu Cys Gly His Glu Lys Met Ile
                            725                 730                 735

Leu Leu Asp Glu Val Lys Tyr Ala Lys Gln Leu Ser Gln Ala Arg Asn
                        740                 745                 750

Leu Leu Leu Asn Gly Asn Phe Asp Asp Leu Tyr Pro Ala Leu Glu Arg
                        755                 760                 765

Glu Asn Pro Trp Lys Thr Ser Pro Asn Val Thr Ile Arg Gln Asp Asn
                        770                 775                 780

Pro Ile Phe Lys Gly His Tyr Leu Ser Met Ala Gly Ala Asn Asp Ile
            785                 790                 795                 800

Glu Ala Thr Asn Asp Thr Phe Pro Thr Tyr Ala Tyr Gln Lys Ile Asp
                            805                 810                 815

Glu Ala Lys Leu Lys Pro Tyr Thr Arg Tyr Lys Val Arg Gly Phe Val
                        820                 825                 830

Gly Ser Ser Lys Ala Leu Glu Leu Leu Val Thr Arg Tyr Asn Glu Glu
                        835                 840                 845

Val Asp Ala Ile Leu Asp Val Pro Asp Asn Ile Pro His Ala Pro Ile
            850                 855                 860

Pro Val Cys Gly Glu Phe Asp Arg Cys Lys Pro Tyr Ser Tyr Pro Pro
            865                 870                 875                 880

Leu Leu Pro Glu Cys Asn Pro Glu Phe Ile Asn Gln Met Gln Pro Ser
                            885                 890                 895

Ser Cys His His Thr Gln Met Val Asp Tyr Asn Asn Met Asn Met Ser
                        900                 905                 910

Thr Ser Thr Thr Met Asn Pro Thr Leu Thr Pro Glu Ile Ala Ser Ser
                        915                 920                 925

Gln Ser Gly Phe Gly Arg Lys His Arg Lys Cys His Gln Ala His Gln
                        930                 935                 940

Phe Glu Phe His Ile Asp Thr Gly Thr Ile Asp Leu Val Glu Asp Leu
            945                 950                 955                 960

Gly Ile Trp Val Ile Phe Lys Ile Cys Ala Thr Asp Gly Tyr Ala Ser
                            965                 970                 975
```

```
Leu Asp Asp Leu Glu Val Ile Glu Glu Gly Ala Leu Gly Val Glu Ala
            980                 985                 990

Leu Glu Leu Val Lys Lys Arg Glu Lys Lys Trp Arg His Gln Lys Glu
            995                 1000                1005

Gln His Cys Ser Gln Thr Lys His Lys Tyr Asp Ala Ala Lys His Ala
        1010                1015                1020

Val Met Ala Leu Phe Thr Asn Thr Arg Tyr Glu Lys Leu Lys Phe Glu
1025                1030                1035                1040

Thr Thr Ile Ser Asp Ile Leu Tyr Ala Asp His Leu Val Gln Ser Ile
            1045                1050                1055

Pro Tyr Val Tyr Asn Lys Tyr Val Pro Glu Val Pro Gly Met Asn Tyr
            1060                1065                1070

Glu Leu Tyr Ser Glu Leu Asn Thr Leu Val Gln Asn Ala Phe Tyr Leu
            1075                1080                1085

Tyr Asp Gln Arg Asn Leu Ile Lys Asn Gly Arg Phe Ser Asn Gly Leu
            1090                1095                1100

Met His Trp Gln Ala Thr Pro His Ala Arg Val Glu Gln Glu His Glu
1105                1110                1115                1120

Lys Ser Val Leu Val Leu Pro Asn Trp Asp Ala Asn Val Ser Gln Asp
            1125                1130                1135

Leu Cys Ile Glu His Asn Arg Gly Tyr Val Leu Arg Val Thr Ala Arg
            1140                1145                1150

Lys Glu Asp Pro Gly Ala Gly Asn Val Thr Phe Ser Asp Cys Ala Asn
            1155                1160                1165

His Val Asn Lys Leu Ser Phe Thr Ser Cys Asp Ile Ala Thr Asn Ala
    1170                1175                1180

Val Pro Gly Ala Gln Ala Asn Asp Pro Ala Ala Gly Val Ala Tyr Gly
1185                1190                1195                1200

Gln Gln Gly Cys Gln Ile Asp Arg Val Pro Tyr Gly Gln Ser Gly Tyr
            1205                1210                1215

Arg Thr Asp Gly Thr Asn Gly Met Pro Tyr Gly Gln Ser Gly Asn Arg
            1220                1225                1230

Ala Asp Gly Val Pro Tyr Arg Gln Ser Gly Tyr Gly Thr Asp Gly Val
            1235                1240                1245

Ala His Asp Gln Pro Gly Tyr Arg Ala Asp Gly Ala Ala Tyr Glu Gln
            1250                1255                1260

Ser Gly His Arg Ala Asp Gly Val Ala Tyr Glu Gln Ser Gly Tyr Arg
1265                1270                1275                1280

Ala Gly Gly Val Ala Tyr Glu Gln Ser Gly His Arg Ala Asp Gly Val
            1285                1290                1295

Pro Tyr Gly Gln Ser Gly Tyr Gly Thr Asp Gly Val Thr Tyr Asp Gln
            1300                1305                1310

Ser Val Lys Gln Thr Arg Lys Tyr His Gly Cys His Thr Asp Gly Leu
            1315                1320                1325

Pro His Pro Glu His Gly Cys Cys Tyr Pro Asp Arg Val Ser Asp Gly
            1330                1335                1340

Gln Gln Leu Ala Tyr Val Thr Lys Ser Ile Asp Leu Phe Pro Asp Thr
1345                1350                1355                1360

Asp Lys Val Arg Ile Asp Ile Gly Glu Thr Glu Gly Asn Phe Arg Val
            1365                1370                1375

Glu Ser Val Glu Leu Ile Cys Met Glu Lys
            1380                1385
```

-continued

<210> SEQ ID NO 7
<211> LENGTH: 795
<212> TYPE: DNA
<213> ORGANISM: Bacillus popilliae
<220> FEATURE:
<221> NAME/KEY: CDS
<222> LOCATION: (1)..(795)

<400> SEQUENCE: 7

| | | | | | | | | | | | | | | | | |
|---|---|---|---|---|---|---|---|---|---|---|---|---|---|---|---|---|
| caa | tat | cat | aac | caa | aac | gat | aac | aaa | agt | tac | aac | caa | agt | gga | aat | 48 |
| Gln | Tyr | His | Asn | Gln | Asn | Asp | Asn | Lys | Ser | Tyr | Asn | Gln | Ser | Gly | Asn | |
| 1 | | | | 5 | | | | | 10 | | | | | 15 | | |
| gac | atg | caa | att | ata | caa | cct | tca | agt | aac | gct | tta | ctt | tac | agt | ccc | 96 |
| Asp | Met | Gln | Ile | Ile | Gln | Pro | Ser | Ser | Asn | Ala | Leu | Leu | Tyr | Ser | Pro | |
| | | | | 20 | | | | | 25 | | | | | 30 | | |
| aat | aag | tat | ccg | tat | gcc | acg | gat | ccc | aat | gtc | ata | gca | gag | ggg | aga | 144 |
| Asn | Lys | Tyr | Pro | Tyr | Ala | Thr | Asp | Pro | Asn | Val | Ile | Ala | Glu | Gly | Arg | |
| | | 35 | | | | | 40 | | | | | 45 | | | | |
| agt | tat | aat | aat | tgg | ttg | gat | acg | tgt | gta | ggt | gta | ggc | gat | ggt | act | 192 |
| Ser | Tyr | Asn | Asn | Trp | Leu | Asp | Thr | Cys | Val | Gly | Val | Gly | Asp | Gly | Thr | |
| | 50 | | | | | 55 | | | | | 60 | | | | | |
| cga | agt | ccc | gag | gct | tat | gct | att | gcc | gaa | gag | gct | gtt | ggt | ctt | tcg | 240 |
| Arg | Ser | Pro | Glu | Ala | Tyr | Ala | Ile | Ala | Glu | Glu | Ala | Val | Gly | Leu | Ser | |
| 65 | | | | | 70 | | | | | 75 | | | | | 80 | |
| att | gat | ctt | ctc | gcc | gaa | act | ata | tac | ttt | cta | ggc | ttt | ccg | att | gca | 288 |
| Ile | Asp | Leu | Leu | Ala | Glu | Thr | Ile | Tyr | Phe | Leu | Gly | Phe | Pro | Ile | Ala | |
| | | | | 85 | | | | | 90 | | | | | 95 | | |
| tct | cca | atc | act | cgt | gca | cta | tct | gct | tta | ctg | ggg | ggg | cta | ttt | tct | 336 |
| Ser | Pro | Ile | Thr | Arg | Ala | Leu | Ser | Ala | Leu | Leu | Gly | Gly | Leu | Phe | Ser | |
| | | | | 100 | | | | | 105 | | | | | 110 | | |
| tct | ggg | gat | acg | ctg | atg | caa | cat | gta | gaa | caa | ctc | ata | aat | caa | aaa | 384 |
| Ser | Gly | Asp | Thr | Leu | Met | Gln | His | Val | Glu | Gln | Leu | Ile | Asn | Gln | Lys | |
| | | | 115 | | | | | 120 | | | | | 125 | | | |
| ata | gaa | att | tat | gca | aga | aat | acg | gca | ctt | gca | gaa | tta | ttg | ggt | tta | 432 |
| Ile | Glu | Ile | Tyr | Ala | Arg | Asn | Thr | Ala | Leu | Ala | Glu | Leu | Leu | Gly | Leu | |
| | 130 | | | | | 135 | | | | | 140 | | | | | |
| cgt | aat | gca | tta | gaa | gtc | tat | agt | gtg | gct | tta | gaa | tat | tgg | caa | caa | 480 |
| Arg | Asn | Ala | Leu | Glu | Val | Tyr | Ser | Val | Ala | Leu | Glu | Tyr | Trp | Gln | Gln | |
| 145 | | | | | 150 | | | | | 155 | | | | | 160 | |
| aat | cgt | aat | agt | gca | caa | gct | caa | gaa | agt | gta | aga | tca | aga | ttc | cgt | 528 |
| Asn | Arg | Asn | Ser | Ala | Gln | Ala | Gln | Glu | Ser | Val | Arg | Ser | Arg | Phe | Arg | |
| | | | | 165 | | | | | 170 | | | | | 175 | | |
| agt | cta | gaa | act | ata | ttt | ata | caa | agg | atg | cct | tta | ttt | gca | ata | caa | 576 |
| Ser | Leu | Glu | Thr | Ile | Phe | Ile | Gln | Arg | Met | Pro | Leu | Phe | Ala | Ile | Gln | |
| | | | 180 | | | | | 185 | | | | | 190 | | | |
| ggt | tat | gag | gtg | ccg | tta | tta | tcc | gtg | tat | gca | gcc | gct | gca | aat | ctc | 624 |
| Gly | Tyr | Glu | Val | Pro | Leu | Leu | Ser | Val | Tyr | Ala | Ala | Ala | Ala | Asn | Leu | |
| | | 195 | | | | | 200 | | | | | 205 | | | | |
| cat | tta | cta | tta | tta | agg | gat | agc | tct | att | cac | ggt | tta | gac | tgg | gga | 672 |
| His | Leu | Leu | Leu | Leu | Arg | Asp | Ser | Ser | Ile | His | Gly | Leu | Asp | Trp | Gly | |
| | 210 | | | | | 215 | | | | | 220 | | | | | |
| ttt | gat | caa | gga | gag | gtt | aac | agt | aat | tac | gat | cgc | caa | att | agg | ctc | 720 |
| Phe | Asp | Gln | Gly | Glu | Val | Asn | Ser | Asn | Tyr | Asp | Arg | Gln | Ile | Arg | Leu | |
| 225 | | | | | 230 | | | | | 235 | | | | | 240 | |
| tct | gca | gag | tat | gca | aat | cat | tgt | ata | act | tgg | tat | cag | gcg | ggt | tta | 768 |
| Ser | Ala | Glu | Tyr | Ala | Asn | His | Cys | Ile | Thr | Trp | Tyr | Gln | Ala | Gly | Leu | |
| | | | | 245 | | | | | 250 | | | | | 255 | | |
| caa | gga | ttg | cag | ggc | acc | agg | ggg | cga | | | | | | | | 795 |
| Gln | Gly | Leu | Gln | Gly | Thr | Arg | Gly | Arg | | | | | | | | |
| | | | 260 | | | | | 265 | | | | | | | | |

<210> SEQ ID NO 8
<211> LENGTH: 265
<212> TYPE: PRT
<213> ORGANISM: Bacillus popilliae

<400> SEQUENCE: 8

```
Gln Tyr His Asn Gln Asn Asp Asn Lys Ser Tyr Asn Gln Ser Gly Asn
  1               5                  10                  15

Asp Met Gln Ile Ile Gln Pro Ser Ser Asn Ala Leu Leu Tyr Ser Pro
             20                  25                  30

Asn Lys Tyr Pro Tyr Ala Thr Asp Pro Asn Val Ile Ala Glu Gly Arg
         35                  40                  45

Ser Tyr Asn Asn Trp Leu Asp Thr Cys Val Gly Val Gly Asp Gly Thr
     50                  55                  60

Arg Ser Pro Glu Ala Tyr Ala Ile Ala Glu Glu Ala Val Gly Leu Ser
 65                  70                  75                  80

Ile Asp Leu Leu Ala Glu Thr Ile Tyr Phe Leu Gly Phe Pro Ile Ala
                 85                  90                  95

Ser Pro Ile Thr Arg Ala Leu Ser Ala Leu Leu Gly Gly Leu Phe Ser
            100                 105                 110

Ser Gly Asp Thr Leu Met Gln His Val Glu Gln Leu Ile Asn Gln Lys
        115                 120                 125

Ile Glu Ile Tyr Ala Arg Asn Thr Ala Leu Ala Glu Leu Leu Gly Leu
    130                 135                 140

Arg Asn Ala Leu Glu Val Tyr Ser Val Ala Leu Glu Tyr Trp Gln Gln
145                 150                 155                 160

Asn Arg Asn Ser Ala Gln Ala Gln Glu Ser Val Arg Ser Arg Phe Arg
                165                 170                 175

Ser Leu Glu Thr Ile Phe Ile Gln Arg Met Pro Leu Phe Ala Ile Gln
            180                 185                 190

Gly Tyr Glu Val Pro Leu Leu Ser Val Tyr Ala Ala Ala Ala Asn Leu
        195                 200                 205

His Leu Leu Leu Leu Arg Asp Ser Ser Ile His Gly Leu Asp Trp Gly
    210                 215                 220

Phe Asp Gln Gly Glu Val Asn Ser Asn Tyr Asp Arg Gln Ile Arg Leu
225                 230                 235                 240

Ser Ala Glu Tyr Ala Asn His Cys Ile Thr Trp Tyr Gln Ala Gly Leu
                245                 250                 255

Gln Gly Leu Gln Gly Thr Arg Gly Arg
            260                 265
```

<210> SEQ ID NO 9
<211> LENGTH: 459
<212> TYPE: DNA
<213> ORGANISM: Bacillus popilliae
<220> FEATURE:
<221> NAME/KEY: CDS
<222> LOCATION: (1)..(459)

<400> SEQUENCE: 9

```
tat gag gtc cca tta tta tcc gtg tat gca gac gct gca aat ctc cat       48
Tyr Glu Val Pro Leu Leu Ser Val Tyr Ala Asp Ala Ala Asn Leu His
  1               5                  10                  15 ttg cta ata tta agg gac agc tat att tac ggt gca ttc tgg ggg ttt       96
Leu Leu Ile Leu Arg Asp Ser Tyr Ile Tyr Gly Ala Phe Trp Gly Phe
             20                  25                  30 gat gaa gat gaa tat tac cgt aat tac gct cgc caa att agg ctc tcc      144
```

```
                                                                            192
gca gag tat gca aat cat tgt aca act tgg tat cag acg ggt tta cga
Ala Glu Tyr Ala Asn His Cys Thr Thr Trp Tyr Gln Thr Gly Leu Arg
     50                   55                  60

240
aga ttg cag ggc acc cga gct aca gat tgg atc aat tat aat cga ttt
Arg Leu Gln Gly Thr Arg Ala Thr Asp Trp Ile Asn Tyr Asn Arg Phe
 65              70                  75                  80

288
aga aga gaa ctg aca cta aca gta tta gat att tgt gca tta ttt tct
Arg Arg Glu Leu Thr Leu Thr Val Leu Asp Ile Cys Ala Leu Phe Ser
                 85                  90                  95

336
agc tat gat att cct agt tac ccg atg ggg aca aag ata cag ctt acg
Ser Tyr Asp Ile Pro Ser Tyr Pro Met Gly Thr Lys Ile Gln Leu Thr
                100                 105                 110

384
aga gaa att tat acc gat cca gta gta cac tct gac tgg ttg caa tca
Arg Glu Ile Tyr Thr Asp Pro Val Val His Ser Asp Trp Leu Gln Ser
            115                 120                 125

432
acg agt ccg gga tta ata tca ttc tca tca cta gaa aat cta gtc gtt
Thr Ser Pro Gly Leu Ile Ser Phe Ser Ser Leu Glu Asn Leu Val Val
    130                 135                 140

459
cgg gca cca cat ctt ttt act tgg ctt
Arg Ala Pro His Leu Phe Thr Trp Leu
145                 150
```

Asp Glu Asp Glu Tyr Tyr Arg Asn Tyr Ala Arg Gln Ile Arg Leu Ser
             35                  40                  45

<210> SEQ ID NO 10
<211> LENGTH: 153
<212> TYPE: PRT
<213> ORGANISM: Bacillus popilliae

<400> SEQUENCE: 10

Tyr Glu Val Pro Leu Leu Ser Val Tyr Ala Asp Ala Ala Asn Leu His
 1               5                  10                  15

Leu Leu Ile Leu Arg Asp Ser Tyr Ile Tyr Gly Ala Phe Trp Gly Phe
             20                  25                  30

Asp Glu Asp Glu Tyr Tyr Arg Asn Tyr Ala Arg Gln Ile Arg Leu Ser
             35                  40                  45

Ala Glu Tyr Ala Asn His Cys Thr Thr Trp Tyr Gln Thr Gly Leu Arg
     50                  55                  60

Arg Leu Gln Gly Thr Arg Ala Thr Asp Trp Ile Asn Tyr Asn Arg Phe
 65              70                  75                  80

Arg Arg Glu Leu Thr Leu Thr Val Leu Asp Ile Cys Ala Leu Phe Ser
                 85                  90                  95

Ser Tyr Asp Ile Pro Ser Tyr Pro Met Gly Thr Lys Ile Gln Leu Thr
                100                 105                 110

Arg Glu Ile Tyr Thr Asp Pro Val Val His Ser Asp Trp Leu Gln Ser
            115                 120                 125

Thr Ser Pro Gly Leu Ile Ser Phe Ser Ser Leu Glu Asn Leu Val Val
    130                 135                 140

Arg Ala Pro His Leu Phe Thr Trp Leu
145                 150

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: misc_feature
<222> LOCATION: (5,11,12)

```
<223> OTHER INFORMATION: n=a or g or c or t

<400> SEQUENCE: 11
atgcngaagt nnatttacac gtgtt                                              25

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: misc_feature
<222> LOCATION: (14,15)
<223> OTHER INFORMATION: n=a or g or c or t

<400> SEQUENCE: 12
atgttgtggc taannac                                                       17

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 13
gtaaacgata cttttacttg                                                    20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 14
tctcgatcac gaatgatcat                                                    20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 15
gtgtcatttc tcttctaaat                                                    20

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 16
gtggaacaag aatatgagaa atctgtactc                                         30

<210> SEQ ID NO 17
<211> LENGTH: 4359
<212> TYPE: DNA
<213> ORGANISM: Bacillus popilliae
<220> FEATURE:
<221> NAME/KEY: CDS
<222> LOCATION: (250)..(4245)
```

-continued

```
<400> SEQUENCE: 17
ttgccagatg ttcatatcga ttgtcaatat gtgacggtat gtgatttaca aatgatgccc      60
gttcatgagg gagcttgtca atttgtgaag attagcggag aatttcaatt ttattcactt     120
taacattagc tacaaatgtt gtggctaagc accccattat ttatcaacgg gtaacaacca     180 ggagggtaa ctttgaatca gtatcaacat caaaacgata acaaaagtta caatcaagat      240 ggaaatgaa atg cag atc ata caa cct tca agt aac gct tta ctt tac agt    291
            Met Gln Ile Ile Gln Pro Ser Ser Asn Ala Leu Leu Tyr Ser
            1               5                   10 ccc aat aag tat ccg tat gcc acg gat ccc aat gtc ata gca gag ggg       339
Pro Asn Lys Tyr Pro Tyr Ala Thr Asp Pro Asn Val Ile Ala Glu Gly
15                  20                  25                  30 aga agt tat aat aat tgg ttg gat acg tgt gta ggt gta ggc gat ggt       387
Arg Ser Tyr Asn Asn Trp Leu Asp Thr Cys Val Gly Val Gly Asp Gly
                35                  40                  45 act cga agt ccc gag gct tat gct att gcc gaa gag gct gtc ggt ctt       435
Thr Arg Ser Pro Glu Ala Tyr Ala Ile Ala Glu Glu Ala Val Gly Leu
        50                  55                  60 tca att gat ata ttg gcc gaa att ata tac tat cta ggc ttc ccg att       483
Ser Ile Asp Ile Leu Ala Glu Ile Ile Tyr Tyr Leu Gly Phe Pro Ile
    65                  70                  75 gca tct cca ctc act cgt gca cta agt gct ata gcg gga cag cta ttt       531
Ala Ser Pro Leu Thr Arg Ala Leu Ser Ala Ile Ala Gly Gln Leu Phe
80                  85                  90 tct tct ggg gat acg ctc atg caa cat att gaa caa ctc ata aat caa       579
Ser Ser Gly Asp Thr Leu Met Gln His Ile Glu Gln Leu Ile Asn Gln
95                  100                 105                 110 aaa ata gcg gaa tat gcc aga aat aag gcg ctt gca gaa ttt cag ggt       627
Lys Ile Ala Glu Tyr Ala Arg Asn Lys Ala Leu Ala Glu Phe Gln Gly
                115                 120                 125 tta ggt aga caa tat ggg tta tat tta gag gct tta gaa gat tgg gaa       675
Leu Gly Arg Gln Tyr Gly Leu Tyr Leu Glu Ala Leu Glu Asp Trp Glu
            130                 135                 140 caa aat cgt ctt agt caa cca cat aaa gag cgt gta aga caa aca ttc       723
Gln Asn Arg Leu Ser Gln Pro His Lys Glu Arg Val Arg Gln Thr Phe
        145                 150                 155 cgt att ctt gat aat agc ttt aca tca tct ata cct tca ttt gca gta       771
Arg Ile Leu Asp Asn Ser Phe Thr Ser Ser Ile Pro Ser Phe Ala Val
    160                 165                 170 cga aat tat gag gtt cca tta tta tcc gtg tat gca gac gct gca aat       819
Arg Asn Tyr Glu Val Pro Leu Leu Ser Val Tyr Ala Asp Ala Ala Asn
175                 180                 185                 190 ctc cat ttg cta ata tta agg gac agc tat att tac ggt gca ttc tgg       867
Leu His Leu Leu Ile Leu Arg Asp Ser Tyr Ile Tyr Gly Ala Phe Trp
                195                 200                 205 ggg ttt gat gaa gat gaa tat tac cgt aat tac gct cgc caa att agg       915
Gly Phe Asp Glu Asp Glu Tyr Tyr Arg Asn Tyr Ala Arg Gln Ile Arg
            210                 215                 220 ctc tcc gca gag tat gca aat cat tgt aca act tgg tat cag acg ggt       963
Leu Ser Ala Glu Tyr Ala Asn His Cys Thr Thr Trp Tyr Gln Thr Gly
        225                 230                 235 tta cga aga ttg cag ggc acc cga gct aca gat tgg atc aat tat aat      1011
Leu Arg Arg Leu Gln Gly Thr Arg Ala Thr Asp Trp Ile Asn Tyr Asn
    240                 245                 250 cga ttt aga aga gaa atg aca cta aca gta tta gat att tgt gca tta      1059
Arg Phe Arg Arg Glu Met Thr Leu Thr Val Leu Asp Ile Cys Ala Leu
255                 260                 265                 270 ttt tct agc tat gat att cct agt tac ccg atg ggg aca aag ata cag      1107
```

```
                Phe Ser Ser Tyr Asp Ile Pro Ser Tyr Pro Met Gly Thr Lys Ile Gln
                            275                 280                 285 ctt acg aga gaa att tat acc gat cca gta gta cac tct gac tgg ttg        1155
Leu Thr Arg Glu Ile Tyr Thr Asp Pro Val Val His Ser Asp Trp Leu
                290                 295                 300 caa tca acg agt ccg gga tta ata tca ttc tca tca cta gaa aat cta        1203
Gln Ser Thr Ser Pro Gly Leu Ile Ser Phe Ser Ser Leu Glu Asn Leu
            305                 310                 315 gtc gtt cgg gca cca cat ctt ttt act tgg ctt tct cga gta aca att        1251
Val Val Arg Ala Pro His Leu Phe Thr Trp Leu Ser Arg Val Thr Ile
        320                 325                 330 gat aca ggt ata ttg tct act gta att ggc ggg cag tat agt aat aac        1299
Asp Thr Gly Ile Leu Ser Thr Val Ile Gly Gly Gln Tyr Ser Asn Asn
335                 340                 345                 350 aat ttt tgg cga aca cat tat caa act ttg cgt aca acc ggg ggc aca        1347
Asn Phe Trp Arg Thr His Tyr Gln Thr Leu Arg Thr Thr Gly Gly Thr
                355                 360                 365 tct ttc caa agt cct acc tat ggc tcg aca gcg ttt cca att caa cgc        1395
Ser Phe Gln Ser Pro Thr Tyr Gly Ser Thr Ala Phe Pro Ile Gln Arg
            370                 375                 380 acg aat aca ttg act ttc tcc ggc gat gtt tac acc ata gag tca agt        1443
Thr Asn Thr Leu Thr Phe Ser Gly Asp Val Tyr Thr Ile Glu Ser Ser
        385                 390                 395 gtt gtt acg agg agt tcc ttg tat gga gct aat tcg gtt gca ttt acg        1491
Val Val Thr Arg Ser Ser Leu Tyr Gly Ala Asn Ser Val Ala Phe Thr
400                 405                 410 ggt act act ggt cgg tca cta tat gag aac cca acg gtt tat ccg ttt        1539
Gly Thr Thr Gly Arg Ser Leu Tyr Glu Asn Pro Thr Val Tyr Pro Phe
415                 420                 425                 430 gca caa aaa tta att cat gaa tta cct gga gta gac tca ggt aga cca        1587
Ala Gln Lys Leu Ile His Glu Leu Pro Gly Val Asp Ser Gly Arg Pro
                435                 440                 445 aat gct acc aac tat agt cat aga ctg tcg tat atc tca ggt ttc agt        1635
Asn Ala Thr Asn Tyr Ser His Arg Leu Ser Tyr Ile Ser Gly Phe Ser
            450                 455                 460 ctt ggt tat tct cct tct gga acg ggt cta gtt tat ggg tgg aca tct        1683
Leu Gly Tyr Ser Pro Ser Gly Thr Gly Leu Val Tyr Gly Trp Thr Ser
        465                 470                 475 aca act gct act cgt gag aat aat att acg cta gac gac aga ata gta        1731
Thr Thr Ala Thr Arg Glu Asn Asn Ile Thr Leu Asp Asp Arg Ile Val
                480                 485                 490 cag ctt cca gct gtt aag gga gca agt ctc aat aat tgc caa gta gta        1779
Gln Leu Pro Ala Val Lys Gly Ala Ser Leu Asn Asn Cys Gln Val Val
495                 500                 505                 510 aaa ggg act gga ttt aca gga gga gac tgg ttg aaa cct aat aat aat        1827
Lys Gly Thr Gly Phe Thr Gly Gly Asp Trp Leu Lys Pro Asn Asn Asn
                515                 520                 525 ggt aca ttt tct atg tac ttt gca ttc agg tcg gct tac act tac cac        1875
Gly Thr Phe Ser Met Tyr Phe Ala Phe Arg Ser Ala Tyr Thr Tyr His
            530                 535                 540 ttc cgc att cgt tat gct tcc tca gca agt ttt tct ttt gta ata tcg        1923
Phe Arg Ile Arg Tyr Ala Ser Ser Ala Ser Phe Ser Phe Val Ile Ser
        545                 550                 555 gaa gaa tat gga cgt ttt cca acc aca aca gtg ccg ctt ctc tcc aca        1971
Glu Glu Tyr Gly Arg Phe Pro Thr Thr Thr Val Pro Leu Leu Ser Thr
                560                 565                 570 atg tca cca ctg ccc caa aat aca cca ttc gaa gct ttt aag act gta        2019
Met Ser Pro Leu Pro Gln Asn Thr Pro Phe Glu Ala Phe Lys Thr Val
575                 580                 585                 590
```

```
gat tta cct tct act gtt act att aga tat act tct gct gct tca aca      2067
Asp Leu Pro Ser Thr Val Thr Ile Arg Tyr Thr Ser Ala Ala Ser Thr
            595                 600                 605 act ttt caa ctt aat ttc cgt ttc act gtg cca gga agc gca aat gta      2115
Thr Phe Gln Leu Asn Phe Arg Phe Thr Val Pro Gly Ser Ala Asn Val
            610                 615                 620 ttg att gac cga att gaa ttt gtt cca att gag ggt tcc ttg ttc gag      2163
Leu Ile Asp Arg Ile Glu Phe Val Pro Ile Glu Gly Ser Leu Phe Glu
            625                 630                 635 tac gaa acc aaa cag cag cta gaa aaa gca agg aaa gcg gtg aac cat      2211
Tyr Glu Thr Lys Gln Gln Leu Glu Lys Ala Arg Lys Ala Val Asn His
            640                 645                 650 ttg ttt aca gat gga tcg aaa aag gcg cta aaa gaa gac acg acc gat      2259
Leu Phe Thr Asp Gly Ser Lys Lys Ala Leu Lys Glu Asp Thr Thr Asp
655                 660                 665                 670 tat gag att gat caa gcc gcc aac gtg gta gat tgt ata tcg gat gag      2307
Tyr Glu Ile Asp Gln Ala Ala Asn Val Val Asp Cys Ile Ser Asp Glu
            675                 680                 685 tgt gga cat gag aaa atg atc ctg tta gat gaa gta aaa tat gca aaa      2355
Cys Gly His Glu Lys Met Ile Leu Leu Asp Glu Val Lys Tyr Ala Lys
            690                 695                 700 caa ctc agc caa gcc cgc aat tta ctg ctc aat ggg aat ttc gat gat      2403
Gln Leu Ser Gln Ala Arg Asn Leu Leu Leu Asn Gly Asn Phe Asp Asp
            705                 710                 715 cta tat cca gct ctg gag agg gag aat cca tgg aaa aca agt ccg aat      2451
Leu Tyr Pro Ala Leu Glu Arg Glu Asn Pro Trp Lys Thr Ser Pro Asn
            720                 725                 730 gtt acg atc cgt caa gat aac ccg att ttt aaa ggc cat tat ctc agt      2499
Val Thr Ile Arg Gln Asp Asn Pro Ile Phe Lys Gly His Tyr Leu Ser
735                 740                 745                 750 atg gcg ggt gcg aac gat atc gag gcc acc aat gat acg ttc ccc acg      2547
Met Ala Gly Ala Asn Asp Ile Glu Ala Thr Asn Asp Thr Phe Pro Thr
            755                 760                 765 tat gtc tat caa aaa ata gat gaa gcc aaa tta aag cca tat aca cgg      2595
Tyr Val Tyr Gln Lys Ile Asp Glu Ala Lys Leu Lys Pro Tyr Thr Arg
            770                 775                 780 tat aaa gtg cgc ggg ttt gtt ggc agc agc aaa gat ctg gag ctg ttg      2643
Tyr Lys Val Arg Gly Phe Val Gly Ser Ser Lys Asp Leu Glu Leu Leu
            785                 790                 795 gtt aca cgc tat aat gaa gaa gtt gat gcg att tta gat gta ccg gat      2691
Val Thr Arg Tyr Asn Glu Glu Val Asp Ala Ile Leu Asp Val Pro Asp
            800                 805                 810 aat atc ccg cat gcg ccg act cct gtc tgc ggt gaa ttt gat cga tgc      2739
Asn Ile Pro His Ala Pro Thr Pro Val Cys Gly Glu Phe Asp Arg Cys
815                 820                 825                 830 aag ccc tat tcg tat cca cct tta ctt cca gaa tgt aac cct gag ttt      2787
Lys Pro Tyr Ser Tyr Pro Pro Leu Leu Pro Glu Cys Asn Pro Glu Phe
            835                 840                 845 ata aat cag atg caa cca tcc tct tgc cac cac aat cag atg gtc gat      2835
Ile Asn Gln Met Gln Pro Ser Ser Cys His His Asn Gln Met Val Asp
            850                 855                 860 tac aat aac atg aac acg agc acg agt act acc atg aat cct agc atg      2883
Tyr Asn Asn Met Asn Thr Ser Thr Ser Thr Thr Met Asn Pro Ser Met
            865                 870                 875 aat cct ccc ctt acg cct gaa ata gca tcc agc caa agt gga ttc ggc      2931
Asn Pro Pro Leu Thr Pro Glu Ile Ala Ser Ser Gln Ser Gly Phe Gly
            880                 885                 890 aga aaa cat cgc aaa tgt cat caa gca cat caa ttt gag ttc cac att      2979
Arg Lys His Arg Lys Cys His Gln Ala His Gln Phe Glu Phe His Ile
895                 900                 905                 910
```

| | | |
|---|---|---|
| gat acc ggg aca atc gat ttg gtg gaa gat ttg ggc att tgg gtg atc<br>Asp Thr Gly Thr Ile Asp Leu Val Glu Asp Leu Gly Ile Trp Val Ile<br>              915                 920                925 | | 3027 |
| ttc aaa atc tgt gcc aca gat gga tac gca agc tta gat gat ctg gaa<br>Phe Lys Ile Cys Ala Thr Asp Gly Tyr Ala Ser Leu Asp Asp Leu Glu<br>            930               935                940 | | 3075 |
| gtg att gaa gaa gga gcg ctg ggg gtc gaa gcc tta gaa ctt gtc aag<br>Val Ile Glu Glu Gly Ala Leu Gly Val Glu Ala Leu Glu Leu Val Lys<br>            945               950                955 | | 3123 |
| aaa aga gaa aag aaa tgg aga cat cag aag gag cag cac tgt tcg caa<br>Lys Arg Glu Lys Lys Trp Arg His Gln Lys Glu Gln His Cys Ser Gln<br>960                  965                970 | | 3171 |
| acg aaa cac aaa tat gat gcg gcc aaa cat gcg gtg atg gcg tta ttt<br>Thr Lys His Lys Tyr Asp Ala Ala Lys His Ala Val Met Ala Leu Phe<br>975                 980               985               990 | | 3219 |
| aca aac acg cgc tat gaa aaa ttg aag ttc gaa aca acc att tct gac<br>Thr Asn Thr Arg Tyr Glu Lys Leu Lys Phe Glu Thr Thr Ile Ser Asp<br>            995               1000              1005 | | 3267 |
| att ttg tat gct gat cat ctc gtg cag tcg att cct tat gta tat aat<br>Ile Leu Tyr Ala Asp His Leu Val Gln Ser Ile Pro Tyr Val Tyr Asn<br>            1010               1015              1020 | | 3315 |
| aaa tat gta ccg gaa gtt tca ggt atg aat tac gaa ctc tat aca gag<br>Lys Tyr Val Pro Glu Val Ser Gly Met Asn Tyr Glu Leu Tyr Thr Glu<br>            1025               1030              1035 | | 3363 |
| cta aac act ctc gtt cag aat gcg ttc tac ctg tat gac cag cgg aat<br>Leu Asn Thr Leu Val Gln Asn Ala Phe Tyr Leu Tyr Asp Gln Arg Asn<br>            1040               1045              1050 | | 3411 |
| ctg att aaa aat ggg cgc ttt agc aat ggg ctt atg tat tgg caa gct<br>Leu Ile Lys Asn Gly Arg Phe Ser Asn Gly Leu Met Tyr Trp Gln Ala<br>1055               1060               1065              1070 | | 3459 |
| acc ccg cat gca cga gtg gag caa gaa tat gat aga tca gtg ctg gtg<br>Thr Pro His Ala Arg Val Glu Gln Glu Tyr Asp Arg Ser Val Leu Val<br>            1075               1080              1085 | | 3507 |
| ctg ccg aat tgg gat gcc aat gtg tcg caa cag ctg tgt atc gaa cac<br>Leu Pro Asn Trp Asp Ala Asn Val Ser Gln Gln Leu Cys Ile Glu His<br>            1090               1095              1100 | | 3555 |
| aat cgc ggt tat gta ttg cgt gtc acg gcg aga aaa gaa gat ccg gga<br>Asn Arg Gly Tyr Val Leu Arg Val Thr Ala Arg Lys Glu Asp Pro Gly<br>            1105               1110              1115 | | 3603 |
| gcc ggc aat gtt acc ttt agt gac tgt gca aat cat gtc gac aag ctg<br>Ala Gly Asn Val Thr Phe Ser Asp Cys Ala Asn His Val Asp Lys Leu<br>            1120               1125              1130 | | 3651 |
| agc ttt act tct tgc gat ata gct aca aac gca gtg cca ggt gcc caa<br>Ser Phe Thr Ser Cys Asp Ile Ala Thr Asn Ala Val Pro Gly Ala Gln<br>1135               1140               1145              1150 | | 3699 |
| gcg aat gat cca gcc gcc gga gta gcc tat gga caa cag ggt tgt caa<br>Ala Asn Asp Pro Ala Ala Gly Val Ala Tyr Gly Gln Gln Gly Cys Gln<br>            1155               1160              1165 | | 3747 |
| ata gat aga gtg ccg tac gga cca tct gga tat cga gca gac gga gta<br>Ile Asp Arg Val Pro Tyr Gly Pro Ser Gly Tyr Arg Ala Asp Gly Val<br>            1170               1175              1180 | | 3795 |
| gcg tac gaa cag tct ggt cat cga aca gat gga gtg ccg tac aga caa<br>Ala Tyr Glu Gln Ser Gly His Arg Thr Asp Gly Val Pro Tyr Arg Gln<br>            1185               1190              1195 | | 3843 |
| tct gga tat cga gca gac gga gta gcg cac gac caa cct gga tat cga<br>Ser Gly Tyr Arg Ala Asp Gly Val Ala His Asp Gln Pro Gly Tyr Arg<br>            1200               1205              1210 | | 3891 |
| gca gac gga gta gcg tac gaa caa tct gga tat cga gca gat gga gta<br>Ala Asp Gly Val Ala Tyr Glu Gln Ser Gly Tyr Arg Ala Asp Gly Val | | 3939 |

-continued

```
1215              1220              1225              1230 gcg tac gaa cag tct ggt cat cga gca gat gga gtg ccg tac gga caa     3987
Ala Tyr Glu Gln Ser Gly His Arg Ala Asp Gly Val Pro Tyr Gly Gln
                1235              1240              1245 tct gga tat gga aca gac gga gta acg tac gac caa tct gcc aaa caa     4035
Ser Gly Tyr Gly Thr Asp Gly Val Thr Tyr Asp Gln Ser Ala Lys Gln
            1250              1255              1260 acc cgc aaa tac cat ggt tgc cat aca gac gga ctg cca cat cca gag     4083
Thr Arg Lys Tyr His Gly Cys His Thr Asp Gly Leu Pro His Pro Glu
        1265              1270              1275 cat ggt tgt tgt tat cca gac aga gta agc gat ggc caa cag ctt gca     4131
His Gly Cys Cys Tyr Pro Asp Arg Val Ser Asp Gly Gln Gln Leu Ala
    1280              1285              1290 tat gta aca aaa tcg att gat ctg ttc ccg gat aca gat aaa gtc cgg     4179
Tyr Val Thr Lys Ser Ile Asp Leu Phe Pro Asp Thr Asp Lys Val Arg
1295              1300              1305              1310 atc gac att gga gaa acc gaa ggg aac ttt aga gtg gaa agt gtg gaa     4227
Ile Asp Ile Gly Glu Thr Glu Gly Asn Phe Arg Val Glu Ser Val Glu
                1315              1320              1325 ttg att tgt atg gaa aag taaatcatca caagtaaaag tatcgtttac           4275
Leu Ile Cys Met Glu Lys
            1330 taaaaattta ttttccaagc aacaggggag agggggctg tccagaaggt cagtgaaaac   4335 tggacgcccc gttttagtag aata                                         4359

<210> SEQ ID NO 18
<211> LENGTH: 1332
<212> TYPE: PRT
<213> ORGANISM: Bacillus popilliae

<400> SEQUENCE: 18

Met Gln Ile Ile Gln Pro Ser Ser Asn Ala Leu Leu Tyr Ser Pro Asn
  1               5                  10                  15

Lys Tyr Pro Tyr Ala Thr Asp Pro Asn Val Ile Ala Glu Gly Arg Ser
            20                  25                  30

Tyr Asn Asn Trp Leu Asp Thr Cys Val Gly Val Gly Asp Gly Thr Arg
        35                  40                  45

Ser Pro Glu Ala Tyr Ala Ile Ala Glu Glu Ala Val Gly Leu Ser Ile
    50                  55                  60

Asp Ile Leu Ala Glu Ile Ile Tyr Tyr Leu Gly Phe Pro Ile Ala Ser
 65                  70                  75                  80

Pro Leu Thr Arg Ala Leu Ser Ala Ile Ala Gly Gln Leu Phe Ser Ser
                85                  90                  95

Gly Asp Thr Leu Met Gln His Ile Glu Gln Leu Ile Asn Gln Lys Ile
            100                 105                 110

Ala Glu Tyr Ala Arg Asn Lys Ala Leu Ala Glu Phe Gln Gly Leu Gly
        115                 120                 125

Arg Gln Tyr Gly Leu Tyr Leu Glu Ala Leu Glu Asp Trp Glu Gln Asn
    130                 135                 140

Arg Leu Ser Gln Pro His Lys Glu Arg Val Arg Gln Thr Phe Arg Ile
145                 150                 155                 160

Leu Asp Asn Ser Phe Thr Ser Ser Ile Pro Ser Phe Ala Val Arg Asn
                165                 170                 175

Tyr Glu Val Pro Leu Leu Ser Val Tyr Ala Asp Ala Ala Asn Leu His
            180                 185                 190

Leu Leu Ile Leu Arg Asp Ser Tyr Ile Tyr Gly Ala Phe Trp Gly Phe
```

-continued

```
            195                 200                 205
Asp Glu Asp Glu Tyr Tyr Arg Asn Tyr Ala Arg Gln Ile Arg Leu Ser
    210                 215                 220

Ala Glu Tyr Ala Asn His Cys Thr Thr Trp Tyr Gln Thr Gly Leu Arg
225                 230                 235                 240

Arg Leu Gln Gly Thr Arg Ala Thr Asp Trp Ile Asn Tyr Asn Arg Phe
                245                 250                 255

Arg Arg Glu Met Thr Leu Thr Val Leu Asp Ile Cys Ala Leu Phe Ser
            260                 265                 270

Ser Tyr Asp Ile Pro Ser Tyr Pro Met Gly Thr Lys Ile Gln Leu Thr
        275                 280                 285

Arg Glu Ile Tyr Thr Asp Pro Val Val His Ser Asp Trp Leu Gln Ser
    290                 295                 300

Thr Ser Pro Gly Leu Ile Ser Phe Ser Ser Leu Glu Asn Leu Val Val
305                 310                 315                 320

Arg Ala Pro His Leu Phe Thr Trp Leu Ser Arg Val Thr Ile Asp Thr
                325                 330                 335

Gly Ile Leu Ser Thr Val Ile Gly Gly Gln Tyr Ser Asn Asn Asn Phe
            340                 345                 350

Trp Arg Thr His Tyr Gln Thr Leu Arg Thr Thr Gly Gly Thr Ser Phe
        355                 360                 365

Gln Ser Pro Thr Tyr Gly Ser Thr Ala Phe Pro Ile Gln Arg Thr Asn
    370                 375                 380

Thr Leu Thr Phe Ser Gly Asp Val Tyr Thr Ile Glu Ser Ser Val Val
385                 390                 395                 400

Thr Arg Ser Ser Leu Tyr Gly Ala Asn Ser Val Ala Phe Thr Gly Thr
                405                 410                 415

Thr Gly Arg Ser Leu Tyr Glu Asn Pro Thr Val Tyr Pro Phe Ala Gln
            420                 425                 430

Lys Leu Ile His Glu Leu Pro Gly Val Asp Ser Gly Arg Pro Asn Ala
        435                 440                 445

Thr Asn Tyr Ser His Arg Leu Ser Tyr Ile Ser Gly Phe Ser Leu Gly
    450                 455                 460

Tyr Ser Pro Ser Gly Thr Gly Leu Val Tyr Gly Trp Thr Ser Thr Thr
465                 470                 475                 480

Ala Thr Arg Glu Asn Asn Ile Thr Leu Asp Asp Arg Ile Val Gln Leu
                485                 490                 495

Pro Ala Val Lys Gly Ala Ser Leu Asn Asn Cys Gln Val Val Lys Gly
            500                 505                 510

Thr Gly Phe Thr Gly Gly Asp Trp Leu Lys Pro Asn Asn Gly Thr
        515                 520                 525

Phe Ser Met Tyr Phe Ala Phe Arg Ser Ala Tyr Thr Tyr His Phe Arg
    530                 535                 540

Ile Arg Tyr Ala Ser Ser Ala Ser Phe Ser Phe Val Ile Ser Glu Glu
545                 550                 555                 560

Tyr Gly Arg Phe Pro Thr Thr Val Pro Leu Leu Ser Thr Met Ser
                565                 570                 575

Pro Leu Pro Gln Asn Thr Pro Phe Glu Ala Phe Lys Thr Val Asp Leu
            580                 585                 590

Pro Ser Thr Val Thr Ile Arg Tyr Thr Ser Ala Ala Ser Thr Thr Phe
        595                 600                 605

Gln Leu Asn Phe Arg Phe Thr Val Pro Gly Ser Ala Asn Val Leu Ile
    610                 615                 620
```

```
Asp Arg Ile Glu Phe Val Pro Ile Glu Gly Ser Leu Phe Tyr Glu
625                 630                 635                 640

Thr Lys Gln Gln Leu Glu Lys Ala Arg Lys Ala Val Asn His Leu Phe
            645                 650                 655

Thr Asp Gly Ser Lys Lys Ala Leu Lys Glu Asp Thr Thr Asp Tyr Glu
            660                 665                 670

Ile Asp Gln Ala Ala Asn Val Val Asp Cys Ile Ser Asp Glu Cys Gly
            675                 680                 685

His Glu Lys Met Ile Leu Leu Asp Glu Val Lys Tyr Ala Lys Gln Leu
690                 695                 700

Ser Gln Ala Arg Asn Leu Leu Leu Asn Gly Asn Phe Asp Asp Leu Tyr
705                 710                 715                 720

Pro Ala Leu Glu Arg Glu Asn Pro Trp Lys Thr Ser Pro Asn Val Thr
                725                 730                 735

Ile Arg Gln Asp Asn Pro Ile Phe Lys Gly His Tyr Leu Ser Met Ala
                740                 745                 750

Gly Ala Asn Asp Ile Glu Ala Thr Asn Asp Thr Phe Pro Thr Tyr Val
            755                 760                 765

Tyr Gln Lys Ile Asp Glu Ala Lys Leu Lys Pro Tyr Thr Arg Tyr Lys
770                 775                 780

Val Arg Gly Phe Val Gly Ser Ser Lys Asp Leu Glu Leu Leu Val Thr
785                 790                 795                 800

Arg Tyr Asn Glu Glu Val Asp Ala Ile Leu Asp Val Pro Asp Asn Ile
                805                 810                 815

Pro His Ala Pro Thr Pro Val Cys Gly Glu Phe Asp Arg Cys Lys Pro
                820                 825                 830

Tyr Ser Tyr Pro Pro Leu Leu Pro Glu Cys Asn Pro Glu Phe Ile Asn
            835                 840                 845

Gln Met Gln Pro Ser Ser Cys His His Asn Gln Met Val Asp Tyr Asn
850                 855                 860

Asn Met Asn Thr Ser Thr Ser Thr Thr Met Asn Pro Ser Met Asn Pro
865                 870                 875                 880

Pro Leu Thr Pro Glu Ile Ala Ser Ser Gln Ser Gly Phe Gly Arg Lys
                885                 890                 895

His Arg Lys Cys His Gln Ala His Gln Phe Glu Phe His Ile Asp Thr
                900                 905                 910

Gly Thr Ile Asp Leu Val Glu Asp Leu Gly Ile Trp Val Ile Phe Lys
            915                 920                 925

Ile Cys Ala Thr Asp Gly Tyr Ala Ser Leu Asp Asp Leu Glu Val Ile
            930                 935                 940

Glu Glu Gly Ala Leu Gly Val Glu Ala Leu Glu Leu Val Lys Lys Arg
945                 950                 955                 960

Glu Lys Lys Trp Arg His Gln Lys Glu Gln His Cys Ser Gln Thr Lys
                965                 970                 975

His Lys Tyr Asp Ala Ala Lys His Ala Val Met Ala Leu Phe Thr Asn
            980                 985                 990

Thr Arg Tyr Glu Lys Leu Lys Phe Glu Thr Thr Ile Ser Asp Ile Leu
            995                 1000                1005

Tyr Ala Asp His Leu Val Gln Ser Ile Pro Tyr Val Tyr Asn Lys Tyr
        1010                1015                1020

Val Pro Glu Val Ser Gly Met Asn Tyr Glu Leu Tyr Thr Glu Leu Asn
1025                1030                1035                1040
```

-continued

```
Thr Leu Val Gln Asn Ala Phe Tyr Leu Tyr Asp Gln Arg Asn Leu Ile
            1045                1050                1055
Lys Asn Gly Arg Phe Ser Asn Gly Leu Met Tyr Trp Gln Ala Thr Pro
        1060                1065                1070
His Ala Arg Val Glu Gln Glu Tyr Asp Arg Ser Val Leu Val Leu Pro
        1075                1080                1085
Asn Trp Asp Ala Asn Val Ser Gln Gln Leu Cys Ile Glu His Asn Arg
        1090                1095                1100
Gly Tyr Val Leu Arg Val Thr Ala Arg Lys Glu Asp Pro Gly Ala Gly
1105                1110                1115                1120
Asn Val Thr Phe Ser Asp Cys Ala Asn His Val Asp Lys Leu Ser Phe
            1125                1130                1135
Thr Ser Cys Asp Ile Ala Thr Asn Ala Val Pro Gly Ala Gln Ala Asn
            1140                1145                1150
Asp Pro Ala Ala Gly Val Ala Tyr Gly Gln Gln Gly Cys Gln Ile Asp
        1155                1160                1165
Arg Val Pro Tyr Gly Pro Ser Gly Tyr Arg Ala Asp Gly Val Ala Tyr
        1170                1175                1180
Glu Gln Ser Gly His Arg Thr Asp Gly Val Pro Tyr Arg Gln Ser Gly
1185                1190                1195                1200
Tyr Arg Ala Asp Gly Val Ala His Asp Gln Pro Gly Tyr Arg Ala Asp
            1205                1210                1215
Gly Val Ala Tyr Glu Gln Ser Gly Tyr Arg Ala Asp Gly Val Ala Tyr
            1220                1225                1230
Glu Gln Ser Gly His Arg Ala Asp Gly Val Pro Tyr Gly Gln Ser Gly
        1235                1240                1245
Tyr Gly Thr Asp Gly Val Thr Tyr Asp Gln Ser Ala Lys Gln Thr Arg
        1250                1255                1260
Lys Tyr His Gly Cys His Thr Asp Gly Leu Pro His Pro Glu His Gly
1265                1270                1275                1280
Cys Cys Tyr Pro Asp Arg Val Ser Asp Gly Gln Gln Leu Ala Tyr Val
            1285                1290                1295
Thr Lys Ser Ile Asp Leu Phe Pro Asp Thr Asp Lys Val Arg Ile Asp
            1300                1305                1310
Ile Gly Glu Thr Glu Gly Asn Phe Arg Val Glu Ser Val Glu Leu Ile
        1315                1320                1325
Cys Met Glu Lys
    1330

<210> SEQ ID NO 19
<211> LENGTH: 4366
<212> TYPE: DNA
<213> ORGANISM: Bacillus popilliae
<220> FEATURE:
<221> NAME/KEY: CDS
<222> LOCATION: (224)..(4255)

<400> SEQUENCE: 19
gtagatcatg tactcaaatg cagtgtcgga agtttgccag atgttcatat cgattgtcaa      60
tatgtgacgg tatgtgattt acagatgagg cccgttcatg agggagcttg tcaatttgtg     120
aagattagcg gagaatttca atttattca ctttaacatt agctacaaat gttgtggcta     180
agcaccccat tatataaatg gatgacaacc aggaggggta act atg aat cag tat      235
                                              Met Asn Gln Tyr
                                                1 cat aac caa aac gat aac aaa agt tac aac caa agt gga aat gaa atg      283
```

```
                His Asn Gln Asn Asp Asn Lys Ser Tyr Asn Gln Ser Gly Asn Glu Met
                  5              10                  15                  20 caa atc att caa cct tca agt aat tct tta ctt tac agt ccc aat aag              331
Gln Ile Ile Gln Pro Ser Ser Asn Ser Leu Leu Tyr Ser Pro Asn Lys
            25                  30                  35 tat ccg tat gcc acg gat ccc aat gtc ata gca gag ggt aga agt tat              379
Tyr Pro Tyr Ala Thr Asp Pro Asn Val Ile Ala Glu Gly Arg Ser Tyr
                40                  45                  50 aaa aat tgg ctt gat atg tgt gta ggt gaa ggc gac ggt aca cga agt              427
Lys Asn Trp Leu Asp Met Cys Val Gly Glu Gly Asp Gly Thr Arg Ser
            55                  60                  65 ctc gag gct att gct gtt gct gtc gga gtt cga ata agc cac aca att              475
Leu Glu Ala Ile Ala Val Ala Val Gly Val Arg Ile Ser His Thr Ile
        70                  75                  80 ttc cgc ctt tta ggt gtt cca tat tca gct caa ggc gag caa tta ttt              523
Phe Arg Leu Leu Gly Val Pro Tyr Ser Ala Gln Gly Glu Gln Leu Phe
85                  90                  95                 100 agc ttc cta ttg gat acg tta tgg ctt gaa ggc aat act caa tgg gaa              571
Ser Phe Leu Leu Asp Thr Leu Trp Leu Glu Gly Asn Thr Gln Trp Glu
                105                 110                 115 gag ttg atg aga cat gca gaa gaa ctc ata aat gaa cag gta ccg gat              619
Glu Leu Met Arg His Ala Glu Glu Leu Ile Asn Glu Gln Val Pro Asp
            120                 125                 130 tat gta aga acc aag gca ctt gca gaa tta acg gat tta ggt aac aac              667
Tyr Val Arg Thr Lys Ala Leu Ala Glu Leu Thr Asp Leu Gly Asn Asn
        135                 140                 145 tta aat tta tat ata gca gct ttt gaa gat tgg aaa cga aat ccg agc              715
Leu Asn Leu Tyr Ile Ala Ala Phe Glu Asp Trp Lys Arg Asn Pro Ser
150                 155                 160 agt caa gaa gtt aga acc cgg gta ata gat aga ttc aat ata ctc gac              763
Ser Gln Glu Val Arg Thr Arg Val Ile Asp Arg Phe Asn Ile Leu Asp
165                 170                 175                 180 ggt tta ttt gaa gcc tat ctg cct tca ttt gca gta cct ggt tat gaa              811
Gly Leu Phe Glu Ala Tyr Leu Pro Ser Phe Ala Val Pro Gly Tyr Glu
                185                 190                 195 gta cca cta tta tcc gtg tat gca aat gtt gta aat atc cac tta ttg              859
Val Pro Leu Leu Ser Val Tyr Ala Asn Val Val Asn Ile His Leu Leu
            200                 205                 210 gta ctg agg gac agc tcg att tat ggc ctg gat tgg gga tta agt tca              907
Val Leu Arg Asp Ser Ser Ile Tyr Gly Leu Asp Trp Gly Leu Ser Ser
        215                 220                 225 act agt gtt gac aat aat tac aat cgc caa caa agg aac tcc gca acg              955
Thr Ser Val Asp Asn Asn Tyr Asn Arg Gln Gln Arg Asn Ser Ala Thr
230                 235                 240 tat gca aat cat tgt aca act tgg tat cag acg ggt tta caa aga ttg             1003
Tyr Ala Asn His Cys Thr Thr Trp Tyr Gln Thr Gly Leu Gln Arg Leu
245                 250                 255                 260 caa ggc agc gat gct agc agt tgg gtc aat tat aat cga ttt aga aga             1051
Gln Gly Ser Asp Ala Ser Ser Trp Val Asn Tyr Asn Arg Phe Arg Arg
                265                 270                 275 gaa ata acg tta ata gta ttg gat att tgt gca ttg ttt tca aat tat             1099
Glu Ile Thr Leu Ile Val Leu Asp Ile Cys Ala Leu Phe Ser Asn Tyr
            280                 285                 290 gat gtt cgt agt tat cca ata cag tta cgg gga gag ctt acg aga gga             1147
Asp Val Arg Ser Tyr Pro Ile Gln Leu Arg Gly Glu Leu Thr Arg Gly
        295                 300                 305 att tat acg gat cca gca gta tat agc ggt aca ggt tcc tat tcc tgg             1195
Ile Tyr Thr Asp Pro Ala Val Tyr Ser Gly Thr Gly Ser Tyr Ser Trp
310                 315                 320
```

```
ttg agt caa gca cca tca ttt gca gaa ata gaa aat atc gca att agg        1243
Leu Ser Gln Ala Pro Ser Phe Ala Glu Ile Glu Asn Ile Ala Ile Arg
325             330             335             340 gaa cca agc aat ttt act tgg gca tct tat gcg aga gta aca aca ggt        1291
Glu Pro Ser Asn Phe Thr Trp Ala Ser Tyr Ala Arg Val Thr Thr Gly
                345             350             355 aca ctg gaa tat ctc agc tct aag aat gat ttt tgg aaa tca cac tat        1339
Thr Leu Glu Tyr Leu Ser Ser Lys Asn Asp Phe Trp Lys Ser His Tyr
            360             365             370 atg aac tat act gaa acc aat tcg ggt ata ttg att caa gga cct acc        1387
Met Asn Tyr Thr Glu Thr Asn Ser Gly Ile Leu Ile Gln Gly Pro Thr
        375             380             385 tat gga atg acg acg ggt aca aat att cgt ata gag tcc gta tca atg        1435
Tyr Gly Met Thr Thr Gly Thr Asn Ile Arg Ile Glu Ser Val Ser Met
    390             395             400 caa gaa att tat tcc gtt aga tta gaa gct gtt gct cat gct gga gct        1483
Gln Glu Ile Tyr Ser Val Arg Leu Glu Ala Val Ala His Ala Gly Ala
405             410             415             420 ggg ggt cct ttt ttg gga atc tct acg tct gaa ttt ttc tgg agt ttg        1531
Gly Gly Pro Phe Leu Gly Ile Ser Thr Ser Glu Phe Phe Trp Ser Leu
                425             430             435 ggt gtt aga agg tat cag aac tca cgt agt cct caa ttt gcg tct caa        1579
Gly Val Arg Arg Tyr Gln Asn Ser Arg Ser Pro Gln Phe Ala Ser Gln
            440             445             450 ata ata act agg caa tta cct gga gta aac tca gcg gtt cca tct gcc        1627
Ile Ile Thr Arg Gln Leu Pro Gly Val Asn Ser Ala Val Pro Ser Ala
        455             460             465 ctc gac cat agt cat gaa cta tcg tat atc aca gcg ttt cca gtt aga        1675
Leu Asp His Ser His Glu Leu Ser Tyr Ile Thr Ala Phe Pro Val Arg
    470             475             480 tcg gtg gga acg att ctc gtt cat gaa tgg aca tct aca aca gtt agt        1723
Ser Val Gly Thr Ile Leu Val His Glu Trp Thr Ser Thr Thr Val Ser
485             490             495             500 cgt aac aat aga att gag cca gat aaa ata aca caa atc ccg gct gtt        1771
Arg Asn Asn Arg Ile Glu Pro Asp Lys Ile Thr Gln Ile Pro Ala Val
                505             510             515 aag tca cac aca ctc tcc aat tgt caa gta gtt agt ggg act ggg ttt        1819
Lys Ser His Thr Leu Ser Asn Cys Gln Val Val Ser Gly Thr Gly Phe
            520             525             530 acg gga gga aac tgg tta aga cct tct gat aat ggt tca ttt aga cta        1867
Thr Gly Gly Asn Trp Leu Arg Pro Ser Asp Asn Gly Ser Phe Arg Leu
        535             540             545 acg att act tca ttc tca agc caa tct tac cgc att cgc att cat tat        1915
Thr Ile Thr Ser Phe Ser Ser Gln Ser Tyr Arg Ile Arg Ile His Tyr
    550             555             560 gct tcc gca aca ttt ttt tat ttg gat att cgt acg ggt gat act tct        1963
Ala Ser Ala Thr Phe Phe Tyr Leu Asp Ile Arg Thr Gly Asp Thr Ser
565             570             575             580 aac aca ttt gcg gtt acc cca aca aca tta tca tca gga tcc caa act        2011
Asn Thr Phe Ala Val Thr Pro Thr Thr Leu Ser Ser Gly Ser Gln Thr
                585             590             595 gta ccc tac gaa tct ttt ggg ttt ata aat ata cct tat act ttt aca        2059
Val Pro Tyr Glu Ser Phe Gly Phe Ile Asn Ile Pro Tyr Thr Phe Thr
            600             605             610 aca gca cct act gaa agt aga tat act ttt gat ttc atg ttc tac tca        2107
Thr Ala Pro Thr Glu Ser Arg Tyr Thr Phe Asp Phe Met Phe Tyr Ser
        615             620             625 ata gga agc gca aat gta tta att gac cga att gaa att gtt cca atc        2155
Ile Gly Ser Ala Asn Val Leu Ile Asp Arg Ile Glu Ile Val Pro Ile
    630             635             640
```

-continued

```
gga gtt cct ttg ttc gag tac gaa acc aaa cag cag cta gaa aaa gca      2203
Gly Val Pro Leu Phe Glu Tyr Glu Thr Lys Gln Gln Leu Glu Lys Ala
645                 650                 655                 660 agg aaa gcg gtg aac cat ttg ttt aca gat gga tcg aaa aag gcg cta      2251
Arg Lys Ala Val Asn His Leu Phe Thr Asp Gly Ser Lys Lys Ala Leu
                665                 670                 675 aaa gaa gac acg acc gat tat gag att gat caa gcc gcc aac gtg gta      2299
Lys Glu Asp Thr Thr Asp Tyr Glu Ile Asp Gln Ala Ala Asn Val Val
            680                 685                 690 gat tgt ata tcg gat gag tgt gga cat gat aaa atg atc ctg tta gat      2347
Asp Cys Ile Ser Asp Glu Cys Gly His Asp Lys Met Ile Leu Leu Asp
        695                 700                 705 gaa gta aaa tat gca aaa caa ctc agc caa gcc cgc aat tta ctg ctc      2395
Glu Val Lys Tyr Ala Lys Gln Leu Ser Gln Ala Arg Asn Leu Leu Leu
    710                 715                 720 aat ggg aat ttc gat gat cta tat tca gct ctg gag aag gag aat cca      2443
Asn Gly Asn Phe Asp Asp Leu Tyr Ser Ala Leu Glu Lys Glu Asn Pro
725                 730                 735                 740 tgg aaa aca agt ccg aat gtt acg atc cga caa gat aac ccg att ttt      2491
Trp Lys Thr Ser Pro Asn Val Thr Ile Arg Gln Asp Asn Pro Ile Phe
                745                 750                 755 aaa ggc cat tat ctc agt atg gcg ggt gcg aac gat atc gag gcc acc      2539
Lys Gly His Tyr Leu Ser Met Ala Gly Ala Asn Asp Ile Glu Ala Thr
            760                 765                 770 aat gat acc ttc ccc acg tat gtc tat caa aaa ata gac gaa gcc aaa      2587
Asn Asp Thr Phe Pro Thr Tyr Val Tyr Gln Lys Ile Asp Glu Ala Lys
        775                 780                 785 tta aag ccg tat aca cgt tat aaa gtg cgc ggg ttt gtt ggc agc agc      2635
Leu Lys Pro Tyr Thr Arg Tyr Lys Val Arg Gly Phe Val Gly Ser Ser
    790                 795                 800 aaa gct cta gag ctg ttg gtt aca cgc tat aat gaa gaa gtt gat gcg      2683
Lys Ala Leu Glu Leu Leu Val Thr Arg Tyr Asn Glu Glu Val Asp Ala
805                 810                 815                 820 att tta gat gta ccg gat aat atc ccg cat gcg ccg act cct gtc tgc      2731
Ile Leu Asp Val Pro Asp Asn Ile Pro His Ala Pro Thr Pro Val Cys
                825                 830                 835 ggt gaa ttt gat cga tgc aag ccc tat tcg tat cca cct tta ctt cca      2779
Gly Glu Phe Asp Arg Cys Lys Pro Tyr Ser Tyr Pro Pro Leu Leu Pro
            840                 845                 850 gaa tgt aac cct gag ttt ata aat cag atg caa cca tcc tct tgc cac      2827
Glu Cys Asn Pro Glu Phe Ile Asn Gln Met Gln Pro Ser Ser Cys His
        855                 860                 865 cac aat cag atg gtc gat tac aat aac atg aac acg agc acg agt act      2875
His Asn Gln Met Val Asp Tyr Asn Asn Met Asn Thr Ser Thr Ser Thr
    870                 875                 880 acc atg aat cct agc atg aat cct ccc ctt acg cct gaa ata gca tcc      2923
Thr Met Asn Pro Ser Met Asn Pro Pro Leu Thr Pro Glu Ile Ala Ser
885                 890                 895                 900 agc caa agt gga ttc ggc aga aaa cat cgc aaa tgt cat caa gcg cat      2971
Ser Gln Ser Gly Phe Gly Arg Lys His Arg Lys Cys His Gln Ala His
                905                 910                 915 caa ttt gag ttc cac att gat acc ggg aca atc gat ttg gtc gaa gat      3019
Gln Phe Glu Phe His Ile Asp Thr Gly Thr Ile Asp Leu Val Glu Asp
            920                 925                 930 ttg ggc att tgg gtg atc ttc aaa atc tgt gcc aca gat gga tac gca      3067
Leu Gly Ile Trp Val Ile Phe Lys Ile Cys Ala Thr Asp Gly Tyr Ala
        935                 940                 945 agc tta gat gat ctg gaa gtg att gaa gaa gga gcg ctg ggt gtc gaa      3115
Ser Leu Asp Asp Leu Glu Val Ile Glu Glu Gly Ala Leu Gly Val Glu
```

-continued

```
             950                  955                  960
gca tta gaa ctt gtc aaa aaa aga gaa aag aaa tgg aga cat cag aag        3163
Ala Leu Glu Leu Val Lys Lys Arg Glu Lys Lys Trp Arg His Gln Lys
965                 970                  975                  980 gag cag cac tgt tcg caa acg aaa cac aaa tat gat gcg gcc aaa cat        3211
Glu Gln His Cys Ser Gln Thr Lys His Lys Tyr Asp Ala Ala Lys His
                985                  990                  995 gcg gtg atg gcg tta ttt aca aac aag cgc tat gaa aaa ttg aag ttc        3259
Ala Val Met Ala Leu Phe Thr Asn Lys Arg Tyr Glu Lys Leu Lys Phe
        1000                 1005                 1010 gaa aca acc att tct gac att ttg tat gct gat cat ctc gtg cag tcg        3307
Glu Thr Thr Ile Ser Asp Ile Leu Tyr Ala Asp His Leu Val Gln Ser
    1015                 1020                 1025 att cct tat gta tat aat aaa tat gta ccg gaa gtt cca ggt atg aat        3355
Ile Pro Tyr Val Tyr Asn Lys Tyr Val Pro Glu Val Pro Gly Met Asn
1030                 1035                 1040 tac gaa ctc tat tca gag cta aac aca ctg gtt cag aat gcg ttc tac        3403
Tyr Glu Leu Tyr Ser Glu Leu Asn Thr Leu Val Gln Asn Ala Phe Tyr
1045                 1050                 1055                 1060 ctg tat gac cag cgg aat ctg att aaa aat ggg cgc ttt agc aat ggg        3451
Leu Tyr Asp Gln Arg Asn Leu Ile Lys Asn Gly Arg Phe Ser Asn Gly
            1065                 1070                 1075 ctt atg cat tgg caa gct act cct cat gca aga gta gag caa gaa tat        3499
Leu Met His Trp Gln Ala Thr Pro His Ala Arg Val Glu Gln Glu Tyr
        1080                 1085                 1090 gag aaa tcg gtg ctc gtg ctg cca aat tgg gat gcc aat gtg tcg caa        3547
Glu Lys Ser Val Leu Val Leu Pro Asn Trp Asp Ala Asn Val Ser Gln
    1095                 1100                 1105 gat ctt tgt atc gaa cac aat cgc ggt tat gta ttg cgt gtc acg gcg        3595
Asp Leu Cys Ile Glu His Asn Arg Gly Tyr Val Leu Arg Val Thr Ala
1110                 1115                 1120 aga aaa gaa gat ccg gga gct ggc aat gtt acc ttt agt gac tgt gaa        3643
Arg Lys Glu Asp Pro Gly Ala Gly Asn Val Thr Phe Ser Asp Cys Glu
1125                 1130                 1135                 1140 aat cat gtc gac aag ctg agc ttt act tct tgc gat ata gct aca aac        3691
Asn His Val Asp Lys Leu Ser Phe Thr Ser Cys Asp Ile Ala Thr Asn
            1145                 1150                 1155 gca gtg cca ggt gcc caa gcg aat gat cca gcc gcc gga gta gcc tat        3739
Ala Val Pro Gly Ala Gln Ala Asn Asp Pro Ala Ala Gly Val Ala Tyr
        1160                 1165                 1170 gga caa cag ggt tgt caa ata gat aga gtg ccg tac ggg caa tct gga        3787
Gly Gln Gln Gly Cys Gln Ile Asp Arg Val Pro Tyr Gly Gln Ser Gly
    1175                 1180                 1185 tat cga gca gac gga gta gcg tac gaa cag tct ggt cat cga aca gat        3835
Tyr Arg Ala Asp Gly Val Ala Tyr Glu Gln Ser Gly His Arg Thr Asp
1190                 1195                 1200 gga gtg ccg tac aga caa tct gga tat gga aca gac gga gta acg tac        3883
Gly Val Pro Tyr Arg Gln Ser Gly Tyr Gly Thr Asp Gly Val Thr Tyr
1205                 1210                 1215                 1220 gaa caa tct ggt cat cga gca gat gga gtg ccg tac gga caa tct gga        3931
Glu Gln Ser Gly His Arg Ala Asp Gly Val Pro Tyr Gly Gln Ser Gly
            1225                 1230                 1235 tat cga gca gat gga gta gcg tac gaa cag tct ggt cat cga gca gat        3979
Tyr Arg Ala Asp Gly Val Ala Tyr Glu Gln Ser Gly His Arg Ala Asp
        1240                 1245                 1250 gga gtg ccg tac gga caa tct gga tat gga aca gac gga gta acg tac        4027
Gly Val Pro Tyr Gly Gln Ser Gly Tyr Gly Thr Asp Gly Val Thr Tyr
    1255                 1260                 1265 gac caa tct gcc aat caa acc cgc aaa tat cat ggt tgc cat aca gac        4075
```

-continued

```
Asp Gln Ser Ala Asn Gln Thr Arg Lys Tyr His Gly Cys His Thr Asp
    1270                1275                1280 gga ctg cca cat cca gag cat ggt tgt tgt tat cca gac aga gta agc      4123
Gly Leu Pro His Pro Glu His Gly Cys Cys Tyr Pro Asp Arg Val Ser
1285                1290                1295                1300 gat ggc caa cag ctt gca tat gta aca aaa tcg att gat ctg ttc ccg      4171
Asp Gly Gln Gln Leu Ala Tyr Val Thr Lys Ser Ile Asp Leu Phe Pro
                1305                1310                1315 gat aca gat aaa gtc cgg atc gac att gga gaa acc gaa ggg aac ttt      4219
Asp Thr Asp Lys Val Arg Ile Asp Ile Gly Glu Thr Glu Gly Asn Phe
            1320                1325                1330 aga gtg gaa agt gtg gaa ttg att tgt atg gaa aag taaatcatca           4265
Arg Val Glu Ser Val Glu Leu Ile Cys Met Glu Lys
        1335                1340 caagtaaaag tatcgtttac taaaaattta ttttccaagc aacaggggag aagatgattt   4325
gggtgtaata ctcaaatcat cttttcttat aagccacttt a                        4366

<210> SEQ ID NO 20
<211> LENGTH: 1344
<212> TYPE: PRT
<213> ORGANISM: Bacillus popilliae

<400> SEQUENCE: 20

Met Asn Gln Tyr His Asn Gln Asn Asp Asn Lys Ser Tyr Asn Gln Ser
  1               5                  10                  15

Gly Asn Glu Met Gln Ile Ile Gln Pro Ser Ser Asn Ser Leu Leu Tyr
            20                  25                  30

Ser Pro Asn Lys Tyr Pro Tyr Ala Thr Asp Pro Asn Val Ile Ala Glu
        35                  40                  45

Gly Arg Ser Tyr Lys Asn Trp Leu Asp Met Cys Val Gly Glu Gly Asp
     50                  55                  60

Gly Thr Arg Ser Leu Glu Ala Ile Ala Val Ala Val Gly Val Arg Ile
 65                  70                  75                  80

Ser His Thr Ile Phe Arg Leu Leu Gly Val Pro Tyr Ser Ala Gln Gly
                 85                  90                  95

Glu Gln Leu Phe Ser Phe Leu Leu Asp Thr Leu Trp Leu Glu Gly Asn
            100                 105                 110

Thr Gln Trp Glu Glu Leu Met Arg His Ala Glu Glu Leu Ile Asn Glu
        115                 120                 125

Gln Val Pro Asp Tyr Val Arg Thr Lys Ala Leu Ala Glu Leu Thr Asp
    130                 135                 140

Leu Gly Asn Asn Leu Asn Leu Tyr Ile Ala Ala Phe Glu Asp Trp Lys
145                 150                 155                 160

Arg Asn Pro Ser Ser Gln Glu Val Arg Thr Arg Val Ile Asp Arg Phe
                165                 170                 175

Asn Ile Leu Asp Gly Leu Phe Glu Ala Tyr Leu Pro Ser Phe Ala Val
            180                 185                 190

Pro Gly Tyr Glu Val Pro Leu Leu Ser Val Tyr Ala Asn Val Val Asn
        195                 200                 205

Ile His Leu Leu Val Leu Arg Asp Ser Ser Ile Tyr Gly Leu Asp Trp
    210                 215                 220

Gly Leu Ser Ser Thr Ser Val Asp Asn Asn Tyr Asn Arg Gln Gln Arg
225                 230                 235                 240

Asn Ser Ala Thr Tyr Ala Asn His Cys Thr Thr Trp Tyr Gln Thr Gly
                245                 250                 255
```

-continued

```
Leu Gln Arg Leu Gln Gly Ser Asp Ala Ser Ser Trp Val Asn Tyr Asn
            260                 265                 270

Arg Phe Arg Arg Glu Ile Thr Leu Ile Val Leu Asp Ile Cys Ala Leu
        275                 280                 285

Phe Ser Asn Tyr Asp Val Arg Ser Tyr Pro Ile Gln Leu Arg Gly Glu
    290                 295                 300

Leu Thr Arg Gly Ile Tyr Thr Asp Pro Ala Val Tyr Ser Gly Thr Gly
305                 310                 315                 320

Ser Tyr Ser Trp Leu Ser Gln Ala Pro Ser Phe Ala Glu Ile Glu Asn
                325                 330                 335

Ile Ala Ile Arg Glu Pro Ser Asn Phe Thr Trp Ala Ser Tyr Ala Arg
            340                 345                 350

Val Thr Thr Gly Thr Leu Glu Tyr Leu Ser Ser Lys Asn Asp Phe Trp
        355                 360                 365

Lys Ser His Tyr Met Asn Tyr Thr Glu Thr Asn Ser Gly Ile Leu Ile
    370                 375                 380

Gln Gly Pro Thr Tyr Gly Met Thr Thr Gly Thr Asn Ile Arg Ile Glu
385                 390                 395                 400

Ser Val Ser Met Gln Glu Ile Tyr Ser Val Arg Leu Glu Ala Val Ala
                405                 410                 415

His Ala Gly Ala Gly Gly Pro Phe Leu Gly Ile Ser Thr Ser Glu Phe
            420                 425                 430

Phe Trp Ser Leu Gly Val Arg Arg Tyr Gln Asn Ser Arg Ser Pro Gln
        435                 440                 445

Phe Ala Ser Gln Ile Ile Thr Arg Gln Leu Pro Gly Val Asn Ser Ala
    450                 455                 460

Val Pro Ser Ala Leu Asp His Ser His Glu Leu Ser Tyr Ile Thr Ala
465                 470                 475                 480

Phe Pro Val Arg Ser Val Gly Thr Ile Leu Val His Glu Trp Thr Ser
                485                 490                 495

Thr Thr Val Ser Arg Asn Asn Arg Ile Glu Pro Asp Lys Ile Thr Gln
            500                 505                 510

Ile Pro Ala Val Lys Ser His Thr Leu Ser Asn Cys Gln Val Val Ser
        515                 520                 525

Gly Thr Gly Phe Thr Gly Gly Asn Trp Leu Arg Pro Ser Asp Asn Gly
    530                 535                 540

Ser Phe Arg Leu Thr Ile Thr Ser Phe Ser Ser Gln Ser Tyr Arg Ile
545                 550                 555                 560

Arg Ile His Tyr Ala Ser Ala Thr Phe Phe Tyr Leu Asp Ile Arg Thr
                565                 570                 575

Gly Asp Thr Ser Asn Thr Phe Ala Val Thr Pro Thr Thr Leu Ser Ser
            580                 585                 590

Gly Ser Gln Thr Val Pro Tyr Glu Ser Phe Gly Phe Ile Asn Ile Pro
        595                 600                 605

Tyr Thr Phe Thr Thr Ala Pro Thr Glu Ser Arg Tyr Thr Phe Asp Phe
    610                 615                 620

Met Phe Tyr Ser Ile Gly Ser Ala Asn Val Leu Ile Asp Arg Ile Glu
625                 630                 635                 640

Ile Val Pro Ile Gly Val Pro Leu Phe Glu Tyr Glu Thr Lys Gln Gln
                645                 650                 655

Leu Glu Lys Ala Arg Lys Ala Val Asn His Leu Phe Thr Asp Gly Ser
            660                 665                 670

Lys Lys Ala Leu Lys Glu Asp Thr Thr Asp Tyr Glu Ile Asp Gln Ala
```

-continued

```
                675                 680                 685
Ala Asn Val Val Asp Cys Ile Ser Asp Glu Cys Gly His Asp Lys Met
690                 695                 700
Ile Leu Asp Glu Val Lys Tyr Ala Lys Gln Leu Ser Gln Ala Arg
705                 710                 715                 720
Asn Leu Leu Asn Gly Asn Phe Asp Asp Leu Tyr Ser Ala Leu Glu
                725                 730                 735
Lys Glu Asn Pro Trp Lys Thr Ser Pro Asn Val Thr Ile Arg Gln Asp
                740                 745                 750
Asn Pro Ile Phe Lys Gly His Tyr Leu Ser Met Ala Gly Ala Asn Asp
                755                 760                 765
Ile Glu Ala Thr Asn Asp Thr Phe Pro Thr Tyr Val Tyr Gln Lys Ile
                770                 775                 780
Asp Glu Ala Lys Leu Lys Pro Tyr Thr Arg Tyr Lys Val Arg Gly Phe
785                 790                 795                 800
Val Gly Ser Ser Lys Ala Leu Glu Leu Leu Val Thr Arg Tyr Asn Glu
                805                 810                 815
Glu Val Asp Ala Ile Leu Asp Val Pro Asp Asn Ile Pro His Ala Pro
                820                 825                 830
Thr Pro Val Cys Gly Glu Phe Asp Arg Cys Lys Pro Tyr Ser Tyr Pro
                835                 840                 845
Pro Leu Leu Pro Glu Cys Asn Pro Glu Phe Ile Asn Gln Met Gln Pro
                850                 855                 860
Ser Ser Cys His His Asn Gln Met Val Asp Tyr Asn Asn Met Asn Thr
865                 870                 875                 880
Ser Thr Ser Thr Thr Met Asn Pro Ser Met Asn Pro Pro Leu Thr Pro
                885                 890                 895
Glu Ile Ala Ser Ser Gln Ser Gly Phe Gly Arg Lys His Arg Lys Cys
                900                 905                 910
His Gln Ala His Gln Phe Glu Phe His Ile Asp Thr Gly Thr Ile Asp
                915                 920                 925
Leu Val Glu Asp Leu Gly Ile Trp Val Ile Phe Lys Ile Cys Ala Thr
                930                 935                 940
Asp Gly Tyr Ala Ser Leu Asp Asp Leu Glu Val Ile Glu Glu Gly Ala
945                 950                 955                 960
Leu Gly Val Glu Ala Leu Glu Leu Val Lys Arg Glu Lys Lys Trp
                965                 970                 975
Arg His Gln Lys Glu Gln His Cys Ser Gln Thr Lys His Lys Tyr Asp
                980                 985                 990
Ala Ala Lys His Ala Val Met Ala Leu Phe Thr Asn Lys Arg Tyr Glu
                995                 1000                1005
Lys Leu Lys Phe Glu Thr Thr Ile Ser Asp Ile Leu Tyr Ala Asp His
                1010                1015                1020
Leu Val Gln Ser Ile Pro Tyr Val Tyr Asn Lys Tyr Val Pro Glu Val
1025                1030                1035                1040
Pro Gly Met Asn Tyr Glu Leu Tyr Ser Glu Leu Asn Thr Leu Val Gln
                1045                1050                1055
Asn Ala Phe Tyr Leu Tyr Asp Gln Arg Asn Leu Ile Lys Asn Gly Arg
                1060                1065                1070
Phe Ser Asn Gly Leu Met His Trp Gln Ala Thr Pro His Ala Arg Val
                1075                1080                1085
Glu Gln Glu Tyr Glu Lys Ser Val Leu Val Leu Pro Asn Trp Asp Ala
                1090                1095                1100
```

-continued

```
Asn Val Ser Gln Asp Leu Cys Ile Glu His Asn Arg Gly Tyr Val Leu
1105                1110                1115                1120

Arg Val Thr Ala Arg Lys Glu Asp Pro Gly Ala Gly Asn Val Thr Phe
                1125                1130                1135

Ser Asp Cys Glu Asn His Val Asp Lys Leu Ser Phe Thr Ser Cys Asp
            1140                1145                1150

Ile Ala Thr Asn Ala Val Pro Gly Ala Gln Ala Asn Asp Pro Ala Ala
        1155                1160                1165

Gly Val Ala Tyr Gly Gln Gln Gly Cys Gln Ile Asp Arg Val Pro Tyr
    1170                1175                1180

Gly Gln Ser Gly Tyr Arg Ala Asp Gly Val Ala Tyr Glu Gln Ser Gly
1185                1190                1195                1200

His Arg Thr Asp Gly Val Pro Tyr Arg Gln Ser Gly Tyr Gly Thr Asp
                1205                1210                1215

Gly Val Thr Tyr Glu Gln Ser Gly His Arg Ala Asp Gly Val Pro Tyr
            1220                1225                1230

Gly Gln Ser Gly Tyr Arg Ala Asp Gly Val Ala Tyr Glu Gln Ser Gly
        1235                1240                1245

His Arg Ala Asp Gly Val Pro Tyr Gly Gln Ser Gly Tyr Gly Thr Asp
    1250                1255                1260

Gly Val Thr Tyr Asp Gln Ser Ala Asn Gln Thr Arg Lys Tyr His Gly
1265                1270                1275                1280

Cys His Thr Asp Gly Leu Pro His Pro Glu His Gly Cys Cys Tyr Pro
                1285                1290                1295

Asp Arg Val Ser Asp Gly Gln Gln Leu Ala Tyr Val Thr Lys Ser Ile
            1300                1305                1310

Asp Leu Phe Pro Asp Thr Asp Lys Val Arg Ile Asp Ile Gly Glu Thr
        1315                1320                1325

Glu Gly Asn Phe Arg Val Glu Ser Val Glu Leu Ile Cys Met Glu Lys
    1330                1335                1340

<210> SEQ ID NO 21
<211> LENGTH: 34
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 21
ctggaattca tgaatcagta tcataaccaa aacg                               34

<210> SEQ ID NO 22
<211> LENGTH: 34
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 22
gagctgcagt tacttttcca tacaaatcaa ttcc                               34
```

US 7,544,502 B2

POLYNUCLEOTIDE ENCODING POLYPEPTIDE HAVING LARVAE GROWTH INHIBITING OR INSECTICIDAL EFFECT ON SCARABAEIDAE INSECTS

This application is a Divisional of prior application Ser. No. 10/120,544 which is now U.S. Pat. No. 7,033,993 filed on Apr. 12, 2002, which is hereby incorporated by reference.

BACKGROUND OF THE INVENTION

1. Field of the Invention

The present invention relates to polypeptides having larvae growth inhibiting or insecticidal effect on Scarabaeidae insects, to polynucleotides encoding the same, to controlling agents for controlling Scarabaeidae insects containing the polypeptides as active ingredients, and to a method of controlling Scarabaeidae insects using the polypeptides.

2. Description of the Related Art

Larvae of Scarabaeidae insects eat roots of a wide variety of plants such as turf, agricultural crops, horticultural crops and trees and bushes and cause serious damage thereto. A large number of reports have been made on damages caused by, especially, *Anomala cuprea, Blitopertha orientalis*, and *Popillia japonica* to a lawn of golf courses, a sweet potato field, and a peanut field. In particular, *Anomala cuprea*, which is particularly large in size, does considerable harm thereto due to its eager appetite.

However, conventional ground spreading of chemical pesticides is difficult to give a controlling effect since these larvae inhabit in the ground and are difficult to locate them, and thus it was necessary to spread a large amount of chemical pesticides over a wide range of the surface of the ground and penetrate them into the ground. Therefore, there were concerns about adverse influences of the chemical pesticides on the natural environment and human bodies, and there has been a keen desire for a biological controlling method that can replace the chemical pesticides.

As one of the biological controlling methods for controlling Scarabaeidae insects, attempts to utilize bacteria belonging to *Bacillus popilliae* have been tried over a long period of time. The bacteria are parasitic to larvae of Scarabaeidae insects as hosts and infect to them per os usually in a form of sporangia, propagate in large amounts in hemolymph to cause milky disease and finally lead the larvae to death.

Recently, an amino acid sequence of a polypeptide constituting a parasporal body of a strain belonging to *Bacillus popilliae*, i.e., *Bacillus popilliae* subsp. *melolonthae* H1, and a nucleotide sequence of the gene encoding the polypeptide were partly clarified (J. Bacteriol. Vol. 179, p.4336-4341 (1997)), and it has been reported that the polypeptide constituting the parasporal body of *Bacillus popilliae* subsp. *melolonthae* H1 has a controlling effect on *Melolontha melolontha* (WO97/14798). However, it was not clarified whether the bacterial strain and a polypeptide thereof have controlling effects on *Anomala cuprea, Blitopertha orientalis* and *Poplillia japonica*, each of which belongs to different species.

SUMMARY OF THE INVENTION

An object to be solved according to the present invention is to provide polypeptides having a larvae growth inhibiting effect or an insecticidal effect on Scarabaeidae insects, in particular *Anomala cuprea, Blitopertha orientails* and *Poplillia japonica*, transformants having introduced therein a polynucleotide encoding the polypeptide, controlling agents for Scarabaeidae insects containing the polypeptides as active ingredients, controlling agents for Scarabaeidae insects using the polypeptide and sporangia of *Bacillus popilliae*, and a method of controlling Scarabaeidae insects using the controlling agents.

The inventors of the present invention have found that the sporangia of certain strains belonging to *Bacillus popilliae* have a larvae growth inhibiting effect or an insecticidal effect. Subsequently, they have taken out the parasporal body from sporangia of *Bacillus popilliae* (FIG. 1) containing a spore and a parasporal body, performed screening using an antibody to the polypeptide constituting the parasporal body to thereby isolate a polynucleotide encoding the polypeptide and determined its nucleotide sequence and amino acid sequence. A transformant having introduced therein the polynucleotide by using a vector enabled mass production of the above-mentioned polypeptide. Further, the inventors of the present invention have made it clear that the polypeptide produced by the transformant has a controlling effect on *Anomala cuprea* and further that use of the polypeptide in combination with the sporangia increases the controlling effect. Thus, the present invention was accomplished.

Therefore, according to the present invention, there is provided (1) a polypeptide having the amino acid sequence of SEQ ID NO: 2, or the amino acid sequence including substitution, deletion or insertion of one or several numbers of amino acid residues and having a larvae growth inhibiting or insecticidal effect on a Scarabaeidae insect.

According to the present invention, there is provided (2) a polypeptide having the amino acid sequence of SEQ ID NO: 4, 6, 18 or 20, or the amino acid sequence including substitution, deletion or insertion of one or several numbers of amino acid residues, the polypeptide having a larvae growth inhibiting or insecticidal effect on a Scarabaeidae insect.

According to the present invention, there is provided (3) a polypeptide having the amino acid sequence of SEQ ID NO: 8 or 10, or the amino acid sequence including substitution, deletion or insertion of one or several numbers of amino acid residues, the polypeptide having a larvae growth inhibiting or insecticidal effect on a Scarabaeidae insect.

Further, the present invention provides polynucleotides encoding the polypeptides.

Still further, the present invention provides vectors comprising the polynucleotides and transformants which are introduced the polynucleotides.

Further, the present invention provides controlling agents for controlling a Scarabaeidae insect containing the polypeptides as active ingredients.

Further, the present invention provides controlling agents for controlling a Scarabaeidae insect comprising the polypeptides and sporangia of bacteria belonging to *Bacillus popilliae* as active ingredients.

Still further, the present invention provides a method of controlling a Scarabaeidae insect, in which the Scarabaeidae insect is subjected to an action of the controlling agent for controlling a Scarabaeidae insect.

In the present invention, the term "polypeptide" includes peptides consisting of a plurality of amino acids linked through peptide bonds and polypeptides to which other molecules such as glycoproteins are bonded as well as proteins in a form of multimers, etc.

According to the present invention, polypeptides having a larvae growth inhibiting or an insecticidal effect on Scarabaeidae insects, in particular *Anomala cuprea, Blitopertha orientalis* and *Popilliae japonica*, transformants having introduced therein a polynucleotide encoding the polypeptide, a controlling agent for controlling a Scarabaeidae insect comprising the polypeptide as an active ingredient, and a method of controlling a Scarabaeidae insect using the polypeptide and sporangia of *Bacillus popilliae* as active ingredients.

BRIEF DESCRIPTION OF THE SEVERAL VIEWS OF THE DRAWINGS

FIG. 5 shows alignment of amino acid sequences in Example 11;

FIG. 6 shows alignment of amino acid sequences in Example 11;

FIG. 7 shows alignment of amino acid sequences in Example 11;

DETAILED DESCRIPTION OF THE INVENTION

Figure 1:
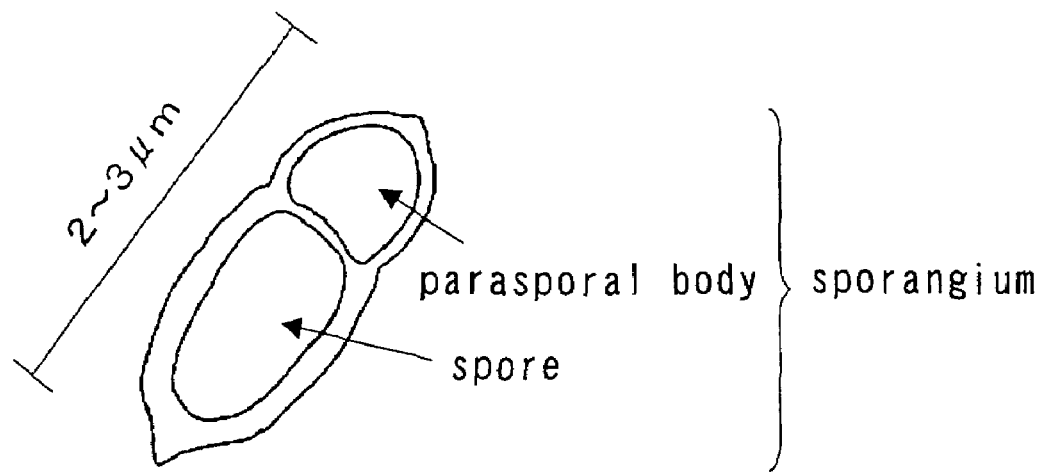
FIG. 1 is a schematic diagram of a sporangium containing a spore and a parasporal body.

Hereinafter, the present invention will be described in detail.

A parasporal body contained in sporangia of a bacterium belonging to *Bacillus popilliae* is a proteinaceous aggregate (Hukuhara, Toshihiko, "Insect Pathology", p. 57, 1979), which comprises one kind or plural kinds of polypeptides. The polypeptide of the present invention is one or more polypeptides that constitute the parasporal body in the sporangium of *Bacillus popilliae semadara* or the like that will be described below. However, the polypeptide of the present invention is different in the amino acid sequence from a polypeptide that constitutes a parasporal body described in WO97/14798, and hence the polypeptide and polynucleotide of the present invention are considered to be novel.

According to a first aspect of the present invention, there is provided a polypeptide having the amino acid sequence of SEQ ID NO: 2 and having a larvae growth inhibiting effect or an insecticidal effect on a Scarabaeidae insect.

According to a second aspect of the present invention, there is provided a polypeptide having the amino acid sequence of SEQ ID NO: 4, 6, 18 or 20 and having a larvae growth inhibiting effect or an insecticidal effect on a Scarabaeidae insect.

According to a third aspect of the present invention, there is provided a polypeptide having the amino acid sequence of SEQ ID NO: 8 or 10 and having a larvae growth inhibiting effect or an insecticidal effect on a Scarabaeidae insect.

Note that the amino acid sequence of SEQ ID NO: 2 and the nucleotide sequence of SEQ ID NO: 1 are sequences found in the amino acid sequences of SEQ ID NO: 4, 6, 18 or 20 and the nucleotide sequences of SEQ ID NO: 3, 5, 17 or 19 with homology of 95% or more and is considered to be specific to the parasporal body of *Bacillus popilliae* (cf. Example 11).

The above-mentioned polypeptide of the present invention may include polypeptides containing substitution, deletion or insertion of one or several numbers of amino acid residues as far as the polypeptides have a larvae growth inhibiting effect or an insecticidal effect on a Scarabaeidae insect. Here, the term "several numbers of" means, specifically, a number of from 2 to 100, preferably from 2 to 50, and more preferably from 2 to 9, although it may vary depending on the position and kinds of amino acid residues in a three-dimensional structure of the polypeptide. These polypeptides including substitution, deletion or insertion of one or several numbers of amino acid residues can be obtained, for example, by introducing a mutation to a polynucleotide encoding the polypeptide by site-specific mutatagenesis and performing transcription and translation of the polynucleotide. These polypeptides of the present invention may be fused polypeptides with other polypeptides. The polypeptides of the present invention may be polypeptides that have the amino acid sequence having homology of 50% or more, preferably 70% or more, and more preferably 90% or more, with the above-mentioned amino acid sequence as far as the polypeptides have a larvae growth inhibiting effect or an insecticidal effect on a Scarabaeidae insect. Further, the polypeptides of the present invention may be polypeptides that have a part of the amino acid sequence of SEQ ID NO: 4, 6, 18 or 20 as far as the polypeptides have a larvae growth inhibiting effect or an insecticidal effect on a Scarabaeidae insect.

The polynucleotides of the present invention are polynucleotides that encode the above-mentioned polypeptides of the present invention. Codons of each of amino acid residues are not particularly limited as far as the amino acid sequence encoded is the same. Specific examples of the polynucleotide of the present invention include a polynucleotide comprising the nucleotide sequence of SEQ ID NO: 1, a polynucleotide having the nucleotide sequence of the coding region of SEQ ID NO: 3, 5, 17 or 19, and a polynucleotide having the nucleotide sequence of SEQ ID NO: 7 or 9.

The polynucleotide of the present invention may be a polynucleotide that is hybridizable under the stringent conditions to each of the above-mentioned polynucleotide or a probe that can be prepared from the above-mentioned polynucleotide as far as they encode polypeptides having a larvae growth inhibiting effect or an insecticidal effect on a Scarabaeidae insect. The term "the stringent conditions" used herein refers to a condition under which a so-called specific hybrid is formed and nonspecific hybrid is not formed. Such a condition is a condition in which DNAs having high homology, for example, DNAs having homology of 50% or more, preferably 70% or more, and more preferably 90% or more, are hybridized and DNAs having homology that is lower than the above-are not hybridized. Specifically, it includes a condition of 40° C., 1×SSC (0.15 M NaCl, 15 mM Sodium Citrate, pH 7.0) and 0.1% SDS (Sodium Dodecyl Sulfate).

The polynucleotides of the present invention can be obtained from, for example, bacteria belonging to *Bacillus popilliae*, more specifically from *Bacillus popilliae semadara*, FERM P-16818, *Bacillus popilliae var. Mame*, FERM P-17661, *Bacillus popilliae var. popilliae Hime*, FERM P-17660, *Bacillus popilliae var. popilliae Sakura*, FERM P-17662, and *Bacillus popilliae Dutky*, American Type Culture Collection No. 14706 by the following methods.

*Bacillus popilliae semadara*, FERM P-16818 has been deposited by Chiba-ken (1-1, Ichiba-cho, Chuo-ku, Chiba-shi, Chiba-ken, Japan) since May 21, 1998 in National Institute of Bioscience and Human Technology of Agency of Industrial Science and Technology of Ministry of International Trade and Industry (1-3 Hagashi 1-Chome, Tasukuba-shi, Ibaraki-ken 305-8566 Japan) (currently, National Institute of Advanced Industrial Science and Technology International Patent Organism Depository, Tsukuba Central 6, 1-1, Hagashi 1-Chome, Tsukuba-shi, Ibaraki-ken, 305-

8566, Japan), and the original deposit was converted to international deposit based on the Budapest Treaty on Jun. 10, 2002, and assigned the deposition number of FERM BP-8068.

*Bacillus popilliae var. Mame.* FERM P-17661 has been deposited by the applicant of the application since Nov. 25, 1999 in National Institute of Bioscience and Human Technology of Agency of Industrial Science and Technology of Ministry of International Trade and Industry (1-3, Hagashi 1 -Chome, Tsukuba-shi, Ibaraki-ken, 305-8566, Japan) (currently, National Institute of Advanced Industrial Science and Technology, International Patent Organism Depository, Tsukuba Central 6, 1-1, Hagashi 1-Chome, Tsukuba-shi, Ibaraki-ken, 305-8566, Japan), and the original deposit was converted to international deposit based on the Budapest Treaty on Jun. 10, 2002, and assigned the deposition number of FERM BP-8069.

One method of obtaining them includes a screening method by utilizing an antibody. That is, an antibody to a purified parasporal body is prepared in advance. On the other hand, a chromosomal DNA of the above-mentioned bacterial strain is collected, cleaved with an appropriate restriction enzyme and inserted into an expression vector to prepare a chromosomal DNA library. Then, the library is expanded in *Escherichia coli* or the like and screened by Western blotting utilizing the above-mentioned antibody.

Another method of obtaining the polynucleotides of the present invention includes a PCR method. An appropriate nucleotide sequence is selected from nucleotide sequences of SEQ ID NOs: 11 to 16, 21 and 22 and nucleotide sequences obtained by adding modifications thereto and partial nucleotide sequences derived from the nucleotide sequences of SEQ ID NOs: 1, 3, 5, 7, 9, 17 and 19, and two kinds of polynucleotides directing opposite to each other are provided. PCR is performed using the polynucleotides as primers and a chromosomal DNA as a template. By cloning an amplified DNA fragment, the polynucleotides of the present invention can be obtained.

Note that PCR using oligonucleotides having respective nucleotide sequences of SEQ ID NOS: 11 and 13 as primers and a chromosomal DNA of *Bacillus popilliae semadara* as a template can give rise to polynucleotide amplified fragments of about 4.2 kb having the nucleotide sequences of SEQ ID NOS: 17 and 19, respectively. The nucleotide sequences of these polynucleotides exist adjacent to each other on the chromosomal DNA of *Bacillus popilliae semadara* and the amino acid sequences (SEQ ID NOS: 18 and 20) of the polypeptides encoded by the polynucleotides have homology of about 73% to each other, which strongly suggests that both the polynucleotides have similar functions.

Also, the polynucleotides having the nucleotide sequences of SEQ ID NOS: 3, 5, 7, and 9 obtained by PCR using a chromosomal DNA of *Bacillus popilliae var. popilliae Mame* as a template and polypeptides having amino acid sequences of SEQ ID NOS: 4, 6, 8 and 10, which are translation products thereof, have high homology to the nucleotide sequence of the polynucleotide of *Bacillus popilliae semadara* and the polypeptide encoded by the polynucleotide (homology of 61 to 88% for the polynucleotide and 59 to 98% for the polypeptide). This suggests that they also have similar functions.

Further, another method of obtaining the polynucleotides of the present invention includes a hybridization method. After digesting the chromosomal DNA with an appropriate restriction enzyme, a genome library is prepared by utilizing a plasmid vector or a phage vector or the like. On the other hand, appropriate polynucleotide probes having the nucleotide sequences of SEQ ID NOS: 11 to 16, 21 and 22 or nucleotide sequences obtained by adding modifications thereto, or partial nucleotide sequences derived from the nucleotide sequences of SEQ ID NOS: 1, 3, 5, 7, 9, 17 and 19 are provided. By colony hybridization or plaque hybridization in which a library prepared in *Escherichia coli* or the like by using the vector is screened with a labeled probe, the polynucleotide of the present invention can be obtained.

The vectors that can be used in the present invention include plasmid vectors, Ti plasmid vectors, phage vectors, phagemid vectors, YAC vectors, virus vectors and the like. The vectors may include, in addition to the polynucleotides of the present invention, sequences that regulate or assist expression of polypeptides (for example, a promoter, an operator, a terminator, an enhancer, and an SD sequence) or marker gene for selecting transformant hosts (for example, an ampicillin resistance gene, a tetracycline resistance gene, a kanamycin resistance gene, and a neomycin resistance gene) and the like. The vectors may comprise plural kinds of polynucleotides of the present invention or a plurality of molecules of the same polynucleotide.

The hosts that can be used in the present invention include microbes (for example, bacteria such as *Escherichia coli*, *Pseudomonad*, and *Bacillus*, actinomycetes such as *Streptomyces*, Fungi such as molds and yeasts), plants (for example, turf, sweet potatoes, tobaccos, rice plants, and corn), cultured cells (for example, plant cultured cells such as a tobacco cultured cell, insect cultured cells such as a silkworm moth cultured cell and animal cultured cells such as mouse cultured cell) and the like.

In the present invention, conventional methods used in genetic engineering can be used in the procedure of constructing a vector and transformation operation of hosts with the vector. For example, the transformation method includes a calcium chloride method, an electroporation method, a PEG method and the like for microbe hosts, an electroporation method, a particle gun method, an agrobacterium method and the like for cultured cells and plant hosts.

In a case where the host is a microbe or a cultured cell, the method of producing a polypeptide of the present invention can be performed by culturing the microbe or the cultured cell in an appropriate medium and recover the produced polypeptide from the culture. The culture method of culturing a transformed host may be substantially the same as the culture method for the host to be used. Extraction of the polypeptide from the culture and purification thereof, if necessary, may be performed by usually employed methods. On the other hand, in a case where the host is a plant, the transformed plant is grown by the same methods as the methods usually used, and a polypeptide can be extracted from the plant body. From a different standpoint, the transformed plant and its seeds may be provided as is as insect resistant cultigen species. In addition, there is a production method of a polypeptide without using any transformant. It includes, for example, an in vitro cell-free transcription/translation system utilizing a wheat germ extract or an *Escherichia coli* extract. A polypeptide can be produced by adding a DNA fragment or an RNA fragment, or a vector containing the polynucleotide of the present invention to the transcription/translation system, thereby performing a conventional method for producing a polypeptide.

The polypeptides of the present invention have a larvae growth inhibiting or insecticidal activity on Scarabaeidae insects and exhibit controlling effects thereon. For this reason, the polypeptides can be applied to turf, agricultural crops or trees as a controlling agent or an active ingredient thereof for the purpose of controlling Scarabaeidae insects. Use of the polypeptides of the present invention in combination with spores or sporangia containing spores and parasporal bodies of bacteria belonging to *Bacillus popilliae* can further increase the larvae growth inhibiting or insecticidal activity on Scarabaeidae insects.

The Scarabaeidae insects that are the target of control with the polypeptides of the present invention include *Anomala cuprea, Blitopertha orientails, Popillia japonica, Phyllopertha diversa, Adoretus tenuimaculatus, Anomala rufocuprea* and the like. The polypeptides of the present invention are particularly effective on *Anomala cuprea* and *Blitopertha orientalis*.

As the controlling agent of the present invention, the polypeptides produced by the above-mentioned production method may be used as they are in the form of the transformants, as a purified product after isolation or as mixtures of these with substances used for culture/reaction systems of these. Alternatively, they may be used by adding excipients, carriers, nutritive agents, stabilizers and the like known and commonly used in agricultural chemicals to convert them into an optional preparation form such as dust, wettable powder, or a flowable agent.

The above-mentioned optional component includes: mineral fine powders such as kaolin clay, bentonite, montmorillonite, diatomaceous earth, acid clay, talcs, pearlite, and vermiculite, inorganic salts such as ammonium sulfate, urea, ammonium chloride, and ammonium nitrate, organic fine powders such as wheat bran, chitin, polysaccharides, rice bran, and flour, as solid carriers; fixing agents and dispersants such as casein, gelatin, gum Arabic, alginic acid, saccharides, synthetic polymers (polyvinyl alcohol, polyacrylic acids, etc.) as adjutants; and cryoprotectants such as propylene glycol and ethylene glycol, natural polysaccharides such as xanthan gum, thickeners such as polyacrylic acids as other components.

The ratio of the polypeptides of the present invention contained in the controlling agent is not particularly limited as far as they exhibit a controlling effect on Scarabaeidae insects, but it is preferably 0.0001 to 100 mass %.

The method of application of the controlling agent is selected as appropriate depending on the use form such as the preparation form, crops and the like and includes, for example, liquid dispersion on the ground, solid dispersion on the ground, liquid dispersion in the air, solid dispersion in the air, application in installations, application for mixing with soil, application for perfusion into soil, and the like methods.

Also, it is possible to apply the controlling agent of the present invention after mixing with other agents, i.e., pesticides, nematicides, acaricides, herbicides, microbicides, plant growth regulators, fertilizers, soil conditioning materials (peat, humic acid materials, polyvinyl alcohol-based materials, etc.) and the like, to apply it with alternately applying the other agents without mixing, or to apply it together with the other agents simultaneously.

The application amount of the controlling agent of the present invention cannot be uniquely defined since it may vary depending on the kind of Scarabaeidae insect, kind of plant to which the agent is applied, preparation form of the agent and the like. For example, the application amount of the polypeptide may be 0.01 to 100 $g/m^2$, preferably about 0.1 to 50 $g/m^2$ for dispersion on the ground.

Further, it is possible to use mixtures of the controlling agent of the present invention with other biocontrol agents or polypeptides derived from microbes (for example, the parasporal bodies of another strain of *Bacillus popilliae* or the parasporal bodies of *Bacillus thuringiensis*) or microbial spores (for example, spores of *Bacillus popilliae, Bacillus thuringiensis*, or *Bacillus subtilis*).

BEST MODE FOR CARRYING OUT THE INVENTION

Hereinafter, the present invention will be illustrated more specifically. However, the scope of the present invention is not limited thereto.

EXAMPLE 1

A suspension of sporangia of *Bacillus popilliae* prepared from larvae of *Anomala cuprea* infected with milky disease was subjected to treatment by a French press to take out spores and parasporal bodies from the sporangia. Only the parasporal bodies were recovered by a two-phase separation method by using sodium dextran sulfate (produced by Sigma Co., Ltd.), polyethylene glycol 6000 (produced by Wako Pure Chemical Industry Co., Ltd.) and NaCl and solubilized with 0.1 M NaOH and then subjected to SDS-PAGE. An about 135 kD band was cut out and pulverized to small pieces, which then were mixed with an adjuvant. The mixture was intradermally injected to a rabbit to immunize it.

To decrease the background upon screening a polypeptide gene clone that constitutes the parasporal body by using an antibody, absorption operation of the obtained antiserum with *Escherichia coil* fragments was repeated three times to remove the antibody that adsorbs on *Escherichia coli* itself and collect only the antibody that adsorbs on the polypeptide constituting the target parasporal body.

EXAMPLE 2

A chromosomal DNA was collected from the bacterial cells of *Bacillus popilliae semadara* by an ordinary method and digested with restriction enzyme EcoRI. This was ligated to phosphatase-treated pBluescript SK(+) and *Escherichia coli* DH5α was transformed with the ligation product. The transformants were spread over the LB agar plate so that 2,000 to 3,000 colonies could appear thereon.

A nitrocellulose membrane was closely contacted on the agar plate to transfer colonies on the membrane and the membrane was placed on a fresh agar plate so that the colonies-attached side of the membrane directs upward. The plate was incubated at 37° C. for 2 hours. For bacteriolysis of the bacterial cells on the membrane, the following operation was performed. That is, the membrane was transferred on a filter paper impregnated with 10% SDS and left to stand for 5 minutes. Then, the membrane was transferred on a filter paper impregnated with 0.2 M NaOH, 0.15 M NaCl and 1% β-mercaptoethanol and left to stand for 5 minutes and finally it was transferred on a filter paper impregnated with 0.15 M NaCl, 0.5 M Tris-HCl, and pH 7.5, and left to stand for 10 minutes. The membrane was transferred to a buffer solution (0.1 M Tris-HCl, pH 7.8, 0.15 M NaCl, 5 mM $MgCl_2$, 40 μg/ml lysozyme, and 5% skimmed milk) and shaken for 2 hours to remove the bacterial cells.

After washing the membrane with TBST (0.02 M Tris-HCl, pH 7.2, 0.5 M NaCl, and 0.05% Tween 20) for 5 minutes, the membrane was shaken for 1.5 hours in an anti-parasporal body antiserum solution diluted 8,000 folds with an antibody diluting liquid (TBST containing 5% skimmed milk). After repeating 10 minutes' washing with TBST three times, the membrane was transferred into a solution of 2,000-fold diluted Anti-Rabbit IgG (H&L), HRP-Linked (produced by New England Biolabs, Inc.) and incubated until color development was observed in an HRP coloring substrate (4CN, produced by NEN Life Science Products Co.).

Colonies near a site where strong coloring was observed, that is, to which the anti-parasporal body antiserum was adsorbed, were collected one by one from the master plate and the collected colonies were subjected to secondary screening performed in the same manner as described above to obtain a positive clone.

Plasmid was collected from the positive clone and the nucleotide sequence of the inserted portion was determined by an ordinary method. As a result, it revealed that the plasmid contained two polypeptide genes, which constitute the parasporal body of *Bacillus popilliae*, (SEQ ID NOS: 17 and 19, respective translation products being of SEQ ID NOS: 18 and 20) in a single cloned fragment. The amino acid sequence of SEQ ID NO: 18 and that of SEQ ID NO: 20 have about 73% of homology to each other. In this case, gene information processing software GENETYX-WIN (Software Development Co., Ltd.) is used for retrieval of the homology.

EXAMPLE 3

PCR was performed by using the plasmid of the above-mentioned positive clone as a template and polynucleotides having nucleotide sequences corresponding to parts of a polynucleotide of SEQ ID NO: 19 and a complementary strand thereof (SEQ ID NOS: 21 and 22, respectively) as primers. After electrophoresing the reaction solution, about 4 kb of amplified fragments were recovered and purified and digested with restriction enzymes EcoRI and PstI. The digested products were ligated to a vector pTrc99A (produced by Amersham Pharmacia Biotech Co., Ltd.) that had been digested with EcoRI and PstI in advance, and *Escherichia coli* BL21(DE3) was transformed with the reaction solution. The transformants obtained were shake-cultured overnight in a 2×YT liquid medium containing 50 mg/l of ampicillin and then IPTG (isopropyl β-D-thiogalactopyranoside) was added so as to bring the transformants to a final concentration of 1 mM, followed by further culture for 2 hours. Observation with a microscope indicated formation of an inclusion body in the cells. Therefore, the clone was named as an expression clone (1).

EXAMPLE 4

In a 2-liter baffled Erlenmeyer flask was charged 750 ml of a 2×YT liquid medium containing 50 mg/l of ampicillin and the expression clone (1) obtained in Example 3 was inoculated therein. The medium was shake-cultured at 37° C. 16 hours afterwards, IPTG is added to the medium so as to bring it to a final concentration of 1 mM, and the medium was further cultured for 2 hours. The cultured medium was centrifuged to recover from the culture solution bacterial cells, which were washed with a 10 mM potassium phosphate buffer solution, pH 7.0. Again the suspension was centrifuged to recover the bacterial cells, which were suspended in the above-mentioned buffer solution to finally make it into 120 ml.

10 g per cup of leaf mold was measured out and charged in 40 plastic-made food cups of 6 cm in diameter. In 20 cups out of them was dispersed 1 ml per cup of the suspension of the expression clone (1) and 1 ml per cup of water as blank was dispersed in the remaining 20 cups, followed by well mixing. In each of the food cups, one first instar larva of *Anomala cuprea* was released and fed under a condition of 25° C. Mortality of the larvae and mean body weight of the surviving larvae were measured with a lapse of time to verify the insecticidal activity and larvae growth inhibiting activity of the expression clone (1).

Figure 2:
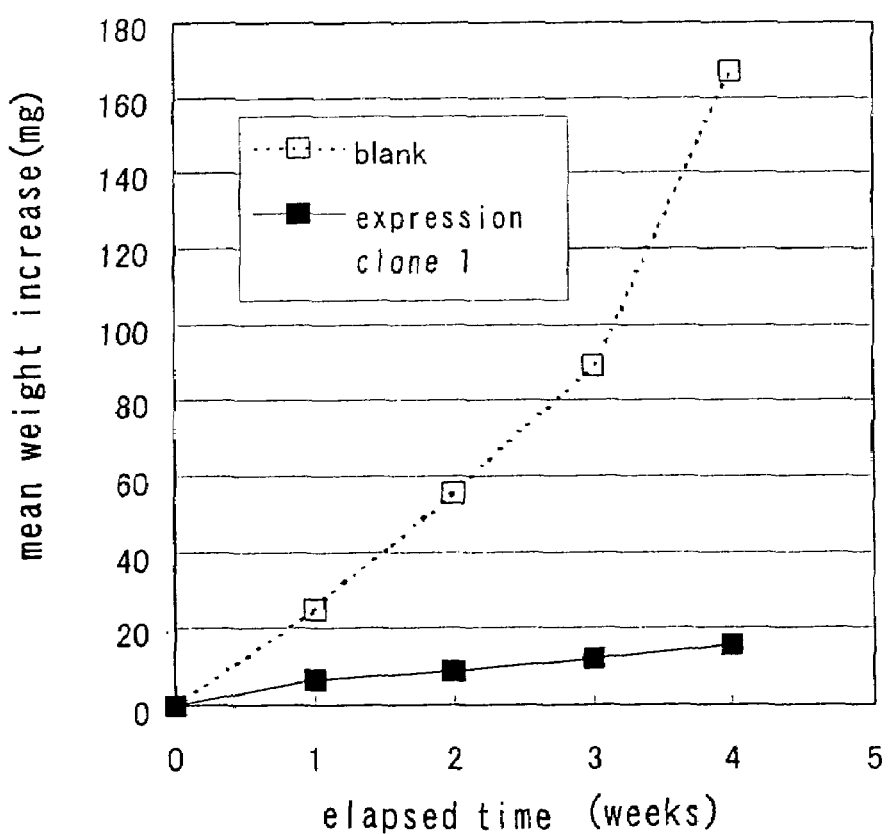
FIG. 2 is a diagram illustrating a larvae growth inhibiting effect of a polypeptide produced by the polynucleotide on a Scarabaeidae insect (larva of *Anomala cuprea*) performed in Example 4.

The results are shown in Table 1 and FIG. 2. A lot where the expression clone (1) was dispersed showed an increase in mortality, and on $5^{th}$ week, high mortality of 95% was obtained. Further, the mean body weight of surviving larvae in the lot where the expression clone (1) was dispersed did not substantially increase but remained at a low level as compared with the blank. These results confirmed that the expression clone (1), that is, the polypeptide of the present invention has a larvae growth inhibiting or insecticidal activity.

TABLE 1

| test lot | Cumulative Mortality (%) | | | | |
|---|---|---|---|---|---|
| | $1^{st}$ week | $2^{nd}$ week | $3^{rd}$ week | $4^{th}$ week | $5^{th}$ week |
| Expression clone | 5.0 | 45.0 | 65.0 | 80.0 | 95.0 |
| Blank | 5.0 | 5.0 | 5.0 | 5.0 | 5.0 |

EXAMPLE 5

In a 2-liter baffled Erlenmeyer flask was charged 750 ml of a 2×YT liquid medium containing 50 mg/l of ampicillin and the expression clone (1) obtained in Example 3 was inoculated therein. The medium was shake-cultured at 37° C. After 16 hours, IPTG was added so as to bring the medium to a final concentration of 1 mM and the medium was further cultured for 2 hours. The culture medium was centrifuged to recover from the culture solution bacterial cells, which were washed with a 10 mM potassium phosphate buffer solution, pH 7.0. Again the suspension was centrifuged to recover the bacterial cells, which were suspended in the above-mentioned buffer solution to finally make it into 75 ml, thus making it as an expression clone suspension.

On the other hand, the sporangia of *Bacillus popilliae semadara* were collected from larvae of *Anomala cuprea* infected with milky disease and washed with water. They were suspended again in water to a density of $8 \times 10^7$ sporangia/ml to make it as a sporangia suspension.

80 plastic-made food cups of 6 cm in diameter, each of which was charged with 25 g of leaf mold that was measured out, were prepared. In 20 cups out of them was dispersed 1 ml per cup of the suspension of the expression clone (1), in other 20 cups was dispersed 0.5 ml per cup of the sporangia suspension, in still other 20 cups was dispersed 1 ml of the expression clone suspension together with 0.5 ml of the sporangia suspension, and in the remaining 20 cups was dispersed 1 ml per cup of water, followed by well mixing. In each of the food cups, a second instar larva of *Anomala cuprea* was released one by one and fed under a condition of 25° C. for 21 days. Mortality of the larvae and mean body weight of the surviving larvae were measured with a lapse of time to verify synergistic effects in the insecticidal activity and the larvae growth inhibiting activity of the expression clone (1) used in combination with the sporangia.

Figure 3:
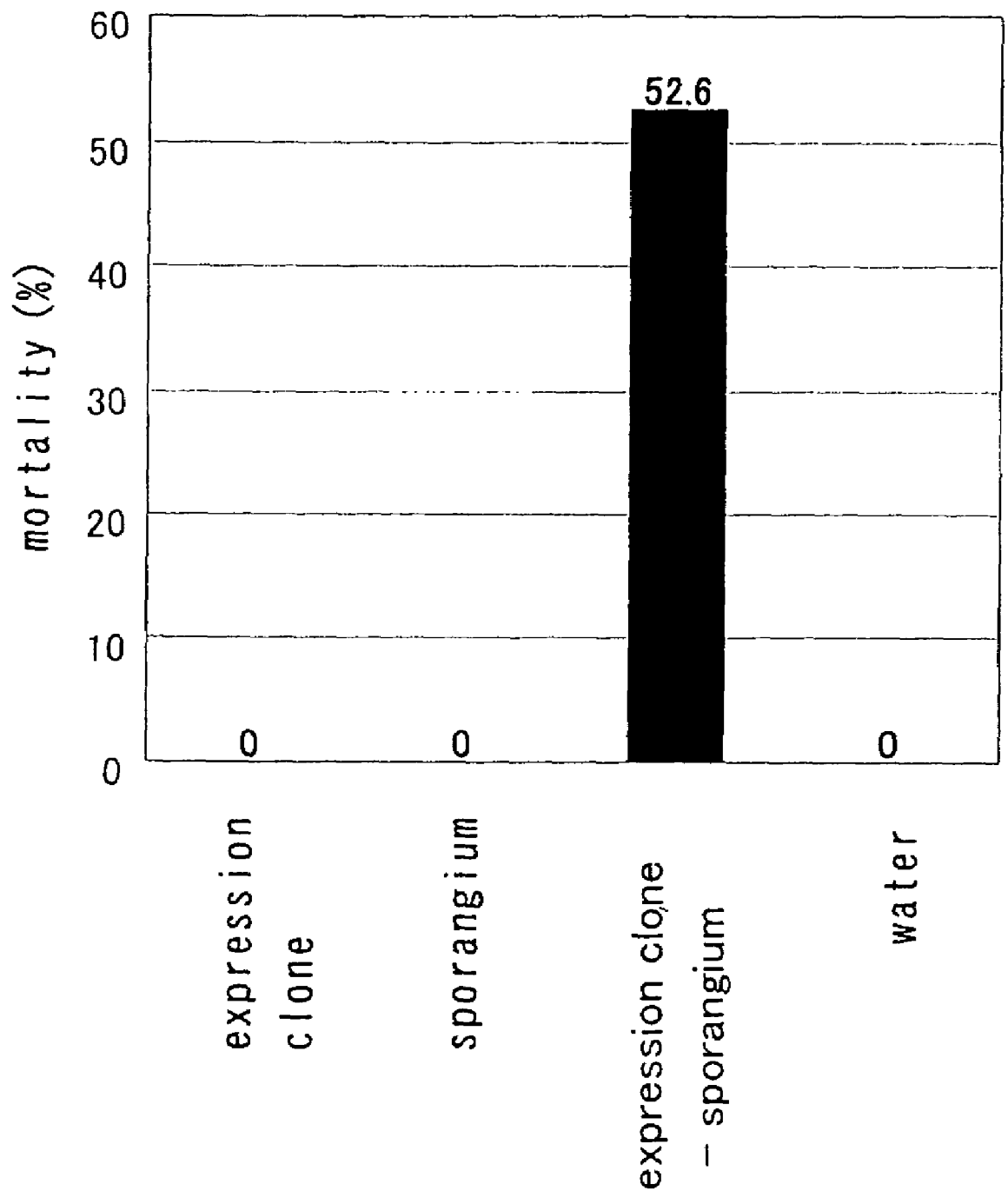
FIG. 3 is a diagram illustrating an insecticidal effect of biological tests performed in Example 5.
Figure 4:
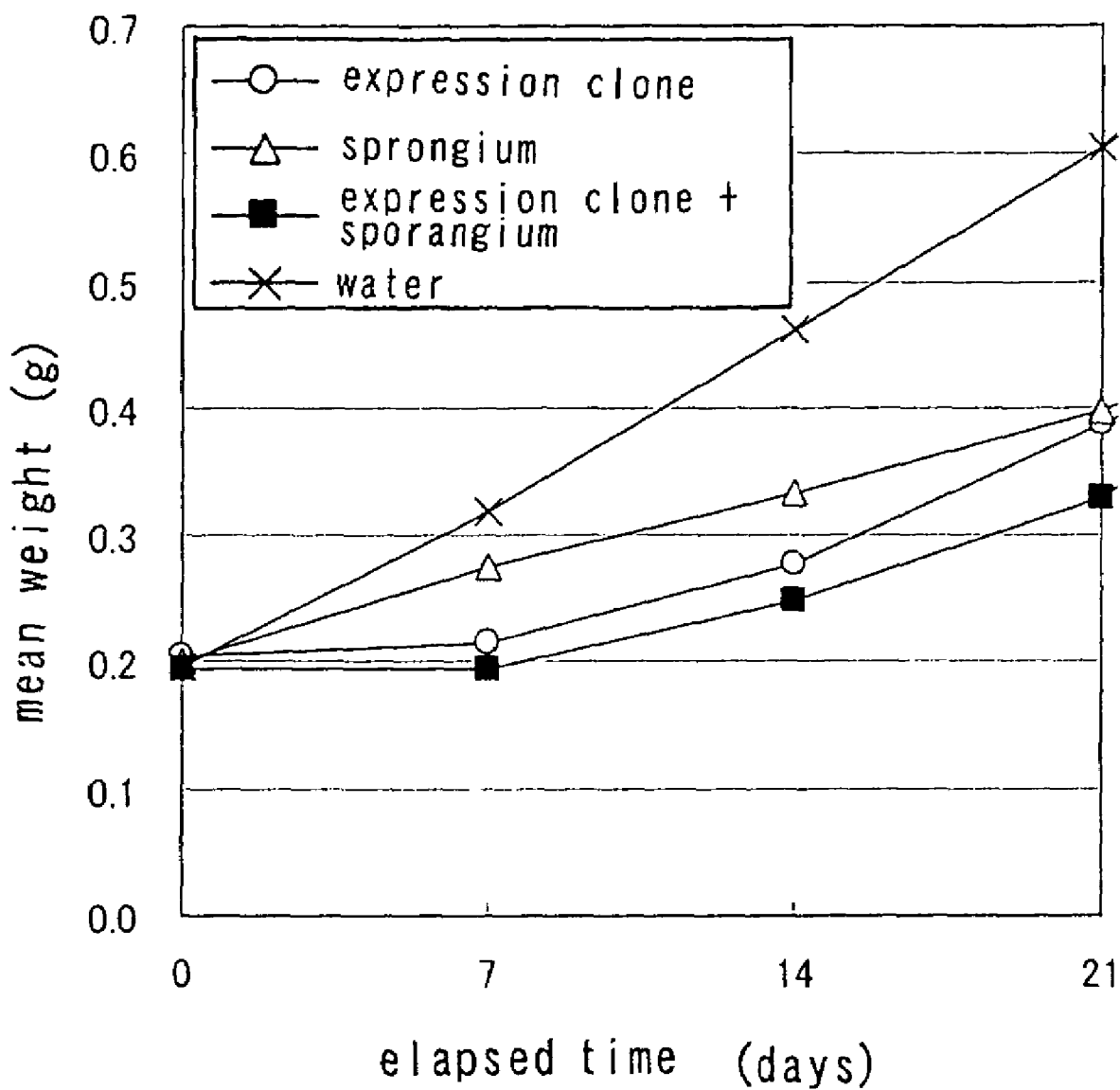
FIG. 4 is a diagram illustrating the larvae growth inhibiting effect of the biological tests performed in Example 5.

The results are shown in FIGS. 3 and 4. Dispersion of the suspension of the expression clone (1) or the sporangia alone exhibited a larvae growth inhibiting effect but did not exhibit a sufficient insecticidal effect. In contrast, when the expression clone (1) and the sporangia were dispersed in combination, an abrupt increase in mortality was observed, so that synergistic effect was confirmed.

EXAMPLE 6

Polynucleotides having the nucleotide sequences of SEQ ID NO: 11 and SEQ ID NO: 13 corresponding to parts of complementary strands of SEQ ID NO: 17 and SEQ ID NO: 19, respectively, were prepared by chemical synthesis. PCR performed by using the polynucleotides as primers and a chromosomal DNA of *Bacillus popilliae semadara* as a template indicated amplification of about 4.2 kb fragments. TA cloning of the fragments gave rise to a number of clones, some of which were subjected to determination of the nucleotide sequence of the insert portion by sequencing. As a result, polynucleotides having the nucleotide sequences of SEQ ID NO: 17 and SEQ ID NO: 19 were obtained. Therefore, it revealed that the polynucleotide of the present invention can also be obtained by PCR using the polynucleotides having the nucleotide sequences of SEQ ID NO: 11 and SEQ ID NO: 13, respectively.

EXAMPLE 7

A chromosomal DNA was collected from the bacterial cells of *Bacillus popilliae var. popilliae Mame* by an ordinary method. On the other hand, based on the nucleotide sequence of the gene encoding the polypeptide constituting the parasporal body of *Bacillus popilliae semadara* as a reference, polynucleotides having the nucleotide sequences of SEQ ID NO: 11 and SEQ ID NO: 14, respectively, were chemically synthesized. PCR performed using the polynucleotides as primers and the chromosomal DNA as a template indicated amplification of about 4.3 kb fragments. TA cloning of the fragments gave rise to a number of clones, one of which was subjected to determination of the nucleotide sequence of the insert by sequencing. As a result, a polynucleotide having the nucleotide sequence of SEQ ID NO: 3 was obtained. This was further translated to obtain the amino acid sequence of SEQ ID NO: 4.

EXAMPLE 8

Polynucleotides having nucleotide sequences of SEQ ID NO: 12 and SEQ ID NO: 13, respectively, were prepared by chemical synthesis. PCR performed by using the polynucleotides as primers and the chromosomal DNA prepared as described above as a template indicated amplification of about 4.2 kb fragments. TA cloning of the fragments gave rise to a large number of clones, one of which was subjected to determination of the nucleotide sequence of the insert portion by sequencing. As a result, a polynucleotide having the nucleotide sequence of SEQ ID NO: 5 was obtained. This was further translated to obtain the amino acid sequence of SEQ ID NO: 6.

EXAMPLE 9

Polynucleotides having the nucleotide sequence of SEQ ID NO: 15 corresponding to a part of a complementary strand of SEQ ID NO: 3 and the nucleotide sequence of SEQ ID NO: 11, respectively, were prepared by chemical synthesis. PCR performed by using the polynucleotides as primers and the chromosomal DNA prepared as described above as a template indicated amplification of about 1.2 kb fragments. TA cloning of the fragments gave rise to a large number of clones, one of which was subjected to determination of the nucleotide sequence of the insert portion by sequencing. As a result, a polynucleotide having the nucleotide sequence of SEQ ID NO: 7 was obtained. This was further translated to obtain the amino acid sequence of SEQ ID NO: 8.

EXAMPLE 10

The chromosomal DNA obtained as described above was degested with restriction enzyme XhoI and the fragments were ligated with SalI Cassette contained in a LA PCR in vitro Cloning Kit produced by Takara Shuzo Co., Ltd. On the other hand, a polynucleotide having the nucleotide sequence (SEQ ID NO: 16) corresponding to a part of a sequence of SEQ ID NO: 3 was prepared by chemical synthesis. Then, PCR was performed by using the polynucleotide and a Cassette primer C1 attached to the Kit as primers and the ligated chromosomal DNA fragment as a template. As a result, amplification of about 3 kb fragments was observed. TA cloning of the fragments gave rise to a large number of clones, one of which was subjected to determination of the nucleotide sequence of the insert portion by sequencing. As a result, a clone having a polynucleotide having the nucleotide sequence of SEQ ID NO: 9 coupled in tandem to downstream of the latter half of the nucleotide sequence of SEQ ID NO: 3 was obtained. The nucleotide sequence of SEQ ID NO: 9 was further translated to obtain the amino acid sequence of SEQ ID NO: 10.

EXAMPLE 11

The amino acid sequences of the polypeptides of the parasporal bodies existing in *Bacillus popilliae* obtained in Examples 2, 7 and 8 and the nucleotide sequences of the polynucleotides encoding them were comparatively studied by using gene information processing software GENETYX-WIN (Software Development Co., Ltd.). As a result, sequences that have very high homology of 98% or more in the amino acid sequence and are considered to be specific to the parasporal body of *Bacillus popilliae*, i.e., the amino acid sequence of SEQ ID NO: 2 and the corresponding nucleotide sequence of SEQ ID NO: 1 were found. The portions indicated by an arrow in FIGS. 5 to 7 correspond to the amino acid sequence of SEQ ID NO: 2.

Note that these sequences have homology of 9% or less in the amino acid sequence to the sequence isolated from *Bacillus popilliae* subsp. *Melolonthae* H1 described in WO97/14798, and hence is completely different therefrom.

EXAMPLE 12

PCR was performed by using a chromosomal DNA of *Bacillus popilliae var. popilliae Mame* as a template and polynucleotides of SEQ ID NO: 12 and SEQ ID NO: 14 as primers to amplify about 4 kb fragments, which were purified and recovered by electrophoresis and subsequent cutting out. The fragments were ligated to a pT7Blue vector (Novagen, Inc.) and *Escherichia coli* DH5α was transformed with the ligation product. Among the obtained clones, a clone harboring the pT7Blue with the 4 kb insert downstream of lac promoter in a direction of sense to form a fusion polypeptide with an N-terminal portion of a lacZ polypeptide was selected. This was named as an expression clone (2) and used in the following tests of production of a polypeptide and effects thereof.

EXAMPLE 13

Ten 300 ml-capacity Erlenmeyer flasks containing 200 ml of a 2×YT medium were prepared. In 5 flasks out of them was inoculated the expression clone (2) obtained in Example 12 and shake-cultured at 37° C. overnight. As a comparative control clone, *Escherichia coli* DH5α having a pT7Blue vector having inserted therein no 4 kb fragment was inoculated in the remaining 5 flasks and cultured in the same manner as the above. After completion of the culture, bacterial cells were observed with a microscope. As a result, formation of inclusion body in the bacterial cells was observed only in the case of the expression clone (2). The bacterial cells were once recovered from each flask by centrifugation and after washing with water, the bacterial cells were centrifuged again to recover them and then suspended in water to finally make it into 23 ml.

20 g per cup of leaf mold was measured out and charged in 15 plastic-made food cups of 6 cm in diameter. In 5 cups out of them was added a suspension of the expression clone and in other 5 cups out of them was added a suspension of the comparative control clone, followed by well mixing. In the remaining 5 cups was dedicated to blank tests of no addition.

Figure 8:
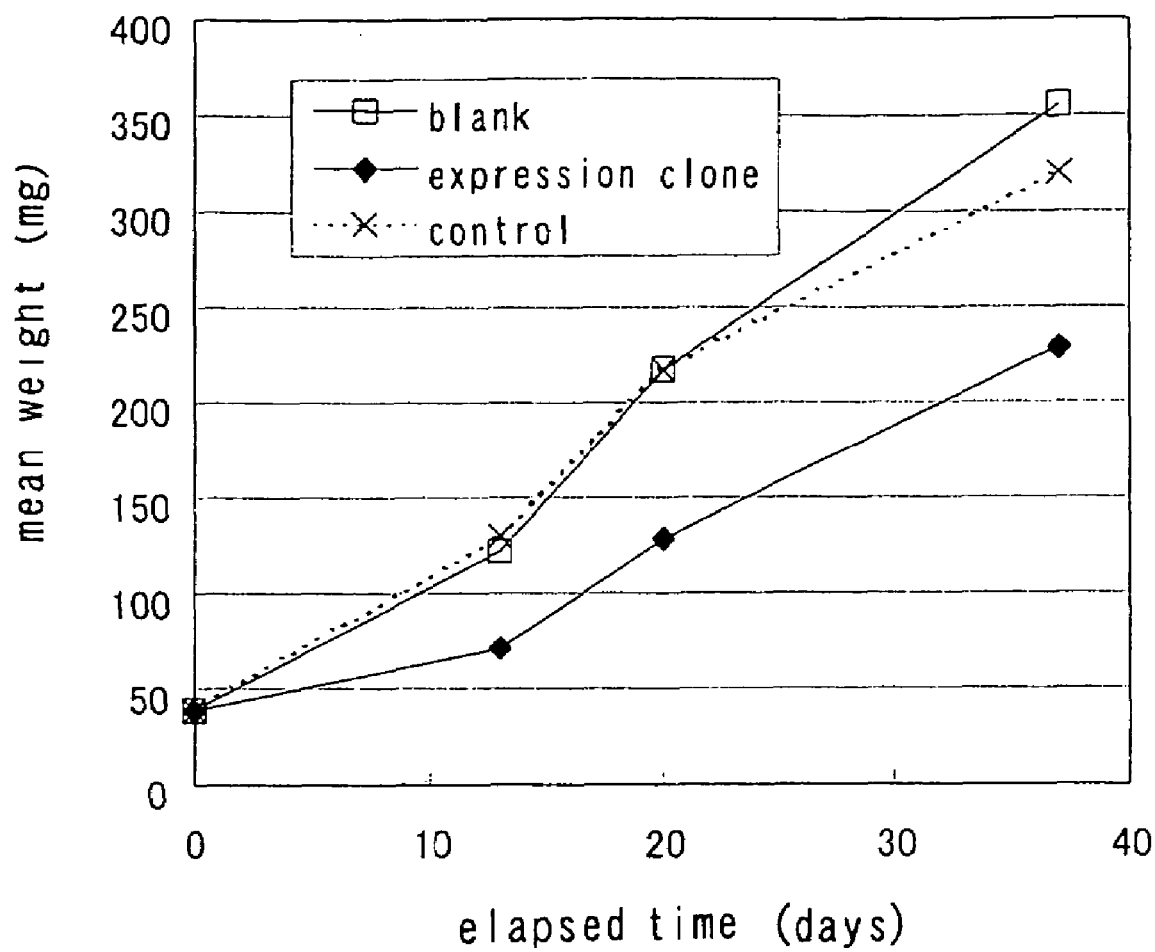
FIG. 8 is a diagram illustrating a larvae growth inhibiting effect on a Scarabaeidae insect of a polypeptide produced by a polynucleotide in Example 13 of the present invention (larvae of *Anomala cuprea*).

In each of the food cups, one first instar larva of *Anomala cuprea* was released and fed under a condition of 25° C. The body weights of larvae were measured with a lapse of time and compared to verify the larvae growth inhibiting activity of the expression clone (2). In contrast to the blank test and the control lot, a lot where the expression clone (2) was added apparently suppressed increase in mean body weight (FIG. 8), which confirmed that the expression clone (2), that is, the polypeptide of the present invention has a larvae growth inhibiting effect.

What is claimed is:

1. An isolated polynucleotide comprising the nucleotide sequence of nucleotides 224 to 4255 of SEQ ID NO:19.

2. A vector comprising the isolated polynucleotide of claim 1.

3. An isolated host cell comprising the vector of claim 2.

* * * * *